United States Patent [19]
Roth

[11] Patent Number: 5,629,865
[45] Date of Patent: May 13, 1997

[54] PULSE-ECHO ULTRASONIC IMAGING METHOD FOR ELIMINATING SAMPLE THICKNESS VARIATION EFFECTS

[75] Inventor: Don J. Roth, Lakewood, Ohio

[73] Assignee: The United States of America as represented by the Administrator of the National Aeronautics and Space Administration, Washington, D.C.

[21] Appl. No.: 546,972

[22] Filed: Oct. 23, 1995

[51] Int. Cl.$^6$ .......................... G01N 29/00; G01N 29/04
[52] U.S. Cl. ................ 364/508; 73/602; 73/620; 73/600
[58] Field of Search .................. 364/507, 508; 73/597, 598, 599, 600, 602, 606, 607, 609, 610, 615, 620, 627, 634; 367/8, 13

[56] References Cited

U.S. PATENT DOCUMENTS

| | | | |
|---|---|---|---|
| H1082 | 8/1992 | Bylenok et al. | 73/602 |
| 3,848,460 | 11/1974 | Bantz et al. | 73/67.5 R |
| 4,471,785 | 9/1984 | Wilson et al. | 128/660 |
| 4,866,614 | 9/1989 | Tam | 364/413.25 |
| 4,947,351 | 8/1990 | Moran et al. | 364/507 |
| 5,533,401 | 7/1996 | Gilmore | 73/622 |

OTHER PUBLICATIONS

Simultaneous Determination of Ultrasonic Velocity, Plate Thickness and Wedge Angle Using One-Side Contact Measurements —David K. Hsu, Allan M. Ayers et al.

NASA Technical Paper 3377 1993–Quantitative Mapping of Pore Fraction Variations in Silicon Nitride Using an Ultrasonic Contact Scan Technique –Don J. Roth.

NASA Technical Memorandum 4545–PSIDD: A Post-Scan Interactive Data Display System for Ultrasonic Scans. Don J. Roth.

Numerical Recipes —The Art of Scientific Computing —William Press, Brian Flannery, Saul A. Teukolsky and William T. Vetterling.

NASA Technical Memorandum 4106 —Interfacing Laboratory Instruments to Multiuser, Virtual Memory Computers by Edward R. Generazio, David B. Stang, and Don J. Roth.

Ultrasonic Velocity Measurement for the Determination of Density in Polyethylene by L. Piche —reprinted from Polymer Engineering and Science, vol. 24, No. 17, Mid Dec. 1984.

"Ultrasonic Velocity Measurement for the Determination of Density in Polyethylene", L. Piche, Polymer Engineering and Science, vol. 24, No. 17.

Primary Examiner—Emanuel T. Voeltz
Assistant Examiner—Tony M. Cole
Attorney, Agent, or Firm—Kent N. Stone

[57] ABSTRACT

A pulse-echo, immersion method for ultrasonic evaluation of a material which accounts for and eliminates nonlevelness in the equipment set-up and sample thickness variation effects employs a single transducer and automatic scanning and digital imaging to obtain an image of a property of the material, such as pore fraction. The nonlevelness and thickness variation effects are accounted for by pre-scan adjustments of the time window to insure that the echoes received at each scan point are gated in the center of the window. This information is input into the scan file so that, during the automatic scanning for the material evaluation, each received echo is centered in its time window. A cross-correlation function calculates the velocity at each scan point, which is then proportionalized to a color or grey scale and displayed on a video screen.

15 Claims, 5 Drawing Sheets
(1 of 5 Drawings in Color)

PULSE-ECHO ULTRASONIC IMAGING METHOD FOR ELIMINATING SAMPLE THICKNESS VARIATION EFFECTS

ORIGIN OF THE INVENTION

The invention described herein was made by an employee of the United States Government and may be manufactured and used by or for the Government for governmental purposes without payment of any royalties thereon or therefor.

BACKGROUND OF THE INVENTION

1. Field of the Invention

The invention relates to ultrasonic evaluation of material properties. More particularly, the invention relates to non-destructive ultrasonic evaluation of materials by measuring velocity using a single transducer pulse-echo immersion system, automatic scanning and digital imaging, which provides a video image of the sample in color or grey scale which is a map of a material property such as porosity fraction.

2. Background Of the Disclosure

Nondestructive evaluation applicable to evaluating properties of materials such as ceramics, metals, plastics and various composites are known to those skilled in the art and include x-radiography, ultrasound or ultrasonic evaluation, and thermal methods. These methods provide an efficient, quasi-quantitative measure of material homogeneity, but often lack the precision necessary for microstructure evaluation of high-performance materials, such as high temperature oxidation resistant ceramics and the like. The development and use of materials for high-performance applications requires detailed, quantitative knowledge of microstructural and compositional variability for defining acceptable levels of variability and for rejecting those materials and processes that yield sample-to-sample and within-sample variations likely to result in unacceptable property (e.g., strength, thermal conductivity, oxidation resistance, resistance to spalling, etc.) variations. Such variability must be precisely characterized either directly in terms of property measurement or indirectly through microstructural characterization where microstructure-property relations have been previously established.

Repeated, uniformly spaced ultrasonic contact measurements have been successful for quantifying and mapping inhomogeneity in various ceramics (e.g., SiC, $Al_2O_3$, $YBa_2Cu_3O_7$ and $Si_3N_4$) and metals in terms of ultrasonic material properties such as reflection coefficient, velocity and attenuation coefficient as mentioned, for example, by Roth, et. al. in *Quantitative Mapping of Pore Fraction Variations in Silicon Nitride Using an Ultrasonic Contact Scan Technique*, NASA TP 3377 (1993). This publication describes quantitatively characterizing material (e.g., $Si_3N_4$) microstructure in terms of actual ultrasonic wave parameters. The wave parameters include reflection coefficient, attenuation coefficient and velocity. A post-scan interactive data display system is used for comparing ultrasonic properties at different locations within samples and viewing the resultant ultrasonic images. Further refinement of this process is disclosed by Roth, et. al. in *PSIDD: A Post-Scan Interactive Data Display System for Ultrasonic Scans*, NASA TM-4545 (1993). This process relates to contact scans and does not disclose how to account for thickness variations in the sample being measured. Piche discloses a single transducer immersion method for evaluating plastic using a technique in which 16 scan points are pulsed for the sample and the results evaluated using regression analysis [L. Piche, *Ultrasonic Velocity Measurement for the Determination of Density in Polyethylene*, Polymer Eng. &. Sci.,v. 24, n.17, p. 1358–58 (Dec. 1984]. This method does not relate to forming an image of the sample property, nor does it provide an experimental technique that automatically accounts for nonlevelness and thickness variation during a scan procedure required to form an image. Consequently, a need still exists for a method which will permit ultrasonic material evaluation that will account for nonlevelness and thickness variations in the material, require only a single transducer, eliminate problems associated with physical contact between the transducer and sample or buffer rod, and display, on a video screen in gray scale or color, an image of the scanned material which is a map of an internal structural property of the material, such as porosity fraction.

SUMMARY OF THE INVENTION

The invention relates to a method for nondestructive ultrasonic evaluation of materials by measuring velocity using a pulse-echo immersion system with automatic scanning, echo cross-correlation and digital imaging to obtain a grey scale or color image of the sample. The velocity values obtained for each scan point are scaled on a grey or color scale and displayed on a video screen which shows a material property, such as porosity fraction. Prior to the automatic scanning, nonlevelness in the set-up and sample thickness variation effects are accounted for and eliminated by insuring that the echoes at each scan point are first gated and input into a scan parameter file in a computer, so that during the subsequent automatic scanning each received echo is centered in the time window set for it. While it is possible, but not practical to do a manual prescan at each and every scan point needed for a two dimensional video image of the material property being evaluated, many sample thickness variations are in the form of a uniform thickness variation from one edge to another. In this case of uniform thickness variations from one edge to another, preliminary scans are performed along a single line in both the x- and y-directions of the sample to provide slant correction factors. The slant correction factors are input into the scan parameter file so that any wedge-shape variations are taken into account during the automatic scanning for the material evaluation, to insure that each echo received during the automatic scanning is centered within the time window. A single transducer is used in a preferred embodiment of the invention.

In the immersion method of the invention, the material to be evaluated is surrounded by a liquid and positioned over an acoustic reflector which is also immersed in the liquid. An ultrasonic wave of a known frequency is transmitted through the liquid and four separate echoes are recorded and evaluated at each scan point. Each echo is received as an analog waveform which is digitized and stored in a computer. The echoes received, digitized and stored during the sample evaluation scans are the first two succesive echoes reflected off the back surface of the sample, the first echo reflected off the front surface of the accoustic reflector in which the received wave has passed through the sample, and the forth is the first echo reflected off the front surface of the reflector with the sample not present, so that the received wave does not pass through the sample. This means that at least two separate scans must be made, with and without the sample present between the transducer and reflector. However, as a practical matter it is difficult from both a hardware and software perspective to accomplish this in just two scans and obtain maximum time resolution and thus maximum accuracy. Consequently three or four separate scans are performed, with three being faster and four being more accurate. The choice is left to the discretion of the practitioner. In the embodiment in which four separate scans are performed during the sample evaluation, the ultrasonic wave goes through both the liquid and the material during the first three scans. For the forth scan the material sample is removed so that the transmitted wave is reflected off the front surface of the reflector without going through the material. Although the order is not important, it is convenient to receive the first echo reflected off the back surface of the material during the first scan and the second successive echo reflected off the back surface of the sample during the second scan. During the third scan in which the transmitted wave goes through both the immersion liquid and the material sample, the first echo reflected off the front surface of the reflector is received. The first echo reflected off the front reflector surface is received during the fourth scan when the sample is not present. This process is repeated at a plurality of scan points sufficient to produce a video image of a microstructural property, such as porosity, of the material. After the scanning is completed, the digitized waveforms are retrieved from the computer and the time delay between the first two successive echoes received from the back surface of the material at each scan point is determined. The time delay between the two different reflections or echoes received off the reflector (with and without the transmitted wave going through the sample) is also determined for each scan point. The wave velocity at each scan point is then calculated from the time delays and the speed of the transmitted wave in the liquid. The velocity values for all of the scan points are scaled to corresponding proportional color or grey scale values which are then displayed on a video screen or cathode ray tube (CRT). Thus, in this embodiment of the invention, four separate scans are made at each scan point to separately receive, as analog waveforms, the first two successive ultrasonic echoes off the back surface of the sample and the first echo off the front surface of the reflector both with and without going through said sample; digitizing and storing the waveforms; retrieving the digitized waveforms; determining the received time delay between the first two successive sample back surface echoes and between the two reflector front surface echoes; calculating the wave velocity at each scan point; scaling the calculated velocities to corresponding proportional color or gray scale values, and displaying the resulting image. The wave velocity at each scan point is calculated from $$v = c \left( \frac{\Delta t}{2\tau} + 1 \right)$$

wherein $2\tau$ is the received time delay between the two successive sample back surface echoes, wherein $\Delta t$ is the time delay between the two different echoes received from the reflector with and without going through the sample, and wherein c is the speed of the transmitted ultrasound wave in the liquid. The embodiment in which three separate scans are made is similar to that in which four separate scans are made, with the difference being that during the first scan the first two succesive reflections or echoes off the back surface of the sample are received, digitized and stored. It will be noted that above equation does not include the sample thickness value. This means that the thickness of the sample need not be measured or known.

As set forth above, prior to the two, three or four scans during which the sample is evaluated, nonlevelness and sample thickness variations are accounted for and eliminated by pre-scans to insure that the received reflections or echoes are within their set time windows to provide a complete waveform for evaluation and cross-correlation to accurately obtain the time delay data used in calculating the velocity values. In the case of a sample having a thickness variation in the form of a uniform thickness variation from one edge to another, preliminary scans are performed along a single line in both the the x- and y-directions of the sample to provide slant correction factors. The slant correction factors are input into the computer scan parameter file so these variations are taken into account during the automatic scanning for the material evaluation.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION

Figure 1:
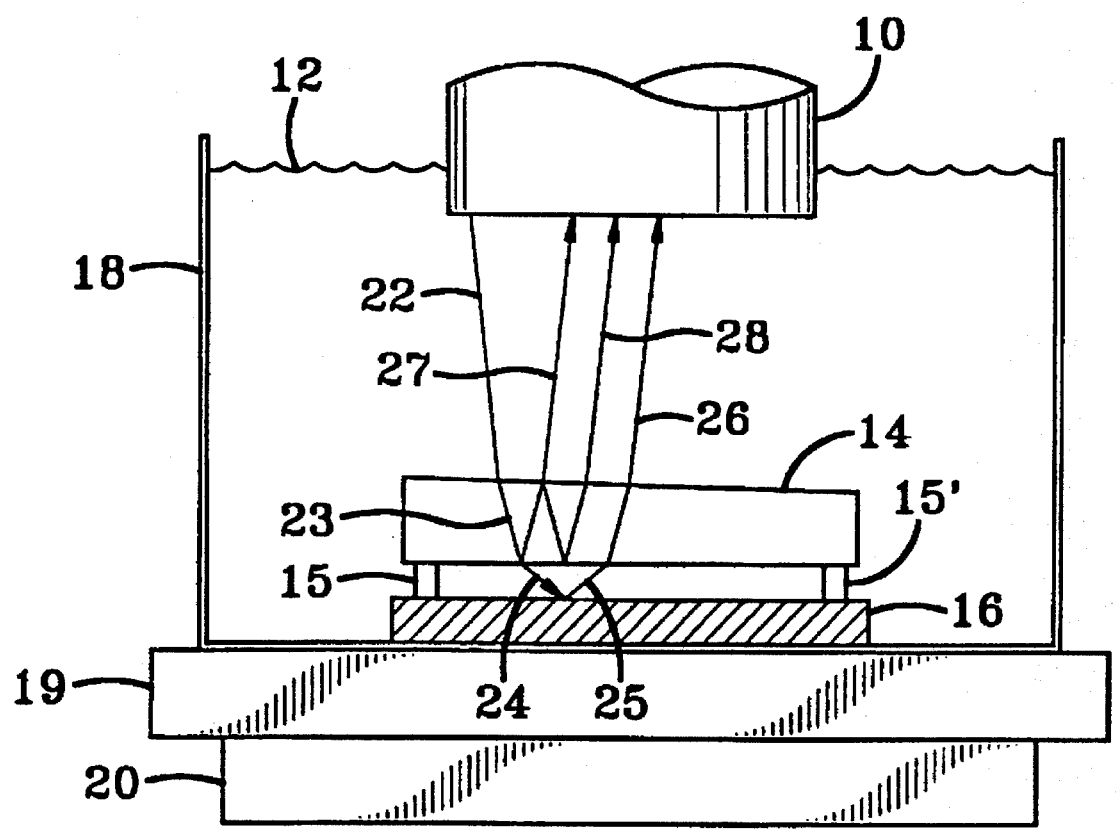
FIG. 1 schematically illustrates the spatial relationship between the transducer, liquid, material sample, reflector plate and the transmitted and reflected ultrasonic echo waves in the practice of the invention.
Figure 2A:
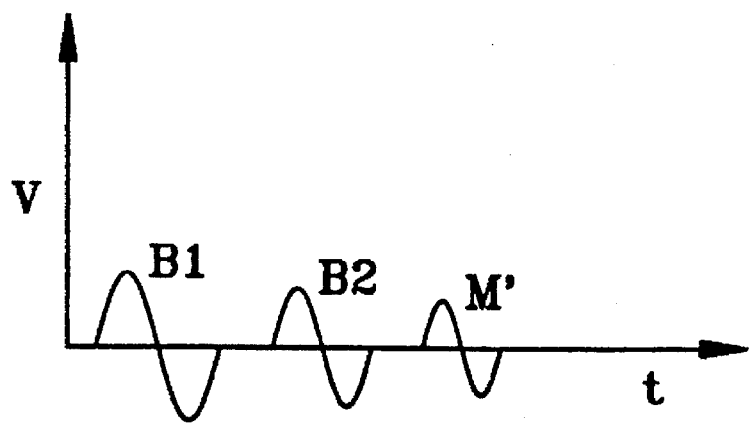
FIGS. 2(a) and 2(b) graphically illustrate the amplitude and time delay of the received analog ultrasonic echoes reflected off the material sample and reflector.
Figure 2B:
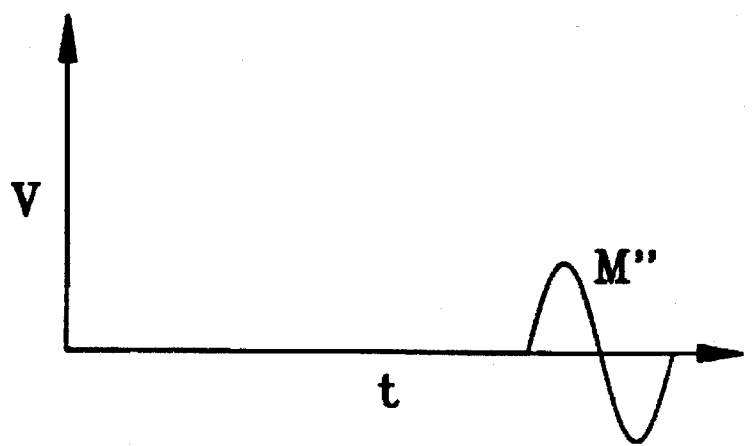

Referring to FIG. 1, transducer 10 is schematically shown as partially immersed in a liquid 12 which is the immersion fluid. Material sample 14 is shown positioned in the fluid 12 between the transducer 10 and reflector plate 16 in container or tank 18 located on top of x- and y-direction motorized stages 19 and 20. Supports 15 and 15' maintain sample 14 above reflector 16. The transducer 10 and motorized x- and y-direction stages 19 and 20 are electrically connected by means not shown to a pulser-receiver (not shown) and to means (not shown) for moving the x- and y- stages in their respective directions. Similarly, liquid 12 is connected to means not shown for maintaining the temperature of the liquid preferably within at least about ± 1° F. of the temperature at which the scans are to be run. It is possible to maintain the liquid temperature within ±0.1° F. The better the temperature control, the more accurate the results will be. For example, if the temperature of the immersion liquid is ±1° F. and the liquid is water, a 1.5% error in velocity is possible. If the porosity fraction or other property of the material at a particular point is such as to result in a velocity value difference in the sample of 2%, only a 0.5% microstructural velocity difference might be detected if a ±1° F. temperature variation is present during the scan. At each scan point an ultrasonic wave 22 of a known frequency is transmitted from transducer 10 through liquid 12 and into material sample 14. Entering material 14 causes part of wave 22 to be reflected (not shown) off the top surface of the sample, with the rest of the wave passing through the material as 23. Part of wave 23 continues through the material and to the top surface of accoustic reflector 16 as 24, is reflected back off the top surface of reflector 16 as 25, passes back through the sample 14 and returns to the transducer 10 as wave 26. A portion of wave 23 is reflected off the back surface of the sample and returns to the transducer as 27. Part of the wave 23 reflected off the back surface of the material is reflected off the top surface, returns to the back surface, is again reflected back to the top surface and exits as wave 28. Waves 27 and 28 are the first two successive back surface reflected waves used in the method of the invention at each scan point. Not shown is the wave transmitted through the liquid and reflected back to the transducer without going through the material. This wave which is not shown and wave 26 are the two reflector front surface echoes used in the method of the invention. Motorized stages 19 and 20 form part of an automated scanning system which incrementally moves in both the x- and y-directions to obtain an ordered array of points across the entire surface of the material sample. A 20 MHz, broadband transducer was used in the practice of the invention. Broadband transducers emit a broadband frequency content dominated by a center frequency. That is, they are made to emit at a nominal frequency proximate that of the design frequency (e.g., 20 MHz), with a Gaussian fall-off on either side of the nominal center frequency. Thus, a 20 MHz broadband transducer will also emit frequencies slightly above and below the nominal center frequency of 20 MHz. In the Piche article referred to above, although the two different reflector front surface echoes are captured and recorded, the first front surface echo and the first back surface echo are captured and recorded. This is different from the method of the invention which captures and records the first two successive sample back surface echoes and not the first front sample surface echo. Further, Piche does not use automatic sample scanning or digital imaging. FIGS. 2(a) and 2(b) graphically illustrate the reflected waveforms received and displayed on the CRT of an oscilloscope as time domain analog waveforms. Turning to FIGS. 2(a) and 2(b), the intensity or strength of the received waveform is displayed as voltage amplitude, which is the ordinate of the graph, and the received time delay as the abscissa. In this representation, B1, B2 and M' refer to waves 27.28 and 26 of FIG. 1, respectively, with M" representing the wave transmitted through the liquid and reflected off the front surface of the reflector without passing through the material sample. The time delay between the first two successive echoes reflected from the back or bottom surface of the material back to the transducer, B1 and B2, is readily obtained, as is the time delay between the two reflections received from the front surface of the reflector, M' and M". Since the velocity of the ultrasonic wave is faster in denser media than in less dense media, voids, delaminations, porosity and other density variables within the material are obtained as a function of the speed of the wave, which is determined by the time delay between the first two successive echoes received which have been reflected off the back of the material, and the time delay between the two different reflections from the front surface of the reflector. As set forth above under SUMMARY, the speed or velocity of the transmitted wave traveling through the material sample is determined according to the simple equation:

$$v = c \left( \frac{\Delta t}{2\tau} + 1 \right)$$

wherein $2\tau$ is the received time delay between the two successive material sample back surface echoes, wherein $\Delta t$ is the time delay between the two different echoes received from the reflector with and without going through said sample, and wherein c is the speed of the transmitted wave in the liquid. This equation is accurate for a single point measurement. Prior art ultrasonic velocity scan techniques such as that of Roth et. al. in the quantitative mapping publication referred to above, assume that the material sample is of uniform thickness and do not take into account nonlevelness and material thickness variations as does the method of the invention.

In the practice of the method of the invention, tank 18 may be made of any suitable material. Clear plastic such as polymethylmethacrylate (e,g., Lucite or Plexoglass) has been found useful. The sample tank contains a suitable elastic liquid, such as water, as the immersion fluid to provide an accoustic coupling between the transducer, material and reflector plate. Since the x-, y-direction scans made across the sample surface in the method of the invention can take a significant amount of time compared to that for a single point measurement and since the speed of sound in a liquid is also a function of temperature, the water is maintained at a constant temperature during the scanning. This is readily accomplished simply by using a constant temperature regulating means, such as a constant temperature water circulator, for maintaining the desired temperature constant during the ultrasonic scanning. It is convenient to keep the temperature of the water at about ambient or 68° F. ±1° F. during the scan, although other temperatures may be used if desired, as long as the temperature is maintained within no more than ±1° F. In the case of distilled, deionized water, the wave velocity may be obtained from published tables. However, tap water may be used as long as the velocity in the water is actually measured. The reflector is placed on the bottom of the tank. Other immersion liquids may be used, if desired, such as Dow Corning 704 vacuum pump oil.

The reflector is a solid plate of material having an accoustic impedance significantly different from that of the liquid or water. A flat plate of tungsten (e.g., 1/16"–1/8" thick) is preferably used, because tungsten has an accoustic impedance almost two orders of magnitude higher than water in units of $g/cm^2$-sec. The use of a tungsten plate results in the highest possible reflection amplitude of any solid material for the echoes reflecting off the front surface of the reflector plate. This large difference in accoustic impedance is important when attempting to obtain ultrasonic echoes that have to travel into and through immersion liquid and the sample, bounce off the reflector plate, and travel back through the liquid and sample to the the transducer for reception. High frequency ultrasound provides greater time resolution than lower frequencies and is therefore more desireable for greater accuracy of the velocity of the ultrasound through the sample and corresponding velocity image. The higher the frequency, the greater the velocity accuracy. By having the highest reflection amplitude possible, it is possible to use the method of the invention (a) at higher frequencies where attenuation through the sample is greater than if using lower frequencies and (b) with materials that significantly attenuate ultrasound, such as composite materials. By high frequency ultrasound is meant from 1–100 MHz, typically 3–50 MHz and more typically 10–30 MHz.

The material sample is easily positioned over the reflector plate by using spacers on top of the plate and placing the material on top of the spacers. It is important that the spacers have the same height or thickness so that the material is as level as possible. Lucite is available as sheets which are very uniformly thick and it is convenient to use 0.5" cubes of this plastic as spacers. The material sample, such as a plate of silicon nitride ceramic, is placed on the plastic spacers over the tungsten reflector plate prior to scanning.

Figure 4:
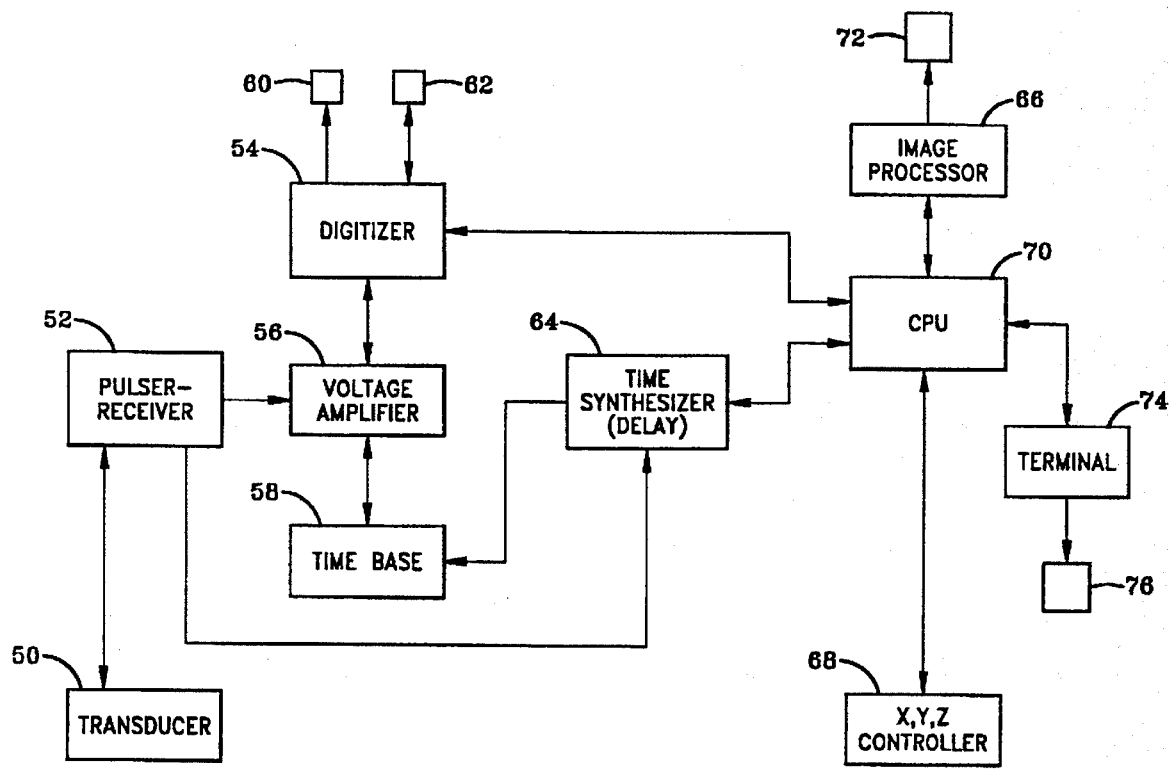
FIG. 4 is a block diagram schematically illustrating the instrumentation used in the invention.

FIG. 4 schematically illustrates, in block diagram fashion, the basic system and instrumentation used for the scanning and ultrasonic imaging according to an embodiment used in the practice of the invention.

Thus, referring to FIG. 4, the basic instrumentation includes a transducer 50, a pulser-receiver 52, and a programmable waveform digitizer 54 having associated with it a vertical voltage amplifier 56, programmable time base 58, and anolog and digital monitors 60 and 62, respectively. Also included are a time delay or synthesizer 64, an image processor 66, an X, Y, Z controller 68, computer or central processing unit (CPU) 70, and video display 72. In the embodiment shown, the computer 70 is a CPU with terminal 74 and associated video display 76 also forming part of the system. Monitors 60 and 62, along with digitizer 54, voltage amplifier 56 and time base 58 also serve as respective analog and digital oscilloscopes. The time synthesizer, time base, voltage amplifier and waveform digitizer are all general purpose interface [IEEE- 488]bus (hereinafter "GPIB") programmable and interconnected via GPIB cables. The computer 70 is programmed in Fortran and contains an image processor system which is connected to the video color and gray scale display 72. The computer controls the GPIB instrumentation and acquiring of the desired waveforms via the GPIB. The process includes data acquisition, analysis/calculation, image processing and display. The Fortran software, with callable routines in in IEX-VMS interface software to communicate with the GPIB instruments is written for instrument control and waveform acquisition following the method of Generazio, et. al. in *Interfacing Laboratory Instruments to Multiuser Virtual Memory Computers*, NASA Technical Memorandum 4106 (1985), the disclosure of which is incorporated herein by reference. The Fortran programs used in the practice of the invention including the scanning program, the analysis and cross-correlation program, the grey scale imagemaker program, and the display program are contained in the attached Appendix. The wave form digitizer is a Tektronics 7912 AD Programmable Digitizer along with a Tektronics 7A16 P Programmable Vertical Voltage Amplifier (voltage base) and a Tektronics 7B90 P Programmable Time Base. The time delay (time synthesizer) is a Hewlett Packard Model 5359A and the X, Y, Z programmable stepper motor controller and associated tables is a Klinger Scientific C-1.22. The ultrasonic pulser-receiver is a Panametrics Model 5601 and the transducer used in the scanning of the silicon nitride ceramic disk in the example below is a Panametrics 20 MHz, longitudinal, unfocused, broad band transducer. The computer is a Digital Equipment model Microvax II.

In the practice of the invention, the image processer is a Grinnell Systems Grinnell 274 Image Processing System and the Grinnell Systems GMR Series Software Package, Release 2.2, Jun. 19,1981, available from McLoud Associates, 165-F Croftich Lane, Campbell, Calif. 95008, the disclosure of which is also incorporated herein by reference. Two video displays are used, one of which is a DEC VT340 terminal, which is the user terminal attached to the computer, and a Mitsubishi 20LP is the video display monitor attached to the image processing system. High level VAX Fortran software used for driving the system is included in the Appendix as set forth above. The Grinnell library of Fortran subroutines is called from this high level software. The video display shows ultrasonic images.

The pulser-receiver applies the voltage pulse to the transducer to generate the ultrasonic waves into the sample and to the reflector plate and also receives the raw ultrasonic echo waveforms from the transducer. The approximate times where the echo waveforms are expected to occur are determined a priori (prior to the automatic scanning for the material evaluation) using the time systhesizer to find and position the echo waveforms on the oscilloscope. The time base and voltage amplifier are used to modify the time and voltage scales to view the waveforms on the oscilloscope.

Both the time base and the time synthesizer are externally triggered by the pulser-receiver (a+2 volt synchronizing pulse). Triggering occurs on the positive slope of the pulse. The time base is adjustable over the range of from 1 psec–500 msec/div on the oscilloscope, with the optimum setting for each waveform determined a priori and input to a data file in the computer. The pulser-receiver output is connected to the voltage amplifier. The voltage amplifier, selectable over the range 50 mV–1V/div, is automatically adjusted by the digitizer so that the entire received analog waveform is digitized with maximum amplitude fit onto the digital waveform monitor. The digitizer digitizes each waveform received into 512 point arrays (at a sampling rate ranging from 0.512 –1.024 GHz depending on the time base time/division setting). Each waveform is acquired 64 times and averaged to obtain a smoother waveform with averaged noise levels using a Fortran algorithm included in the scanning program in the Appendix and which is also found in the NASA Technical Memorandum 4106 referred to above. The X and Y positional and Z intensity outputs from the waveform digitizer are attached to the analog and digital monitors 60 and 62. The analog monitor is used for the prescans and the digital for the automatic scanning.

As set forth under the SUMMARY, prior to the two, three or four scans during which the sample is evaluated, nonlevelness and sample thickness variations are accounted for and eliminated by pre-scans to insure that the received reflections or echoes are within their set time windows to provide a complete waveform for evaluation and cross-correlation to accurately obtain the time delay data used in calculating the velocity values. That is, during the nonlevelness and material thickness variation scans, the operator notes if the time delay of each echo received at each scan point is such that it is no longer centered within the oscilloscope time window. If a received echo is not centered within the time window on the scope, this is noted and the time window changed for each such echo received until the received echo time domain waveform is completely within the new time window set for it to insure that the complete time domain waveform is captured or gated completely within the new window. This time delay information at each scan point is inputted into the scan parameter file and recalled during the actual scanning during the material evaluation, to automatically adjust the time delay for the received echoes at each scan point so that each echo received during the scanning is centered within the time window set for it. This is very time consuming to do for each scan point. However, in the case of a sample having a thickness variation in the form of a uniform thickness variation from one edge to another, preliminary scans are performed along a single line in both the the x- and y-directions of the sample to provide slant correction factors. The slant correction factors are input into the computer scan parameter file so these variations are taken into account during the automatic scanning for the material evaluation. It is important that the echo at each scan point is centered in its time window, because the whole pulse or echo time domain waveform is needed to give the precise time delay between echoes for the cross-correlation which provides the velocity value. In doing this for a wedge shaped sample, prior to the automatic scan, the transducer scans along two straight lines over the sample, once in the the x-direction and once in the y-direction, during which an operator notes the echo received from the first and last scan points, starting from the first scan point which is generally at one corner of the area defined for scanning. The time difference from the sample end-to-end in each of the x- and y-directions of the first and last scan point is noted by the operator who then adjusts the time base for each echo if needed to insure that it is centered within the time frame set for it. This is done so that so that each echo received during the scans in which the material is being evaluated is centered (gated) within the oscilloscope time window set for it so that the received waveform is displayed with the maximum possible amplitude on the CRT and still have the complete waveform. This permits the maximum time resolution of individual echoes without losing any part of the time domain waveform which appears on the CRT screen as a function of voltage (amplitude) and time, wherein time is the x- axis and voltage or amplitude is the y- axis. It is important and forms an aspect of the invention that the complete waveform or pulse echo be captured or "gated" on the CRT screen in order to perform an accurate cross-correlation later on in the procedure of the process of the invention. The cross-correlation of echoes provides the precise time delay between received echoes or pulses which is required to calculate the velocity or speed of the ultrasound in the material evaluated which, in turn, provides the information to gray or color scale the velocity data into a digitized map of the material density. This slant correction procedure also allows an accurate evaluation to be made without the need for specialized leveling equipment. These x- and y-direction time window corrections are called slant correction factors and they are inputted into the scan parameter file in units of "nsec/pm" where (a) the number of nsec is the time extent from sample end-to-end that is required to keep the specific echo centered and is determined using the (a) time synthesizer to reposition echoes in time and (b) the number of µm is the distance traveled by the transducer for which this slant factor is determined. By way of an illustrative, but nonlimiting example, the first scan point (0,0) along the x- direction may have a B1 echo centered at a time=6.77 µsec, while the last scan point (40,0), may have B1 centered at time=7.14 µsec. If the x- direction scan line length is 40 mm, the x-direction slant correction factor is obtained from (7.14–6.77)/40 µsec/mm. It should be noted that slant correction factors can be negative as well as positive numbers. The location of the time window during scanning for the material evaluation is automatically adjusted via computer control by using the formula:

$$W_{DT}=T_I+[(X_{SC})(X_{SN})(X_{SI})+(Y_{SC})(Y_{SN})(Y_{SI})]$$

wherein $W_{DT}$ is the correct delay time window at a particular scan location, $T_I$ is the time delay at the the initial scan location, $X_{SC}$ and $Y_{SC}$ are the x- and y-direction slant correction factors, $X_{SN}$ and $Y_{SN}$ are the scan point numbers in the x- and y-directions, and $X_{SI}$ and $Y_{SI}$ are the x- and y-direction scan increments. With many samples it has been found that the slant correction factors turn out to be the same for the B1, B2 echoes and the slant correction factors for the M', M" echoes are the same. However, for some samples (e.g., thick samples), they may not be the same. In such cases a first x- and y-direction scan is made for the B1 echoes and a second x- and y-direction scan made for the B2 echoes. The same holds for the M' and M" echoes for which two separate scans are made in the x- and y-directions.

A scan parameter file is input into a computer which contains all of the information necessary to automatically scan the material sample being evaluated. This information includes a predefined and ordered array of scan points over which to run the scan. By way of an illustrative, but nonlimiting example, in an example of the method of the invention in which the material being evaluated was a monolithic ceramic wedge, the scan consisted of a 41 (X-direction) by 81 (y-direction) grid of measurements for a total of 3,200 scan points, with each measurement or scan point separated by 1 mm (x-) and y- scan increment). Information input into the scan parameter file (NOTHICK_ALLSHAPE1.DAT) includes the following:

```
C TITLE NOTHICK ALLSHAPE1.DAT
C ** SCAN INCREMENT (uM) IN X-DIRECTION IS:
1000.
C ** SCAN INCREMENT (uM) IN Y-DIRECTION IS:
1000.
C ** SCAN LENGTH (uM) IN X-DIRECTION IS:
40000.
C ** SCAN LENGTH (uM) IN Y-DIRECTION IS:
80000.
C ** X-DIRECTION SLANT CORRECTION FACTOR (nsec/uM) FOR B1 & B2 ECHOES IS:
–0.0055
C ** Y-DIRECTION SLANT CORRECTION FACTOR (nesec/uM) FOR REFLECTOR ECHOES IS:
–0.0055
C ** Y-DIRECTION SLANT CORRECTION FACTOR (nsec/uM) FOR B1 & B2 ECHOES IS:
–0.00175
C ** Y-DIRECTION SLANT CORRECTION FACTOR (nsec/uM) FOR REFLECTOR ECHOES IS
0.0
C ** TIME LOCATION (uSEC) OF B1 ECHO AT SCAN ORIGIN IS:
52.83
C ** TIME LOCATION (uSEC) OF B2 ECHO AT SCAN ORIGIN IS:
52.31
C ** TIME LOCATION (uSEC) OF REFLECTOR ECHO W/SAMPLE PRESENT AT SCAN LOCATION
IS:
69.46
C ** TIME LOCATION (uSEC) OF REFLECTOR ECHO W/O SAMPLE PRESENT AT SCAN LOCATION
IS:
72.48
C ** IMMERSION FLUID VELOCITY (cm/uSEC) IS:
0.148
C ** B2 PHASE-INVERTED WRT B1 (Y/N)?:
N
C ** M" PHASE INVERTED WRT M' (Y/N)?:
N
```

As set forth above, in the method of the invention, the transducer is activated so that the first front surface echo off the sample, the first two successive back surface echoes, and the first echo off the reflector plate are all seen in the oscilloscope display at the same time by adjusting the the time base to the appropriate time per division setting and adjusting the time synthesizer delay time. Viewing the first front surface echo off the sample enables the operator to know if the back surface echoes are also on the CRT screen. The unfocused transducer is positioned above the sample at a distance determined initially by the natural focal distance. When using an unfocused transducer a good initial starting height is approximately one to two inches above the sample. The reflector plate front surface echo may be low in amplitude compared to the sample back surface echoes, so that the the pulser-receiver gain/attenuation or vertical amplifier gain settings may have to be increased to see this echo. It is important not to confuse the echoes off the front surface of the reflector plate with the second set of echoes originating from the front and back surfaces of the sample. The second set of echoes originating from the front and back surface of the sample will always occur at twice the delay time where the first set of these echoes appears. For example, if the first set of echoes begins at 50 msec on the digital oscilloscope, the second set will begin at 100 msec. If using, for example, a three milimeter thick sample placed on 0.5" thick plastic supports on the reflector plate, the first reflector echo will occur at about 20 msec after the time where the first set of echoes originates and thus the reflector echo will be seen at about 70 msec in this illustration. Another way to note the reflector plate echo is to raise and lower the sample while noting the location of the stationary echo corresponding to the stationary reflector plate. It is essential to have reflector plate echoes that will not interfere with the second set of echoes originating from the front and back sample surfaces. Attention is next focused on the first back surface echo from the sample, B1. The echo is centered in the oscilloscope time window to obtaining maximum time resolution by adjusting the time base time per division and the time synthesizer delay. The synthesizer time is recorded and inputted into the scan parameter computer file. This procedure is repeated for the second back surface sample echo, B2, the first front surface echo off the reflector plate with the sample present, M' and the first echo off the reflector plate with the sample removed, M". The next step is to account for and eliminate any nonlevelness in the set-up and also sample thickness variations. This done at each scan point, except that in the case of uniform thickness variations in the sample, the slant correction factors outlined above are determined and input into the scan parameter file in the computer.

The scanning is then automatically performed through the remainder of the scanning points previously inputted into the scan parameter file in the computer using a program written in Fortran and IEX GPIB to perform the scanning and also to obtain maximum vertical voltage resolution of the received ultrasonic waveforms. Scanning is accomplished through the use of computer controlled x-, and y- microscanning tables used to reposition the sample in the x- or y-direction in a 1 mm increment (other increments may be used at the convenience and discretion of the practitioner) for the next measurement. The ultrasonic waveforms received are then digitized (512×512 pixel resolution) at each scan location and stored successively in the scan data file in the computer. Four separate ultrasonic scans are performed at each scan location. As set forth above, the echoes are B1 (first echo off sample back surface, obtained in first scan), B2 (second echo off sample back surface, obtained in second scan), M' (first echo off front surface of reflector plate with the sample present, obtained in third scan), and M" (first echo off front surface of reflector plate without the sample present, obtained in fourth scan). Each of the four echoes is obtained in a separate scan to obtain the maximum time resolution for each echo by setting, before each scan during the nonlevelness and material thickness variation procedure, the optimum time per division setting on the oscilloscope time base that allows maximum time resolution. The minimum number of scans for this thickness-elimination procedure is two, but the time per division setting for only two scans cannot be obtained in this case as the time per division setting would be fixed for all three echoes obtained in the first of the scans using this scan procedure.

The following is an algorithm of a scanning program which accounts for and eliminates the nonlevelness of the set-up and uniform thickness variation effects of the sample in the resulting ultrasonic image displayed on the video, the code for which is included in the Appendix.

1) Determine the scan lengths and scan increments in the x- and y-directions, time positions of echoes at scan origin, slant correction factors, and immersion fluid velocity.
2) Edit NOTHICK_ALLSHAPE1.DAT FILE, which is the scan parameter file, and input information from 1) above.
3) Start scanner fortran program on computer which automatically does the following:
    A) Initialize all GPIB instrumentation, which includes the time synthesizer, digitizer, time base, voltage amplifier, Klinger X, Y stages.
    B) Perform scan to digitize B1 echoes and store in file
        I) Digitize B1 at scan origin
            Adjust voltage base for echo with maximum amplitude in video/oscilloscope window
            Move Klinger tables under transducer in x- direction specified x- direction increment
            Time synthesizer moves to delay time position determined by B1, B2, slant correction factors. This results in echo in video being centered in the Tektronics analog video/oscilloscope display and subsequently digitized and stored.

$$\text{Time position} = T_0 + [(S_x)(N_x)(I_x) + (S_y)(N_y)(I_y)]$$

where $T_0$=correct delay time window at a particular scan location $S_x$=x- direction slant correction factor (nsec/μm)
            $N_x$=scan point number in x- direction
            $I_x$=x- direction scan increment (μm)
            $S_y$=y- direction slant correction factor (nsec/μm)
            $N_y$=scan point number in y- direction
            $I_y$=y- direction scan increment (μm)
        II) Repeat I) until one scan line in x- direction is completed.
        III) Increment transducer in y- direction specified y- direction increment and repeat I)–II).
        IV) Repeat I)–III) until y- scan length is traversed and scan is completed.
        V) Return Klinger tables to scan origin.
    C) Perform scan to digitize B2 echoes and store in file by repeating steps B(I–V)
    D) Perform scan to digitize reflector echoes with sample present and store in file by repeating steps B(I–V), but using reflector echo slant correction factor
    E) Remove sample. Perform scan to digitize reflector echoes without sample present and store in file by repeating steps B(I–V), but using reflector echo slant correction factor
4) Start velocity calculation Fortran program on computer to produce a file of velocities at each scan location by performing the cross-correlation algorithm.

5) Start image formation Fortran program on computer which results in a file of values between 0 and 255 which scale directly with the velocity values.

6) Start image display program which brings grey scale level image up on video.

Before initiating the scanning procedure, the temperature of the water or other immersion fluid is measured. If the fluid is water, published tables or graphs of temperature and velocity can be used to determine the velocity of the ultrasound in the constant temperature water bath. If the immersion liquid is a liquid other than water, or if a more precise temperature than that available in published graphs and tables is desired, the velocity of the ultrasound in the liquid is determined by recording the times ($T_P$) where ultrasonic peaks occur for two different vertical positions (Z1 and Z2) of the transducer above the reflector plate. The velocity, V, is then determined from $$V=(Z1-Z2)/(T_P1-T_P2)$$

The phase relationships of (a) B1 compared to B2 and also (2) the reflector front surface echo with the sample present (M') compared to that without the sample present (M") are examined. These phase relationships are important for the computation of the velocity image of the scanned sample. The quantity $2\tau$ is obtained by cross-correlating echoes B1 and B2 which is defined as the precise time delay between the B1 and B2 echoes. If B1 and B2 are phase inverted with respect to each other, the time occurrence of the minimum in the cross-correlation function is used to obtain $2\tau$. If M' and M" are phase inverted with respect to each other, the time occurrence of the minimum in the cross-correlation function is used to obtain $\Delta t$. Otherwise, at the time occurence of the maximum in the cross-correlation function is used.

Figure 3A:
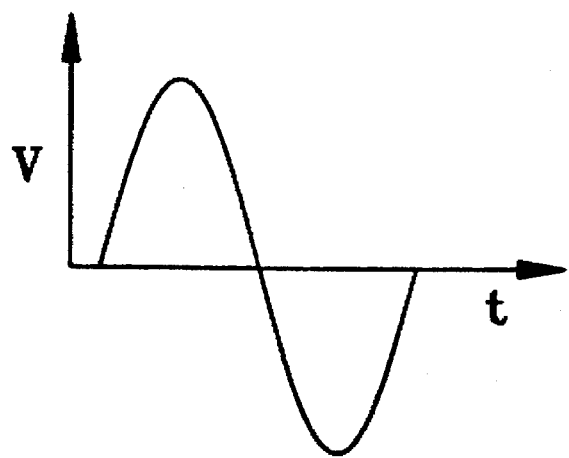
FIGS. 3(a) and 3(b) graphically illustrate respective first and second sample back surface echoes in which the second is inverted with respect to the first.
Figure 3B:
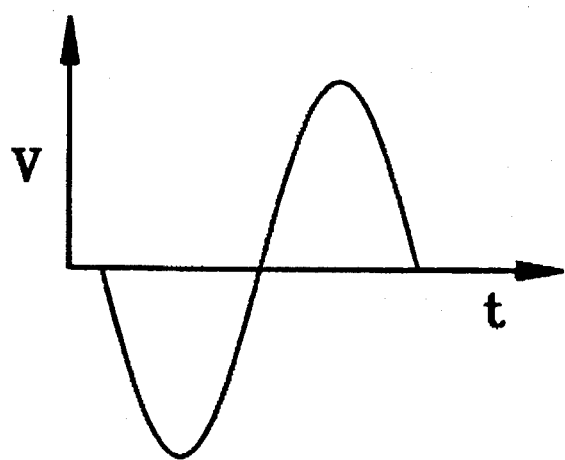

FIGS. 3(a) and 3(b) graphically illustrate the case in which B2 is phase inverted with respect to B1. The same holds for M' and M". Phase relationships generally remain the same throughout the scan, unless significant discrete microstructural defects are encountered by the ultrasonic wave.

After the scan has been completed and all the received echoes have been digitized and stored in the scan data file in the computer, they are recalled from the data file to perform the velocity image calculation for each scan location. In performing this cross-correlation, an overlap method is used by the computer based on a cross-correlation program using Fast Fourier transforms published in pages 415 and 416 (Correlation and Autocorrolation Using the FFT) in the book *Numerical Recipes—The Art of Scientific Computing*, by Press, et. al., 1988 Edition, Cambridge Univ. Press.. The Fortran program used is in the Appendix. Echoes M' and M" are also cross-correlated to obtain $\Delta t$ where where M' is the echo reflected off the reflector plate front surface with the sample present, M" is the echo reflected off the reflector plate front surface without the sample present, and $\Delta t$ is the time delay between them. If M' and M" are phase inverted with respect to each other, the time occurrence of the minimum in the cross-correlation function is used to obtain $\Delta t$. Otherwise the time occurence of the maximum in the cross-correlation function is used. The velocity, V, at each scan location is then calculated from the equation referred to above. The velocity value for each scan location is sequentially stored in the computer. After the scan is completed the velocity values are scaled on a gray or color scale with a value directly proportional to the velocity values, with the highest and lowest scale values corresponding to the highest and lowest velocity values.

The invention will be further understood with reference to the example below.

EXAMPLE

In this example, a sample of silicon nitride ceramic was evaluated using the thickness based velocity image method disclosed in the NASA Technical Memorandum TP 3377 referred to under Background. This method is based on a velocity, cross-correlation ultrasonic imaging method without the pre-scan to account for and eliminate nonlevelness in the set-up and sample thickness variations. In this method, only the first two sample back surface echoes are captured and evaluated. The silicon nitride ceramic was 3.5 mm thick with a uniform 300 micron thickness gradient. Very coarse time scaling was used so that the B1 and B2 echoes stayed in the time window while the sample thickness changed as the scan proceeded.

The same silicon nitride ceramic sample was also scanned and velocity imaged on a grey scale according to the method of the invention which included the prescans to eliminate set-up and sample thickness variations and which also captured and cross-corrolated both the first two successive sample back surface echoes and the two different reflector front surface echoes.

In both cases, the 20 MHz broad band transducer was used, the immersion liquid was water and the back plate was tungsten as set forth above.

Figure 5A:
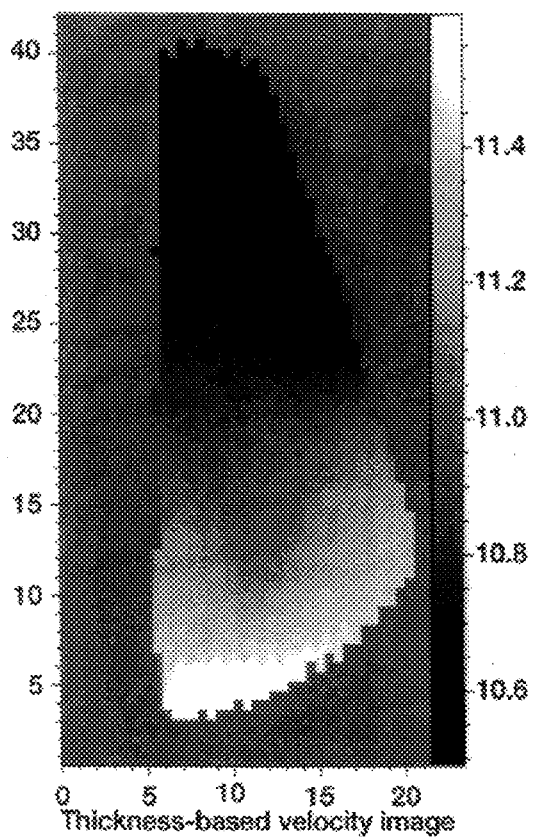
FIGS. 5(a) and 5(b) are photographs of video grey scale displays of a thickness based ultrasonic velocity image of a ceramic according to the prior art method and the method of the invention, respectively.
Figure 5B:
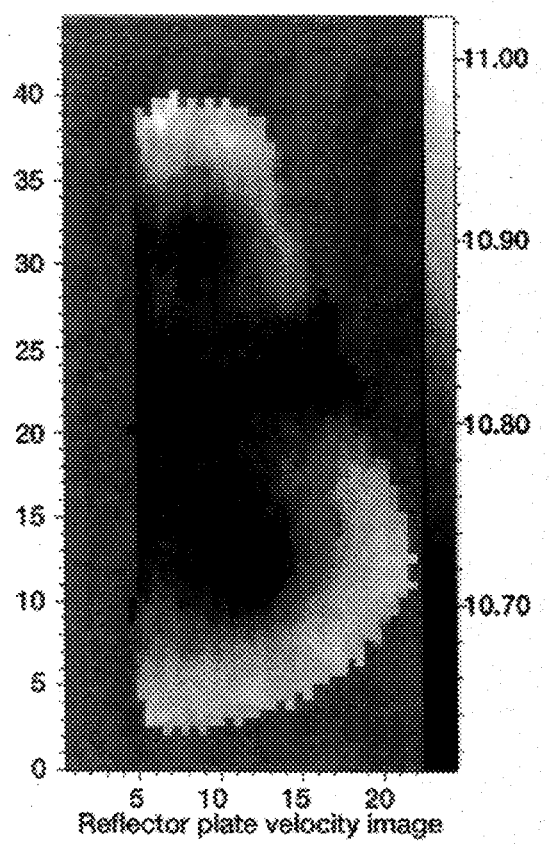

FIGS. 5(a) and 5(b) are photographs of video grey scale displays of the thickness based ultrasonic velocity image of a ceramic according to the prior art method, and an image according to the method of the invention which included the prescans, respectively. Referring to FIG. 5(a), it is seen that the top defect is masked due to that part of the sample being thicker than the bottom part. Also, the defect near the bottom is not too discernable and the lower portion is very light due to it being thinner. In marked contrast and as shown in FIG. 5(b), the method of the invention clearly and correctly illustrates the defect areas, including resolution of the upper defect and an overall porosity gradient in the sample. It is believed that this demonstrates the efficacy and improvement to the art of the invention.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

Docket No. NASA LEW-16,257-1
Serial No. 08/546,972

Patent

Sent by Express Mail to Addressee under
Mailing Label Number:
EH462213576US on October 10, 1996

SUBSTITUTE
APPENDIX       *Kent N Stone*

APPENDIX

A

```
C
C    nothick_SCAN.FOR --- 4 SCAN METHOD
C
C    Scan and data aquisition for the modified ultrasonic Immersion scanner
C
C        by Don J.Roth
C
C  PLEASE USE CLNEW.COM TO COMPILE & LINK
C
C                    Latest Update 20-sep-94
C
       integer*4  SCANSTEP,INDXSTEP
       integer*4  SCANAXIS, INDXAXIS, ZSTEP
       INTEGER*4  I17
       character  VOLANS*1,TSCHEME*1,UOLANS*1
       CHARACTER  LOOPANS*1,SHAPEANS*1,ZIGANS*1,FLAG*1
       character  TBUF*8,SCHEME*1,FILENAME*34,SCANMODE*1
       real       DELAY(0:4),VOLTSET(0:4),MAXVALF,MAXVALT,VOL(4)
       real       slant1,slant2,slant3,slant4
       integer*2  NSCAN, NINDX,PLACE,ZIGCOUNT,JXXX,SCANKNT
       integer*2  A(512),NAVE,CHECKP,WWFLAG
       INTEGER*2      I15,I16,I26,I27,MAXFS1P,MAXFS1PT
       INTEGER*2      I36,I37,I46,I47
       INTEGER*2      LOOPTHRU_H,LOOPTHRU_S,LLL,IT,I,J,JJ,II
       BYTE  WRK0(80)
     common /IBLK/  WRK0,BUFFER
     common /SBLK/ A, DELAY,VOLTSET,MAI
       data       CHECKP/0/ZIGCOUNT/1/
       DATA       I6/1/,I15/1/,I16/1/,I17/1/,PLACE/0/
       data       I26/1/,I27/1/,I36/1/,I37/1/,I46/1/,I47/1/
10010  format( A )
10012  format( A2 )
10020  format( I )
10030  format( F )
       OPEN( unit=8, file='TXA1:', status='NEW' )
       CALL ENTERPARAM( SCANSTEP,INDXSTEP, NSCAN,NINDX,NAVE,VOLTAGEL
     1  ,VOLTAGEU,VOLTAGE_MAX,SHAPEANS,LOOPANS,LOOPTHRU_H,LOOPTHRU_S,
     1  ZIGANS,SCHEME,TSCHEME,UZEROO,FILENAME,I15,SCANMODE,SLANT1,SLANT2
     1 ,SLANT3,SLANT4)

4328   SCANAXIS = 1
       INDXAXIS = 2
       ZSTEP = 10

CALL STRTGPIB
       DO 1800 IADDR= 5,1,-1
1800   CALL INITINSTR( IADDR )
C
C  Setup of 7912: begin with V/D =.5, then automatically find
C            the best intensity and Digitize Defects
C
C      NOTE:MAY NEED TO CHANGE THIS V/D TO START
C
2000   CALL TEKGTL
C*************************************************************
```

```
10      FORMAT (3F)
        READ (10,65403) DELAY1    !NOTHICK - STARTING 1ST BACK SURFACE ECHO
                                              WINDOW TIME
        READ (10,65403) DELAY2    !NOTHICK - STARTING 2ND BACK SURFACE ECHO
                                              WINDOW TIME
        READ (10,65403) DELAY3    !NOTHICK - STARTING (W/SAMPLE) REFLECTOR ECHO
                                              WINDOW TIME
        READ (10,65403) DELAY4    !NOTHICK - STARTING (WO/SAMPLE) REFLECTOR
                                              ECHO WINDOW TIME
        READ (10,65402) VOLANS
        READ (10,65403) VOL(1)
        READ (10,65403) VOL(2)
        READ (10,65403) VOL(3)
        READ (10,65402) UOLANS
        READ (10,65403) VOL(4)
65402   FORMAT (A)
65403   FORMAT (F)
51      FORMAT(A32)
52      FORMAT(A2)
53      FORMAT(A4)
54      FORMAT(A2)
        TYPE *,'DELAY TIMES (B1,B2,RS,RNS)'
        TYPE *,'DELAY1=',DELAY1
        TYPE *,'DELAY2=',DELAY2
        TYPE *,'DELAY3=',DELAY3
        TYPE *,'DELAY4=',DELAY4
        TYPE *,' '
        CLOSE (10)
        DELAY(1)=DELAY1/(1.*10.**6.)
        DELAY(2)=DELAY2/(1.*10.**6.)
        DELAY(3)=DELAY3/(1.*10.**6.)
        DELAY(4)=DELAY4/(1.*10.**6.)
        TYPE *,' '
        TYPE *,DELAY
        TYPE *,' '
C*************************************************************
        CALL INITINSTR(0)
        CALL SETVOLTDIV(0.5)
        CALL TEKGTL
        CALL GETMAI(MAI)
        CALL TEKGTL
        CALL PUTTIME(DELAY(1))
        CALL TEKGTL
        CALL GETBESTMAI( MAI )
        CALL DIGDEF
C
C       !Preliminary Digitizations to get Watch level and Timeset (Time/div)
C
        CALL TEKGTL
        CALL AUTOSETVOLTS( MAI, VOLTSET(1),NUMINT )
C       TYPE *,'AUTOSET VOLTS'
        IF( VOLTSET(1).EQ. 999. )THEN
            TYPE *,'DIGITIZER IS SCREWED UP'
            GOTO 2000
        ENDIF
```

```
      CALL GETGRID( TIMESET, X )
      CALL GETSA( NAVE,MAI,A )
      CALL TEKGTL

TYPE *,'Timeset=',TIMESET,'    Delay=',DELAY(1),
    +  '  Voltset=',VOLTSET(1)

TYPE *,'I16= ',I16,' I17= ',I17
C****************************************************
      WRITE(16,rec=I16,fmt=53)TIMESET
      I16=I16+1

C
C  Get WATCH - standard ground level
C
      TYPE *,' '
      TYPE *,' '
      TYPE *,' '
      TYPE *,' '
      W = A(1)/NAVE
      WATCH = W - 100.
      WRITE( 8,12030 )WATCH
      TYPE *,' '
      TYPE *,' '
      TYPE *,' '
      TYPE *,' '
12030 format(' Minimum acceptable ground level =',F )

C     SCANSTEP = 1000*SCANSTEP
C     INDXSTEP = 1000*INDXSTEP
      CALL SETXYZ( SCANSTEP, INDXSTEP, ZSTEP )
      WRITE( 5,12140 )
12140 format( ///' ### S C A N N I N G ###'// )
      IDIR=1

WWFLAG=0 do 2600 noth_I = 1,4      ! nothickness mod
      if (noth_I.ge.2)then
      CALL MOVORGXY (ZIGANS,SCANAXIS,NSCAN,INDXAXIS,NINDX)
      REWIND(12) ! .DATHS FILE
      IF (ZIGANS.EQ.'Y')ZIGCOUNT=1
      ENDIF IF (NOTH_I.EQ.4)THEN
      type *,'                    '
      type *,'                    '
      type *,'                    '
      type *,' ******* Finished w/ Sample Scan ************'
      type *,' *** Remove Sample from tray & Hit <RET> to perform water scan'
      type *,'                    '
      type *,'                    '
      type *,'                    '
      Read (5,10020) IO
```

```
            ENDIF

DO 2400 I=1,NINDX         ! Outer loop over index
            DO 2200 J=1,NSCAN         !   Inner loop over scan IF (NOTH_I.ge.2)THEN
            READ(12)JJ,II,FLAG,SCANKNT  !READ WHETHER 'H' OR 'S' type *,' '
            type *,' '
            type *,' '
            type *,'second time around for',jj,ii
            type *,'FLAG =',FLAG
            type *,' '
            type *,' '

ENDIF

IF ((SCANMODE.EQ.'P'.OR.SCANMODE.EQ.'L').AND.I.GT.1)GOTO 2400 !MOD FOR LINE / POINT
SCAN
            IF (NOTH_I.EQ.1)TYPE *,'I= ',I,' AND J=',J
            PLACE=PLACE+1
            WRITE( 8,13000 )J,I,PLACE           !
C*****************************************************************C

IF (SHAPEANS.EQ.'N')THEN
            CALL TAKEDATA_O(FILENAME,VOLANS,UOLANS,VOL,I16,I17,I26,I27,
     1      I36,I37,I46,I47,NAVE,WATCH,I,J,noth_I,SLANT1,
     1      SLANT2,SLANT3,SLANT4,SCANSTEP,INDXSTEP,ZIGANS,NSCAN)
            ELSEIF (SHAPEANS.EQ.'Y')THEN
            IF (NOTH_I.EQ.2.AND.FLAG.EQ.'H')GOTO 3429
            CALL TAKEDATA(PLACE,SCHEME,TSCHEME,VOLANS,VOL,UZEROO,FILENAME,
     1      UOLANS,I26,I27,NOTH_I,I36,I37,I46,I47,
     1      SLANT1,SLANT2,SLANT3,SLANT4,SCANSTEP,INDXSTEP,ZIGANS,NSCAN,
     1      RCMAX,MAXFS1P,MAXVALF,RF1,RF2,MAXFS1PT,MAXVALT,RT1,RT2,I16,I17,
     1      NAVE,WATCH,J,I,I15,IT)
            ENDIF
C*****************************************************************C 3429        CONTINUE
            IF (NOTH_I.EQ.1.AND.IT.LT.4)THEN
            TYPE *,'I16= ',I16,' I17= ',I17
            ELSEIF (NOTH_I.EQ.1.AND.IT.EQ.4)THEN
            TYPE *,'I46= ',I46,' I47= ',I47
            ENDIF

IF( J.EQ.NSCAN )GOTO 2200       !

IF (LOOPANS.EQ.'N')GOTO 22001 !DON'T PICK UP XDUCER EACH TIME

IF (NOTH_I.EQ.1)TYPE *,'IT=',IT
            IF (NOTH_I.EQ.1)TYPE *,' '
```

```
        IF (NOTH_I.EQ.1)TYPE *,' '
        IF (NOTH_I.EQ.1)TYPE *,'VOLANS (WRT "ON SAMPLE")= ',VOLANS
        IF (NOTH_I.EQ.1)TYPE *,'UOLANS (WRT "NOT ON SAMPLE)= ',UOLANS
        IF (NOTH_I.EQ.1)TYPE *,' '

C************ MOD FOR ZIGZAG SCAN *****************************C
22001   IF (ZIGANS.EQ.'Y'.AND.ZIGCOUNT.EQ.0)THEN  !ZIGZAG SCAN
        IF (SCANMODE.EQ.'P')GOTO 12306  !FOR POINT MEASURE, DON'T MOVE X-AXIS
        CALL MOVXYZ(SCANAXIS,-1)  ! MOVE X-AXIS BACKWARD
        ELSEIF (ZIGANS.EQ.'Y'.AND.ZIGCOUNT.EQ.1)THEN
        IF (SCANMODE.EQ.'P')GOTO 12306  !FOR POINT MEASURE, DON'T MOVE X-AXIS
        CALL MOVXYZ(SCANAXIS,1)  !MOVE X-AXIS FORWARD
        ENDIF
12306   CONTINUE
        CALL WAIT2(1000)  !ADD DELAY SO THAT DATA IS NOT TAKEN BEFORE
C                         KLINGER STAGES STOP MOVING
        CALL WAIT2(1000)
        CALL WAIT2(1000)
        CALL WAIT2(1000)
        CALL WAIT2(1000)
        CALL WAIT2(1000)
        CALL WAIT2(1000)
        CALL WAIT2(1000)
        CALL WAIT2(1000)
        CALL WAIT2(1000)
        CALL WAIT2(1000)
        CALL WAIT2(1000)
        CALL WAIT2(1000)
        IF (ZIGANS.EQ.'Y')GOTO 12305
C*********************************C
        IF (SCANMODE.EQ.'P')GOTO 2402  !FOR POINT MEASURE, DON'T MOVE X-AXIS

2402    CONTINUE

IF (LOOPANS.EQ.'N')GOTO 2200

12305   CONTINUE    !NOTHICK

2200    CONTINUE

!   ---

IF( I.EQ.NINDX )GOTO 2400    !

C  !FOR LINE SCAN OR POINT MEASURE, DON'T MOVE Y-AXIS

IF (SCANMODE.EQ.'P'.OR.SCANMODE.EQ.'L')GOTO 2401
        CALL MOVXYZ( INDXAXIS, 1 )       !  Move CALL WAIT2(1000)
        CALL WAIT2(1000)
        CALL WAIT2(1000)
        CALL WAIT2(1000)
```

```
        CALL WAIT2(1000)
        CALL WAIT2(1000)
        CALL WAIT2(1000)
        CALL WAIT2(1000)
        CALL WAIT2(1000)
        CALL WAIT2(1000)
        CALL WAIT2(1000)
        CALL WAIT2(1000)
        CALL WAIT2(1000)

2401    NTOGO = NINDX-I            !

IF (ZIGANS.EQ.'N')THEN !NORMAL SCAN
        CALL MOVORG(SCANAXIS,NSCAN,VOLTAGEL,VOLTAGEU,
    1        LOOPTHRU_H)            !Move back to the X origin
C***************** MOD FOR ZIGZAG SCAN ******************C
        ELSEIF (ZIGANS.EQ.'Y')THEN
        IF (ZIGCOUNT.EQ.1)THEN
        ZIGCOUNT=0
        GOTO 15021
        ELSEIF(ZIGCOUNT.EQ.0)THEN
        ZIGCOUNT=1
        ENDIF
        ENDIF
C*********************************C
15021   CONTINUE     !NOTHICK 2400    CONTINUE                   ! ---
2600    continue
        CALL TIME(TBUF)
        WRITE( 8,13100 )TBUF
        CLOSE( 8 )
        CLOSE( 6 )
        CLOSE(14)
        JXXX=I-1   !!!!!!!!!!!!!!!!! Y-LOCATION
        IF (SCANMODE.EQ.'L'.OR.SCANMODE.EQ.'P')JXXX=1  !MOD FOR LINE SCAN & POINT
MEASURE
        WRITE(15,REC=I15,FMT=52)JXXX
        I15=I15+1
C       ENDIF
        STOP
13000   format(' ',I3,I3,I5)
13100   format(' ',A8 )
        end SUBROUTINE TAKEDATA_O(FILENAME,VOLANS,UOLANS,VOL,I16,I17,I26,I27,
    1        I36,I37,I46,I47,NAVE,WATCH,I,J,noth_I,SLANT1,
    1        SLANT2,SLANT3,SLANT4,SCANSTEP,INDXSTEP,ZIGANS,NSCAN)
        integer*2 A(512), WFLAG,I16,I26,WWFLAG,I,J,ILOCX,NSCAN,ILOCY,I36,I46
        INTEGER*4    I17SUB,I17,I27,SCANSTEP,INDXSTEP
        INTEGER*4 I27SUB,I37SUB,I47SUB
```

```
      real   DELAY(0:4), VOLTSET(0:4),VOLTAGE(4),VOL(4),SLANT1,SLANT2,SLANT
      REAL   SLANT3,SLANT4
      character DAY*9, TIM*9,VOLANS*1,UOLANS*1,C1*80,FILENAME*34,ZIGANS*1
      common  /SBLK/ A, DELAY, VOLTSET, MA1
C
      DATA I14/0/
C
         if (noth_I.eq.1)then
            OPEN( unit=14, file='[ROTH.MENU]DONSCAN_INTERP.LOG',
     +            status='NEW',ACCESS='SEQUENTIAL',
     +            FORM='UNFORMATTED')
         endif
C
51    FORMAT(A32)
52    FORMAT(A2)
53    FORMAT(A4)
54    FORMAT(A2)
      WFLAG = 0
10600 format(' ',I15 )

if (noth_I.eq.1)then
      IX=1
      IY=1
      elseif (noth_I.eq.2)THEN
      IX=2
      IY=2
      elseif (noth_I.eq.3)THEN
      IX=3
      IY=3
      elseif (noth_I.eq.4)THEN
      IX=4
      IY=4
      ENDIF

DO 600 IT = IX,IY

IF (IT.EQ.1.OR.IT.EQ.2)THEN
      SLANTX=SLANT1
      SLANTY=SLANT3
      ELSEIF (IT.EQ.3.OR.IT.EQ.4)THEN
      SLANTXR=SLANT2
      SLANTYR=SLANT4
      ENDIF

C ***** MODIFICATION FOR ZIGZAG SCAN ****************************C
      IF (ZIGANS.EQ.'Y')THEN
      IF (I.EQ.2.OR.I.EQ.4.OR.I.EQ.6.OR.I.EQ.8.OR.I.EQ.10
     1 .OR.I.EQ.12.OR.I.EQ.14.OR.I.EQ.16.OR.I.EQ.18.OR.I.
     1 EQ.20.OR.I.EQ.22.OR.I.EQ.24.OR.I.EQ.26.OR.I.EQ.28.OR.
     1 I.EQ.30.OR.I.EQ.32.OR.I.EQ.34.OR.I.EQ.36.OR.I.EQ.38.
     1 OR.I.EQ.40.OR.I.EQ.42.OR.I.EQ.44.OR.I.EQ.46.OR.I.EQ.
     1 48.OR.I.EQ.50.OR.I.EQ.52.OR.I.EQ.54.OR.I.EQ.56.OR.
     1 I.EQ.58.OR.I.EQ.60.OR.I.EQ.62.OR.I.EQ.64.OR.I.EQ.66
     1 .OR.I.EQ.68.OR.I.EQ.70.OR.I.EQ.72.OR.I.EQ.74.OR.I.
     1 EQ.76.OR.I.EQ.78.OR.I.EQ.80.OR.I.EQ.82.OR.I.EQ.84.OR
```

```
    1 .I.EQ.86.OR.I.EQ.88.OR.I.EQ.90.OR.I.EQ.92.OR.I.
    1 EQ.94.OR.I.EQ.96.OR.I.EQ.98.OR.I.EQ.100)THEN
    ILOCX=NSCAN-J  !FOR ZIGZAG SCAN, REVERSE BACK FOR DISPLAY
        ELSE
        ILOCX=J-1
        ENDIF
        elseif(zigans.eq.'N')then !george wood addition
        ILOCX=J-1  !George Wood addition
        ENDIF
        ILOCY=I-1

IF (IT.EQ.1.OR.IT.EQ.2)THEN   !CORRECT DELAY WINDOW FOR NONLEVELNESS
        DELAY_CORR=DELAY(IT)+(SLANTX*ILOCX*SCANSTEP)+(SLANTY*ILOCY*INDXSTEP)
        ELSEIF (IT.EQ.3.OR.IT.EQ.4)THEN
        DELAY_CORR=DELAY(IT)+(SLANTXR*ILOCX*SCANSTEP)+(SLANTYR*ILOCY*INDXSTEP)
        ENDIF

TYPE *,' '
        TYPE *,' '
        TYPE *,' '
        TYPE *,'J=',J,' DELAY(',IT,')= ',DELAY(IT)
        TYPE *,'DELAY_CORR= ',DELAY_CORR
        TYPE *,' '
        TYPE *,' '
        TYPE *,' '
        CALL PUTTIME( DELAY_CORR )         !  Set delay

100     CONTINUE

IF ((IT.NE.4.AND.VOLANS.EQ.'U').OR.(IT.EQ.4.AND.UOLANS.EQ.'U'))THEN
C                                           !!!! USER-DEFINED VOLTAGE SETTINGS
        VOLTS=VOL(IT)
        CALL SETVOLTDIV(VOLTS)
        GOTO 1132
        ENDIF

CALL AUTOSETVOLTS( MAI,VOLTS,NUMINT )         ! Set V/D
1132    IF((VOLTS.GT.1.0).OR.(VOLTS.LT.0.01))THEN
        WRITE(5,1131)VOLTS
1131    FORMAT('+','BAD VOLTAGE SETTING',E10.5)
        CALL TEKRESET(MAI)
        GOTO 100
        ENDIF

CALL GETSA(NAVE,MAI,A)    !  Get waveform

WATCH1 = A(1)/ NAVE       !  Make sure its acceptable
        TYPE *,' '
        TYPE *,' '
        TYPE *,' '
        WRITE(5,1133)WATCH1,WATCH
1133    FORMAT('+','CURRENT WATCH LEVEL IS',F10.5,'MIN =',F10.5)
        TYPE *,' '
        TYPE *,' '
```

```
              TYPE *,' '

IF ((IT.NE.4.AND.VOLANS.EQ.'U').OR.(IT.EQ.4.AND.UOLANS.EQ.'U'))GOTO 56732
C                                       !!!! USER-DEFINED VOLTAGE SETTINGS

C             IF (VOLANS.EQ.'U')GOTO 56732 !! SKIP WATCH

IF( WATCH1.LT.WATCH )THEN
                     WWFLAG = WWFLAG+1
                     IF (WWFLAG.EQ.1)THEN
                     OPEN( unit=88, file='[ROTH.MENU]DONSCAN.LOG',
       +                    status='NEW' )
                     ENDIF
                     WRITE( 5,10200 )
                     CALL TIME(TIM)
                     CALL DATE(DAY)
              TYPE *,' '
              TYPE *,' '
              TYPE *,' '
                     type *,'watch1=',watch1,' < watch=',watch
              TYPE *,' '
              TYPE *,' '
              TYPE *,' '
              TYPE *,' '
                     WRITE( 88,10201 )FILENAME,DAY,TIM,J,I,CI
10201                format(' ',A,' ',A,' X= ',I3,' Y= ',I3,'MAY LEAD TO BAD PROPERTY VALUE' )
10200                format('   WAVEFORM BELOW "WATCH",MAY LEAD TO BAD PROPERTY VALUE')
C                    GOTO 100
                     ENDIF C*************************************************************
56732         CONTINUE IF (noth_I.eq.1)then
  500         WRITE(16,REC=I16,FMT=53)DELAY_CORR
              I16=I16+1
              WRITE(16,REC=I16,FMT=53)VOLTS
              I16=I16+1
C
              DO 54321 IJI=1,512
              I17SUB=((I17-1)*512)+IJI
54321         WRITE(17,REC=I17SUB,FMT=54) A(IJI)
              I17=I17+1 elseif (noth_I.eq.2)then

5500         WRITE(26,REC=I26,FMT=53)DELAY_CORR
              I26=I26+1
              WRITE(26,REC=I26,FMT=53)VOLTS
              I26=I26+1
C
              DO 54329 IJI=1,512
              I27SUB=((I27-1)*512)+IJI
54329         WRITE(27,REC=I27SUB,FMT=54) A(IJI)
```

```
            I27=I27+1 elseif (noth_1.eq.3)then

5800    WRITE(36,REC=I36,FMT=53)DELAY_CORR
         I36=I36+1
         WRITE(36,REC=I36,FMT=53)VOLTS
         I36=I36+1
C
         DO 58329 IJI=1,512
         I37SUB=((I37-1)*512)+IJI
 58329   WRITE(37,REC=I37SUB,FMT=54) A(IJI)
         I37=I37+1 elseif (noth_1.eq.4)then

5900    WRITE(46,REC=I46,FMT=53)DELAY_CORR
         I46=I46+1
         WRITE(46,REC=I46,FMT=53)VOLTS
         I46=I46+1
C
         DO 59329 IJI=1,512
         I47SUB=((I47-1)*512)+IJI
 59329   WRITE(47,REC=I47SUB,FMT=54) A(IJI)
         I47=I47+1 endif

C************************************************************C
         IF (IT.EQ.1)VOLTAGE(1)=VOLTS
         IF (IT.EQ.2)VOLTAGE(2)=VOLTS
         IF (IT.EQ.3)VOLTAGE(3)=VOLTS
         IF (IT.EQ.4)VOLTAGE(4)=VOLTS
C************************************************************C
 600     CONTINUE
C************************************************************C
         IF (I.EQ.0.AND.J.EQ.0) GOTO 20000  !SKIP NEXT STEP (NOISE MEASURE)
C        CHECK FOR ERROR IN FS2 VOLTSET
C
c        IF (VOLTAGE(1).EQ..01) THEN
c        WRITE (14) I,J,' VOLT FOR FS2=',VOLTAGE(1),
c   +    '#INT.PO.=',NUMINT
C        GOTO 100
c        ENDIF
C
C        CHECK FOR ERROR IN B1 VOLTSET
C
c        IF (VOLTAGE(1).LT.VOLTAGE(2)) THEN
c        WRITE (14) I,J,' VOLT FOR B1=',VOLTAGE(1),
c   +    '#INT.PO.=',NUMINT
C        GOTO 100
c        ENDIF
 7       FORMAT (A4)
C************************************************************C
 20000   CONTINUE
```

```
      RETURN
   end
C
```

```
      SUBROUTINE TAKEDATA(PLACE,SCHEME,TSCHEME,VOLANS,VOL,UZEROO,FILENAME,
 1    UOLANS,I26,I27,NOTH_I,I36,I37,I46,I47,
 1    SLANT1,SLANT2,SLANT3,SLANT4,SCANSTEP,INDXSTEP,ZIGANS,NSCAN,
 1    RCMAX,MAXFS1P,MAXVALF,RF1,RF2,MAXFS1PT,MAXVALT,RT1,RT2,I16,
 1    I17,NAVE,WATCH,J,I,I15,IT)

integer*2 A11(512),I26,I,J,ILOCX,NSCAN,WFLAG,I16,MAXFS1PT,PLACE
      INTEGER*2 WATCH_COUNT,IIIT,ILOCY,I36,I46
      INTEGER*2 MAXFS1P,NAVE,A(512),IT,SCANKNT
      INTEGER*4 I17SUB,I17,ISTAT,I27,SCANSTEP,INDXSTEP,I37,I47
      INTEGER*4 I27SUB,I37SUB,I47SUB
      REAL*4    ASPECF1(1024),PHASE(1024),MAXVALF,MAXVALT,VOL(3),SLANT3,SLANT4
      real*4    DELAY(0:4),VOLTSET(0:4),VOLTAGE(4),SLANT,SLANT1,SLANT2,F1(512)
      COMPLEX CF1(1024),CSPEC(1024)
      character SCHEME*1,FLAG*1,FILENAME*34,UOLANS*1,ZIGANS*1
      CHARACTER VOLANS*1,TSCHEME*1
      common    /SBLK/ A, DELAY, VOLTSET, MA1
C
      DATA I14/0/,IIIT/0/
C
      IF (NOTH_I.EQ.1)THEN
         OPEN( unit=14, file='[ROTH.MENU]DONSCAN_INTERP.LOG',
      +        status='NEW',ACCESS='SEQUENTIAL',
      +        FORM='UNFORMATTED')
      ENDIF
C
51    FORMAT(A32)
52    FORMAT(A2)
53    FORMAT(A4)
54    FORMAT(A2)
      WFLAG = 0
C     WATCH_COUNT=0
10600 format(' ',I15 )

IF (noth_I.eq.1.and.PLACE.EQ.1)THEN
      OPEN( unit=12, file=FILENAME//'HS', status='NEW',
      +     form='UNFORMATTED',ORGANIZATION='SEQUENTIAL' )
      SCANKNT=0
      ENDIF if (noth_I.eq.1)then
      IX=1
      IY=1
      elseif (noth_I.eq.2)THEN
      IX=2
      IY=2
      elseif (noth_I.eq.3)THEN
      IX=3
      IY=3
      elseif (noth_I.eq.4)THEN
      IX=4
      IY=4
      ENDIF
```

```
10386   DO 600 IT = IX,IY

C ***** MODIFICATION FOR ZIGZAG SCAN ***************************C
        IF (ZIGANS.EQ.'Y')THEN
        IF (I.EQ.2.OR.I.EQ.4.OR.I.EQ.6.OR.I.EQ.8.OR.I.EQ.10
     1 .OR.I.EQ.12.OR.I.EQ.14.OR.I.EQ.16.OR.I.EQ.18.OR.I.
     1 EQ.20.OR.I.EQ.22.OR.I.EQ.24.OR.I.EQ.26.OR.I.EQ.28.OR.
     1 I.EQ.30.OR.I.EQ.32.OR.I.EQ.34.OR.I.EQ.36.OR.I.EQ.38.
     1 OR.I.EQ.40.OR.I.EQ.42.OR.I.EQ.44.OR.I.EQ.46.OR.I.EQ.
     1 48.OR.I.EQ.50.OR.I.EQ.52.OR.I.EQ.54.OR.I.EQ.56.OR.
     1 I.EQ.58.OR.I.EQ.60.OR.I.EQ.62.OR.I.EQ.64.OR.I.EQ.66
     1 .OR.I.EQ.68.OR.I.EQ.70.OR.I.EQ.72.OR.I.EQ.74.OR.I.
     1 EQ.76.OR.I.EQ.78.OR.I.EQ.80.OR.I.EQ.82.OR.I.EQ.84.OR
     1 .I.EQ.86.OR.I.EQ.88.OR.I.EQ.90.OR.I.EQ.92.OR.I.
     1 EQ.94.OR.I.EQ.96.OR.I.EQ.98.OR.I.EQ.100)THEN
        ILOCX=NSCAN-J  !FOR ZIGZAG SCAN, REVERSE BACK FOR DISPLAY
        ELSE
        ILOCX=J-1
        ENDIF
        elseif(zigans.eq.'N')then !george wood addition
        ILOCX=J-1  !George Wood addition
        ENDIF
        ILOCY=I-1

IF (IT.EQ.1.OR.IT.EQ.2)THEN
        SLANTX=SLANT1
        SLANTY=SLANT3
        ELSEIF (IT.EQ.3.OR.IT.EQ.4)THEN
        SLANTXR=SLANT2
        SLANTYR=SLANT4
        ENDIF

IF (NOTH_I.EQ.1)TYPE *,' '
        IF (NOTH_I.EQ.1)TYPE *,'IT=',IT
        IF (NOTH_I.EQ.1)TYPE *,'PLACE=',PLACE
        IF (NOTH_I.EQ.1)TYPE *,'SCHEME=',SCHEME
        IF (NOTH_I.EQ.1)TYPE *,' '

IF (IT.EQ.1.OR.IT.EQ.2)THEN  !CORRECT DELAY WINDOW FOR NONLEVELNESS
        DELAY_CORR=DELAY(IT)+(SLANTX*ILOCX*SCANSTEP)+(SLANTY*ILOCY*INDXSTEP)
        ELSEIF (IT.EQ.3.OR.IT.EQ.4)THEN
        DELAY_CORR=DELAY(IT)+(SLANTXR*ILOCX*SCANSTEP)+(SLANTYR*ILOCY*INDXSTEP)
        ENDIF

TYPE *,' '
        TYPE *,' '
        TYPE *,' '
        TYPE *,'J=',J,' DELAY(',IT,')= ',DELAY(IT)
        TYPE *,'DELAY_CORR=',DELAY_CORR
        TYPE *,' '
        TYPE *,' '
        TYPE *,' '
```

```
        IF (PLACE.GE.1.AND.SCHEME.EQ.'B'.AND.NOTH_I.EQ.1)THEN
        IIIT=2  !CORRECT DELAY WINDOW FOR NONLEVELNESS
        DELAY_CORR=DELAY(2)+(SLANTX*ILOCX*SCANSTEP)+(SLANTY*ILOCY*INDXSTEP)

CALL PUTTIME(DELAY_CORR)       ! Set delay FOR B2

!!! USER-DEFINE VOLTAGE SETTINGS?

IF (VOLANS.EQ.'U')THEN
        VOLTS=VOL(2)
        CALL SETVOLTDIV(VOLTS)
        ENDIF
        IF (VOLANS.EQ.'A')CALL AUTOSETVOLTS( MAI,VOLTS,NUMINT )!Set V/D
        GOTO 1132
            ENDIF

C   !KEEP TRACK OF POSITION WHERE DATA IS ACTUALLY TAKEN WITH A COUNTER
        IF (IT.EQ.1.AND.PLACE.GE.1.AND.SCHEME.EQ.'X')SCANKNT=SCANKNT+1
        IF (NOTH_I.EQ.1)TYPE *,' '
        IF (NOTH_I.EQ.1)TYPE *,' X=',J,' Y=',I,' SCANKNT=',SCANKNT
        IF (NOTH_I.EQ.1)TYPE *,' '

CALL PUTTIME( DELAY_CORR )     ! Set delay AS USUAL

100     CONTINUE

IF ((VOLANS.EQ.'U'.AND.(IT.EQ.1.OR.IT.EQ.2.OR.IT.EQ.3)).OR.
1       (UOLANS.EQ.'U'.AND.IT.EQ.4))THEN  !!! USER-DEFINE VOLTAGE SETTINGS
        VOLTS=VOL(IT)
        CALL SETVOLTDIV(VOLTS)
        GOTO 1132
        ENDIF

CALL AUTOSETVOLTS( MAI,VOLTS,NUMINT )      ! Set V/D
1132    IF((VOLTS.GT.1.0).OR.(VOLTS.LT.0.01))THEN
        WRITE(5,1131)VOLTS
1131    FORMAT('+','BAD VOLTAGE SETTING',E10.5)
        CALL TEKRESET(MAI)
        GOTO 100
        ENDIF

CALL GETSA(NAVE,MAI,A)    ! Get waveform
        WATCH1 = A(1)/ NAVE       ! Make sure its acceptable
        TYPE *,' '
        TYPE *,' '
        TYPE *,' '
        WRITE(5,1133)WATCH1,WATCH
1133    FORMAT('+','CURRENT WATCH LEVEL IS',F10.5,'MIN =',F10.5)
        TYPE *,' '
        TYPE *,' '
        TYPE *,' '

IF (VOLANS.EQ.'U'.OR.UOLANS.EQ.'U')GOTO 56732 !! SKIP WATCH
```

```
        IF( WATCH1.LT.WATCH )THEN
                WFLAG = 1
                WRITE( 5,10200 )
            FLAG='H' !H = SAMPLE HOLDER
            TYPE *,'FLAG=',FLAG
C
C !COUNTER FOR BAD WATCH LEVEL, IE. ON WHICH WAVEFORM (B1 OR B2) DOES IT OCCUR
C
C           IF (SCHEME.EQ.'X'.AND.IT.EQ.1)WATCH_COUNT=1
C           IF (SCHEME.EQ.'X'.AND.IT.EQ.2)WATCH_COUNT=2
C           TYPE *,'WATCH_COUNT=',WATCH_COUNT

GOTO 20000
10201       format(' ',A,' ',A,' X= ',I3,' Y= ',I3 )
10200       format(' WAVEFORM BELOW "WATCH", GOING TO NEXT SCAN POINT')
C           GOTO 100
            ENDIF
C***************************************************************

56732   CONTINUE
C***************************************************************

IF (NOTH_I.EQ.1)TYPE *,' '
        IF (NOTH_I.EQ.1)TYPE *,'PLACE=',PLACE
        IF (NOTH_I.EQ.1)TYPE *,'SCHEME=',SCHEME
        IF (NOTH_I.EQ.1)TYPE *,'TSCHEME=',TSCHEME
        IF (NOTH_I.EQ.1)TYPE *,'ZEROO=',ZEROO
        IF (NOTH_I.EQ.1)TYPE *,'IIIT=',IIIT
C       IF (NOTH_I.EQ.1)TYPE *,'WATCH_COUNT=',WATCH_COUNT
        IF (NOTH_I.EQ.1)TYPE *,' '
C **** EXAMINE B2(t) APPROACH FOR SAMPLE HOLDER ******* C
        IF (PLACE.GE.1.AND.SCHEME.EQ.'B'.AND.IIIT.EQ.2)THEN
            AA = 0.                         !
            DO 499 III=1,512                ! Subtract average from wave,
            A11(III)=A(III)
            A11(III)=A11(III)/NAVE          !
499         AA=AA + A11(III)                ! REALWAVE = Waveform in volts
            ZERO = AA/512.                  !
            IF (NOTH_I.EQ.1)TYPE *,'ZERO=',ZERO
            FF=0.
            DO 599 III=1,512
            F1(III) = ( REAL(A11(III)) - ZERO )*( VOLTS )*10./512.
599         FF=FF + ABS(F1(III))
            ZEROO=FF/512.
            IF (NOTH_I.EQ.1)TYPE *,' '
            IF (NOTH_I.EQ.1)TYPE *,'ZEROO=',ZEROO
            IF (NOTH_I.EQ.1)TYPE *,' '
C******* MOD FOR AUTOMATIC NOISE THRESHOLD ******************
C SET UZEROO = 2*(FIRST "NOISE" LEVEL DETECTED --> ASSUME WE ARE STARTING
C                                                 ON SAMPLE HOLDER)
            IF (TSCHEME.EQ.'A'.AND.PLACE.EQ.1)THEN
            UZEROO=2*ZEROO
            IF (NOTH_I.EQ.1)TYPE *,' '
            IF (NOTH_I.EQ.1)TYPE *,' AUTO THRESHOLD VOLTAGE NOISE LEVEL =',UZEROO
            IF (NOTH_I.EQ.1)TYPE *,' '
```

```
        ELSEIF (TSCHEME.EQ.'M'.AND.PLACE.EQ.1)THEN
        IF (NOTH_I.EQ.1)TYPE *,' '
        IF (NOTH_I.EQ.1)TYPE *,' MANUALLY-SET THRESHOLD VOLTAGE NOISE LEVEL =',UZEROO
        IF (NOTH_I.EQ.1)TYPE *,' '
        ENDIF
C ***********************************************************
        IF (ZEROO.LT.UZEROO)THEN  !!!< EX..002 VOLTS - ON SAMPLE HOLDER
56120   FLAG='H'  !H = SAMPLE HOLDER
        IF (NOTH_I.EQ.1)TYPE *,'FLAG=',FLAG
        GOTO 20000
        ELSEIF (ZEROO.GE.UZEROO)THEN !!!> EX..002 VOLTS - ON SAMPLE
56121   FLAG='S'  !S = SAMPLE
        IF (NOTH_I.EQ.1)TYPE *,'FLAG=',FLAG
        SCHEME='X'
        GOTO 10386 !START TAKEDATA LOOP AGAIN
        ENDIF
        ENDIF

IF (NOTH_I.EQ.1)THEN
500     WRITE(16,REC=I16,FMT=53)DELAY_CORR
        I16=I16+1
        WRITE(16,REC=I16,FMT=53)VOLTS
        I16=I16+1
C
        DO 54321 IJI=1,512
        I17SUB=((I17-1)*512)+IJI
54321   WRITE(17,REC=I17SUB,FMT=54) A(IJI)
        I17=I17+1 elseif (noth_I.eq.2)then

5500    WRITE(26,REC=I26,FMT=53)DELAY_CORR
        I26=I26+1
        WRITE(26,REC=I26,FMT=53)VOLTS
        I26=I26+1
C
        DO 54329 IJI=1,512
        I27SUB=((I27-1)*512)+IJI
54329   WRITE(27,REC=I27SUB,FMT=54) A(IJI)
        I27=I27+1 elseif (noth_I.eq.3)then

5800    WRITE(36,REC=I36,FMT=53)DELAY_CORR
        I36=I36+1
        WRITE(36,REC=I36,FMT=53)VOLTS
        I36=I36+1
C
        DO 58329 IJI=1,512
        I37SUB=((I37-1)*512)-IJI
58329   WRITE(37,REC=I37SUB,FMT=54) A(IJI)
        I37=I37+1 elseif (noth_I.eq.4)then
```

```
5900    WRITE(46,REC=I46,FMT=53)DELAY_CORR
        I46=I46+1
        WRITE(46,REC=I46,FMT=53)VOLTS
        I46=I46+1
C
        DO 59329 IJI=1,512
        I47SUB=((I47-1)*512)+IJI
59329   WRITE(47,REC=I47SUB,FMT=54) A(IJI)
        I47=I47+1 endif

C
C       WRITE( 8,10600 )A(200)
C****************************************************C
        IF (IT.EQ.1)VOLTAGE(1)=VOLTS
        IF (IT.EQ.2)VOLTAGE(2)=VOLTS
        IF (IT.EQ.3)VOLTAGE(3)=VOLTS
        IF (IT.EQ.4)VOLTAGE(4)=VOLTS
C****************************************************C
 600    CONTINUE
C****************************************************C
 7      FORMAT (A4)
C****************************************************C
20000   IF( WFLAG.EQ.1 )THEN
        CLOSE(8)
        OPEN( unit=8, file='TXA1:', status='OLD' )
        ENDIF
        IF (SCHEME.EQ.'X')SCHEME='B'  !RESET BACK TO 'B' FOR NEXT SCAN POINT

C       IF (I.NE.0.AND.J.NE.0)THEN

C !RESET COUNTERS TO EXCLUDE DATA GATHERED ON POINT
C  WHERE BAD WATCH LEVEL WAS FOUND

C       IF (WATCH_COUNT.EQ.1)THEN  !B1 HAD BAD WATCH LEVEL
C       SCANKNT=SCANKNT-1
C       I16=I16-2
C       I17=I17-1
C       ELSEIF (WATCH_COUNT.EQ.2)THEN !B2 HAD BAD WATCH LEVEL
C       SCANKNT=SCANKNT-1
C       I16=I16-4
C       I17=I17-2
C       ENDIF if (noth_1.eq.1)WRITE(12)J,I,FLAG,SCANKNT !NOTE LOCATION WITH FLAG & LEAVE SUBR.
        IF (NOTH_1.EQ.1)TYPE *,' '
        IF (NOTH_1.EQ.1)TYPE *,' '
        IF (NOTH_1.EQ.1)TYPE *,' '
        IF (NOTH_1.EQ.1)TYPE *,'NOW IN TAKEDATA:','X=',J,' Y=',I,' FLAG=',FLAG
        IF (NOTH_1.EQ.1)TYPE *,' '
```

```
          IF (NOTH_I.EQ.1)TYPE *,' '
          IF (NOTH_I.EQ.1)TYPE *,' '
          IF (NOTH_I.EQ.1)TYPE *,' '
C         ENDIF

C         WATCH_COUNT=0
          RETURN
        end

C
```

```
        SUBROUTINE PRESSURE(VOLTAGEL,VOLTAGEU)
C
C ****   PRESSURE=20*VOLTAGE ****   (PLOWER.LE.VOLTAGE.GE.PUPPER)
C
C       Adjust Z axis to get good pressure (PSI)
C           <<<   11 = DOWN   >>>
C
C       PUPPER = .85    !   Upper Pressure = 17
C       PLOWER = .75    !   Lower Pressure = 15
C       PUPPER = .3     !   UPPER PRESSURE = 6
C       PLOWER = .2     !   LOWER PRESSURE = 4
C       PUPPER = .5     !   UPPER PRESSURE = 10
C       PLOWER = .4     !   LOWER PRESSURE = 8
C       PLOWER = .5     !   LOWER PRESSURE = 10
C       PUPPER = .6     !   UPPER PRESSURE = 12
C       PLOWER = .7     !   LOWER PRESSURE = 14
C       PUPPER = .8     !   UPPER PRESSURE = 16
C       PLOWER = .6     !   LOWER PRESSURE = 12
C       PUPPER = .61    !   UPPER PRESSURE = 12.2
        PLOWER=VOLTAGEL
        PUPPER=VOLTAGEU
200     CALL GETFLUKE( P )
        IF( P.GE.PLOWER .AND. P.LE.PUPPER )GOTO 900
        IF( P.LT.PLOWER )CALL MOVXYZ( 3, 1 )
        IF( P.GT.PUPPER )CALL MOVXYZ( 3, -1 )
        GOTO 200
900     RETURN
        end
C
```

```
      SUBROUTINE PRESSURE_MAX(VOLTAGE_MAX,LLL,FILENAME,J,I,I15,CHECKP)
C
      CHARACTER FILENAME*34
      INTEGER*2 CHECKP,LLL,LINCR,I,J,JXXX,I15,ITTT
52    FORMAT(A2)
      P_MAX=VOLTAGE_MAX
200   CALL GETFLUKE( P )
      IF( P.GT.P_MAX)THEN
      CHECKP=CHECKP+1
      IF (CHECKP.EQ.1)LINCR=LLL/3
      IF (CHECKP.EQ.2)LINCR=LLL/2
      IF (CHECKP.EQ.3)LINCR=1000
      DO 2900 ITTT=1,LINCR
2900  CALL MOVXYZ( 3,-1 )  !3 IS Z-AXIS, MOVE Z-AXIS UP
      IF (CHECKP.EQ.3)THEN
      JXXX=I-1  !I IS Y-LOC; GO BACK TO PREVIOUS ROW
      WRITE(15,REC=I15,FMT=52)JXXX
      I15=I15+1
      STOP
      ENDIF
      ENDIF
900   RETURN
      end
C
```

```
      SUBROUTINE MOVORG( SCANAXIS, NSTEPS,VOLTAGEL,VOLTAGEU,
     1    LOOPTHRU_H)
C
C    Run the thing back to the SCANAXIS origin
C
        integer*4  SCANAXIS
        integer*2  NSTEPS,LOOPTHRU_H C       DO 1000 K=1,LOOPTHRU_H
C 1000  CALL MOVXYZ( 3,-1 )      !  Move up
        DO 1200 K=1,NSTEPS-1
 1200   CALL MOVXYZ( SCANAXIS, -1 )  !  Move back
C       DO 1400 K=1,LOOPTHRU_H
C 1400  CALL MOVXYZ( 3, 1 )      !  Move down
C       CALL PRESSURE(VOLTAGEL,VOLTAGEU) !nothick
C       CALL MOVXYZ( SCANAXIS, -1 )  !  Move back & forth
C       CALL MOVXYZ( SCANAXIS, 1 )
        RETURN
        end SUBROUTINE MOVORGXY( ZIGANS,SCANAXIS,NSCAN,INDXAXIS,NINDX)
C
C    Run the thing back to the SCAN origin
C
        CHARACTER   ZIGANS*1
        integer*4   SCANAXIS,INDXAXIS
        integer*2   NSCAN,NINDX,I IF (ZIGANS.EQ.'Y')THEN
        I=Nindx IF (I.EQ.1.OR.I.EQ.3.OR.I.EQ.5.OR.I.EQ.7.OR.I.EQ.9
     1 .OR.I.EQ.11.OR.I.EQ.13.OR.I.EQ.15.OR.I.EQ.17.OR.I.
     1 EQ.19.OR.I.EQ.21.OR.I.EQ.23.OR.I.EQ.25.OR.I.EQ.27.OR.
     1 I.EQ.29.OR.I.EQ.31.OR.I.EQ.33.OR.I.EQ.35.OR.I.EQ.37.
     1 OR.I.EQ.39.OR.I.EQ.41.OR.I.EQ.43.OR.I.EQ.45.OR.I.EQ.
     1 47.OR.I.EQ.49.OR.I.EQ.51.OR.I.EQ.53.OR.I.EQ.55.OR.
     1 I.EQ.57.OR.I.EQ.59.OR.I.EQ.61.OR.I.EQ.63.OR.I.EQ.65
     1 .OR.I.EQ.67.OR.I.EQ.69.OR.I.EQ.71.OR.I.EQ.73.OR.I.
     1 EQ.75.OR.I.EQ.77.OR.I.EQ.79.OR.I.EQ.81.OR.I.EQ.83.OR
     1 .I.EQ.85.OR.I.EQ.87.OR.I.EQ.89.OR.I.EQ.91.OR.I.
     1 EQ.93.OR.I.EQ.95.OR.I.EQ.97.OR.I.EQ.99)THEN DO 1200 K=1,NSCAN-1
 1200   CALL MOVXYZ( SCANAXIS, -1 )  !  Move back X
        ENDIF
        ENDIF DO 1400 K=1,NINDX-1
 1400   CALL MOVXYZ( INDXAXIS, -1 )  !  Move back Y
```

```
        RETURN
        end

C
```

```
      SUBROUTINE ENTERPARAM( SCANSTEP,INDXSTEP,NSCAN,NINDX,NAVE,VOLTAGEL
     1    ,VOLTAGEU,VOLTAGE_MAX,SHAPEANS,LOOPANS,LOOPTHRU_H,LOOPTHRU_S,
     1 ZIGANS,SCHEME,TSCHEME,UZEROO,FILENAME,I15,SCANMODE,SLANT1,SLANT2,
     1 SLANT3,SLANT4)
          integer*4  SCANSTEP,INDXSTEP
          real       SCANDIST, INDXDIST,PU,PL,SLANT,rslant1,RSLANT2,SLANT1,SLANT2
          REAL       SLANT3,SLANT4,RSLANT3,RSLANT4
          INTEGER*2  LOOPTHRU_H,LOOPTHRU S,ISLANT1,ISLANT2
          integer*2  NSCAN,NINDX, IDIST1,IDIST2,I6,I15
          integer*2  FREQ,NAVE,ISLANT3,ISLANT4
          character  FILENAME*34, FILEEXT*23, CHEADER*32
          CHARACTER  LOOPANS*1,SCHEME*1
          CHARACTER  SHAPEANS*1,ZIGANS*1
          CHARACTER  TSCHEME*1,SCANMODE*1
          DATA I6/1/
          I15=1
10010 format( A )
10012 format( A2 )
10020 format( I )
10030 format( F )
C
C Initialization and entry of parameters
C
C
C
          TYPE *,' '
          TYPE *,' *****> DONSCAN.FOR.......AUTO SCAN'
          TYPE *,' '
          OPEN (UNIT=10,FILE='NOTHICK_ALLSHAPE1.DAT',STATUS='OLD',
     1     FORM='FORMATTED')
          READ (10,93764) SCANMODE
          READ (10,93765) XSCANSTEP !(X IND)
          IF (SCANMODE.EQ.'P')XSCANSTEP=2000.
          READ (10,93765) YINDXSTEP !(Y IND)
          IF (SCANMODE.EQ.'P')YINDXSTEP=2000.
          SCANSTEP=JNINT(XSCANSTEP)
          INDXSTEP=JNINT(YINDXSTEP)

READ (10,93765) SCANDIST !(X DIST)

IF (SCANMODE.EQ.'P')SCANDIST=2000.

READ (10,93765) INDXDIST !(Y DIST)

IF (SCANMODE.EQ.'P')INDXDIST=2000.
          IF (SCANMODE.EQ.'L')THEN
          YINDXSTEP=20000.
          INDXSTEP=JNINT(YINDXSTEP)
          INDXDIST=20000.
          ENDIF

READ (10,93764) ZIGANS
          READ (10,93765) PL
```

```
          READ (10,93765) PU
          READ (10,93765) PM
          READ (10,93764) SHAPEANS
          READ (10,93764) LOOPANS
          READ (10,93766) LOOPTHRU_H
          READ (10,93766) LOOPTHRU_S
          READ (10,93764) TSCHEME
          READ (10,93765) UZEROO
C         READ (10,93765) THICKN
C    ************* "SLANT" IS THE NUMBER OF NANOSECONDS / MICRONS
C                  THAT THE ECHOES MOVE DUE TO NONLEVELNESS OF
C                  EXPERIMENT OR THICKNESS VARIATION. IT MUST BE
C                  INCORPORATED INTO THE PROGRAM AS AN ADDITIVE OR
C                  SUBTRACTIVE VALUE TO ALL THE DELAY TIMES BY FIRST
C                  MULTIPLYING "SLANT" BY THE CUMULATIVE INDEXING DISTANCE
C                  IN THE X-DIRECTION (N*XSCANSTEP) AS THE SCAN IS
C                  BEING PERFORMED AND THEN ADDING / SUBTRACTING THIS
C                  VALUE TO EACH DELAY. "SLANT" MUST BE DETERMINED
C                  BEFORE THE SCAN IS RUN BY MOVING THE X AND Y STAGES
C                  OVER THE SCAN LENGTH AND NOTING THE SHIFT TIME OF
C                  AN ECHO, SAY B1. THIS SHIFT WILL BE CONSISTENT FOR
C                  B1 AND B2 ECHOES IN MOST CASES BUT ANOTHER SLANT
C                  FACTOR WILL HAVE TO BE DEFINED FOR THE ECHO OFF THE
C                  REFLECTOR PLATE. SO WE HAVE SLANT 1 AND SLANT 2.

READ (10,93765) SLANT1
          SLANT1=SLANT1/10.**9.
          RSLANT1=SLANT1*10.**13.    !CONVERT SLANT TO INTEGER FOR STORAGE IN
C                                              .DATI2 FILE
          ISLANT1=IINT(RSLANT1)

READ (10,93765) SLANT2
          SLANT2=SLANT2/10.**9.
          RSLANT2=SLANT2*10.**13.    !CONVERT SLANT TO INTEGER FOR STORAGE IN
C                                              .DATI2 FILE
          ISLANT2=IINT(RSLANT2)

READ (10,93765) SLANT3
          SLANT3=SLANT3/10.**9.
          RSLANT3=SLANT3*10.**13.    !CONVERT SLANT TO INTEGER FOR STORAGE IN
C                                              .DATI2 FILE
          ISLANT3=IINT(RSLANT3)

READ (10,93765) SLANT4
          SLANT4=SLANT4/10.**9.
          RSLANT4=SLANT4*10.**13.    !CONVERT SLANT TO INTEGER FOR STORAGE IN
C                                              .DATI2 FILE
          ISLANT4=IINT(RSLANT4)

READ (10,93765) FREQUENCY
          READ (10,93764) FILEEXT

K=0
126       K=K+1
```

```
              IF( FILEEXT(K:K).NE.' ')GOTO 126  !
              FILEEXT(K+1:K+4)='.DAT'                    ! UNIT 6 = raw data READ (10,93764) CHEADER
93764   FORMAT (A)
93765   FORMAT (F)
93766   FORMAT (I)
C       VOLTAGEL=PL/20.
C       VOLTAGEU=PU/20.
C       VOLTAGE_MAX=PM/20.
C       TYPE *,'RUN TEMPDIRSCAN_COM – DIRSCAN SMALLTRANS_DATA.DAT'
        TYPE *,'DATA FOR ULTRASONIC SCAN (ALL FLOATING PT. EXCEPT INDEXES)'
        TYPE *,'SCAN DIMENSIONS/INDEXING DATA (MICRONS)'
        TYPE *,'X INDEX - INTEGER EXPRESSION'
        TYPE *,SCANSTEP
        TYPE *,'Y INDEX - INTEGER EXPRESSION'
        TYPE *,INDXSTEP
        TYPE *,' X SCAN DISTANCE (MICRONS) - FLOATING POINT'
        TYPE *,SCANDIST
        TYPE *,' X SCAN DISTANCE (MICRONS) - FLOATING POINT'
        TYPE *,INDXDIST
C       TYPE *,' LOWER & UPPER PRESSURES FOR CONTACT SCAN'
C       TYPE *,PL,PU
C       TYPE *,'THICKNESS (MM)'
C       TYPE *,THICKN
        TYPE *,'SLANT1 (X-LEVELNESS TIME CORRECTION FACTOR for b1,b2) (nsec / um )'
        TYPE *,SLANT1
        TYPE *,'SLANT2 (X-LEVELNESS TIME CORRECTION FACTOR for reflector echoes) (nsec / um )'
        TYPE *,SLANT2
        TYPE *,'SLANT3 (Y-LEVELNESS TIME CORRECTION FACTOR for b1,b2) (nsec / um )'
        TYPE *,SLANT3
        TYPE *,'SLANT4 (Y-LEVELNESS TIME CORRECTION FACTOR for reflector echoes) (nsec / um )'
        TYPE *,SLANT4
        TYPE *,'TRANSDUCER CENTER FREQUENCY (FLOATING POINT)'
        TYPE *,FREQUENCY
        TYPE *,'FILENAME FOR RAW DATA '
        TYPE *,FILEEXT
        TYPE *,'CHEADER INFO (UP TP 32 CHARACTERS)'
        TYPE *,CHEADER
        TYPE *,' '
1000    NSCAN = (SCANDIST/SCANSTEP) + 1
        NINDX = (INDXDIST/INDXSTEP) - 1
        SCANDIST = SCANSTEP*(NSCAN-1)              ! SCANDIST = negative
        INDXDIST = INDXSTEP*(NINDX-1)
        IF (SCANMODE.EQ.'S')THEN
        WRITE( 5,11100 )SCANDIST, NSCAN, SCANSTEP,
      +      INDXDIST, NINDX, INDXSTEP
        ELSEIF (SCANMODE.EQ.'L')THEN
        WRITE( 5,11200 )SCANDIST, NSCAN, SCANSTEP
        ELSEIF (SCANMODE.EQ.'P')THEN
        WRITE( 5,11300 )
        ENDIF
11100   format( /' ',
      + /' X scan to ',F7.0,',',I3,' steps of ',I5,
      + /' Y index to ',F7.0,',',I3,' steps of ',I5)
```

```
11200  format(/' ',
     -  //' Line scan to ',F7.0,',',I3,' steps of ',I5)
11300  format(/' ',//' Point Measure repeated 2 times')
                 SCHEME='B'
C                THICK= IINT(THICKN*1000.)
                 FREQ=FREQUENCY
                 NAVE=64
           FILENAME = '[ROTH.DATA]'//FILEEXT
           WRITE( 5,11690 )
11690  format( /'$NUMBER OF AVERAGES SET AT 64' )
C***************************************************************
C
C               DIRECT ACCESS STORAGE
C OPEN( unit=6, file=FILENAME//'CH', status='NEW',
     -      ACCESS='DIRECT',RECORDTYPE='FIXED',RECL=32,
     -           form='FORMATTED',ORGANIZATION='SEQUENTIAL' )
      OPEN( unit=15, file=FILENAME//'I2', status='NEW',
     +      ACCESS='DIRECT',RECORDTYPE='FIXED',RECL=2,
     +           form='FORMATTED',ORGANIZATION='SEQUENTIAL' )
      OPEN( unit=16, file=FILENAME//'R4', status='NEW',
     +      ACCESS='DIRECT',RECORDTYPE='FIXED',RECL=4,
     +           form='FORMATTED',ORGANIZATION='SEQUENTIAL' )
      OPEN( unit=17, file=FILENAME//'WAV', status='NEW',
     +      ACCESS='DIRECT',RECORDTYPE='FIXED',RECL=2,
     +           form='FORMATTED',ORGANIZATION='SEQUENTIAL' )
      OPEN( unit=26, file=FILENAME//'RR4', status='NEW',
     +      ACCESS='DIRECT',RECORDTYPE='FIXED',RECL=4,
     +           form='FORMATTED',ORGANIZATION='SEQUENTIAL' )
      OPEN( unit=27, file=FILENAME//'RWAV', status='NEW',
     +      ACCESS='DIRECT',RECORDTYPE='FIXED',RECL=2,
     +           form='FORMATTED',ORGANIZATION='SEQUENTIAL' )
      OPEN( unit=36, file=FILENAME//'SR4', status='NEW',
     +      ACCESS='DIRECT',RECORDTYPE='FIXED',RECL=4,
     +           form='FORMATTED',ORGANIZATION='SEQUENTIAL' )
      OPEN( unit=37, file=FILENAME//'SWAV', status='NEW',
     +      ACCESS='DIRECT',RECORDTYPE='FIXED',RECL=2,
     +           form='FORMATTED',ORGANIZATION='SEQUENTIAL' )
      OPEN( unit=46, file=FILENAME//'TR4', status='NEW',
     +      ACCESS='DIRECT',RECORDTYPE='FIXED',RECL=4,
     +           form='FORMATTED',ORGANIZATION='SEQUENTIAL' )
      OPEN( unit=47, file=FILENAME//'TWAV', status='NEW',
     +      ACCESS='DIRECT',RECORDTYPE='FIXED',RECL=2,
     +           form='FORMATTED',ORGANIZATION='SEQUENTIAL' )
51        FORMAT(A32)
52        FORMAT(A2)
53        FORMAT(A4)
54        FORMAT(A2)
C
C  Write header : X, Y dist, X, Y scan points, dummies
C
          WRITE(6,REC=I6,FMT=51 )CHEADER
          I6=I6+1
          WRITE(6,REC=I6,FMT=51 )SHAPEANS
```

```
      I6=I6+1
      WRITE(6,REC=I6,FMT=51 )ZIGANS
      I6=I6+1
      IDIST1 = - IIFIX(SCANDIST/1000.)
      IDIST2 = IIFIX(INDXDIST/1000.)
      IF (IDIST2.LT.1)IDIST2=1  !TRICK TO ALLOW DISPLAY OF IMAGE ON PSIDD
      WRITE(15,REC=I15,FMT=52 )IDIST1
      I15=I15+1
      WRITE(15,REC=I15,FMT=52)IDIST2
      I15=I15+1
      WRITE(15,REC=I15,FMT=52)NSCAN
      I15=I15+1
      IF (SCANMODE.EQ.'L'.OR.SCANMODE.EQ.'P')NINDX=1 !MOD FOR LINE/POINT SCAN
      WRITE(15,REC=I15,FMT=52)NINDX
      I15=I15+1
C     WRITE(15,REC=I15,FMT=52)THICK
      WRITE(15,REC=I15,FMT=52)ISLANT1
      I15=I15+1
      WRITE(15,REC=I15,FMT=52)ISLANT2
      I15=I15+1
      WRITE(15,REC=I15,FMT=52)ISLANT3
      I15=I15+1
      WRITE(15,REC=I15,FMT=52)ISLANT4
      I15=I15+1
      WRITE(15,REC=I15,FMT=52)DENS
      I15=I15+1
      WRITE(15,REC=I15,FMT=52)FREQ
      I15=I15+1
      WRITE(15,REC=I15,FMT=52)NAVE
      I15=I15+1
      RETURN
      end SUBROUTINE XPARAM( SCANSTEP,INDXSTEP,NSCAN,NINDX )
      integer*4 SCANSTEP,INDXSTEP
      integer*2 NSCAN,NINDX
      SCANSTEP = 50
      INDXSTEP = 50
      NSCAN   = 50
      NINDX   = 50
      THICK   = 1
      OPEN( unit=6, file='XXX.DAT', status='OLD',
     +   form='UNFORMATTED' )
      SCANSTEP = 50
      RETURN
      end SUBROUTINE MOVKLING (AXIS,DIST)
C
C     MOVE KLINGER A SPECIFIED DISTANCE IN SPECIFIED DIRECTION
C
      byte IXYZ
      character*1 XYZ
      equivalence( XYZ, IXYZ )
      common  WRK0,BUFFER
```

```
        CALL STRTGPIB
        CALL INITINSTR(2)
        CALL INITINSTR(3)
        CALL INITINSTR(4)
10010   format(A)
10020   format(I)
10100   format( /'SDistance ?' )
100     WRITE( 5,10000 )
10000   format( /'$X, Y, or Z ?' )
        READ( 5,10010 )XYZ
        IF( IXYZ.GT.90. OR .IXYZ.LT.88 )GOTO 900
        IPORN=1
        WRITE( 5,10100 )
        READ( 5,10020 )IREQ
        IF( IREQ.LT.0 )THEN
           IPORN=-1
           IREQ=ABS(IREQ)
           ENDIF
        CALL SETXYZ( IREQ,IREQ,IREQ )
        IAXIS = IXYZ - 87
        CALL MOVXYZ( IAXIS,IPORN )
        GOTO 100
900     STOP
        RETURN
        end

INCLUDE '[ROTH.MENU]BASE0_2SEC_M.FOR'
```

```
C      nothick_crunch.for --- 4 SCAN METHOD

C      Crunch program for Nothickness velocity scan

C      Don Roth 20-sep-1994 integer*2  SCANDIST,INDXDIST,NSCAN,NINDX,JJ,II,SCANKNT
       integer*2  DENS,TRFREQ,AVES,NPOINT,I6,I15,I16,I18,I26
       integer*2  ARRAYSIZE,KCOUNT,SELFREQ,ENDFREQ,I85,I36,I46
       INTEGER*2  islant1,islant2,ISLANT3,ISLANT4,ACTPOINT,JXXX
       integer*2  rawwaveb1(512),rawwaveb2(512),rawwavers(512),rawwaverns(512)
       INTEGER*4  I17,I7,REC,I27,I7SUB,I37,I47,I27SUB,I37SUB,I47SUB,I17SUB
       real*4 L_VEL,U_VEL,AV_VEL
       real*4     ASPECB1(1024), ASPECB2(1024)
       real*4     B1ASPEC(256), B2ASPEC(256)
       real*4     ASPECRS(1024), ASPECRNS(1024)
       real*4     RSASPEC(256), RNSASPEC(256)

REAL*4 B1PHASE(256),PHASEB1(1024)
       REAL*4 B2PHASE(256),PHASEB2(1024)
       REAL*4 RSPHASE(256),PHASERS(1024)
       REAL*4 RNSPHASE(256),PHASERNS(1024)
       REAL*4 BB1(512),BB2(512),RRS(512),RRNS(512)
       REAL*4 VEL(5000),TRDIAM,BUFLENGTH
       character FILENAME*32, FILEEXT*26, CHEADER*32,NOISANS*1
       character FS1EXT*16,CALNAME*32,FLAG*1
       CHARACTER DIFFANS*1,PHASE*1,PHASE1*1
       CHARACTER SELFREQANS*1
       CHARACTER SHAPEANS*1,ZIGANS*1,DIR*5
       CHARACTER CRUNCH_CODE*2,CFILTER*1
       character actual_selfreqans*1 byte       FILEFS1IN
       equivalence ( B1ASPEC,ASPECB1 )               !-------------------!
       equivalence ( B2ASPEC,ASPECB2 )               !  *ASPEC  256      !
       equivalence ( RSASPEC,ASPECRS )               !-------------------!
       equivalence ( RNSASPEC,ASPECRNS )             !  *ASPEC  256      !
       EQUIVALENCE (B1PHASE,PHASEB1)                 !-------------------!
       EQUIVALENCE (B2PHASE,PHASEB2)
       EQUIVALENCE (RSPHASE,PHASERS)                 !-------------------!
       EQUIVALENCE (RNSPHASE,PHASERNS)
       equivalence ( FS1EXT, FILEFS1IN )

DATA I6/1/,I15/1/,I16/1/,I17/1/,I7/1/,I18/1/
       DATA I26/1/,I27/1/,I85/1/,I36/1/,I37/1/,I46/1/,I47/1/

NIPI=0

10010  format(A)
10014  format(' ',A )
10020  format(I)
10030  format(F)
C
```

```
        OPEN (UNIT=14,FILE='NOTHICK_SELFREQ1.DAT',
    1   STATUS='OLD',FORM='FORMATTED')
        READ (14,98652) FILEEXT
        READ (14,98652) DRIVE
        READ (14,98652) PHASE
        READ (14,98652) PHASE1
        READ (14,98652) DIFFANS
        READ (14,10030) BUFLENGTH
        READ (14,10030) BUFVEL
        READ (14,10030) TRDIAM
        CLOSE (14)
98652   FORMAT (A)
C ********* OPEN FILTER FILE FOR UPPER & LOWER LIMITS ********** C

OPEN (UNIT=24,FILE='NOTHICK_LIMITS1.DAT',
    1   STATUS='OLD',FORM='FORMATTED')
        READ (24,98652) CFILTER
        READ (24,10030) L_VEL
        READ (24,10030) U_VEL
        L_VEL=L_VEL
        U_VEL=U_VEL
        AV_VEL=(L_VEL+U_VEL)/2.

C ************************************************** C

K=0
126     K=K+1
        IF( FILEEXT(K:K).NE.' ')GOTO 126 !
        FILEEXT(K+1:K+4)='.DAT'              ! UNIT 6 = raw data

IF (DRIVE.EQ.'A')DIR='DUC2:'
        IF (DRIVE.EQ.'C')DIR='DUC0:'

FILENAME = '[ROTH.DATA]'//FILEEXT
C***************************************************************
C           DIRECT ACCESS STORAGE
C
        OPEN( unit=76, file=DIR//FILENAME//'GB', status='NEW',
    +   ACCESS='DIRECT',RECORDTYPE='FIXED',RECL=4,
    +        form='FORMATTED',ORGANIZATION='SEQUENTIAL' )
        OPEN( unit=66, file=FILENAME//'CH', status='OLD',
    +   ACCESS='DIRECT',RECORDTYPE='FIXED',RECL=32,
    +        form='FORMATTED',ORGANIZATION='SEQUENTIAL' )
        OPEN( unit=15, file=FILENAME//'I2', status='OLD',
    +   ACCESS='DIRECT',RECORDTYPE='FIXED',RECL=2,
    +        form='FORMATTED',ORGANIZATION='SEQUENTIAL' )
        OPEN( unit=16, file=FILENAME//'R4', status='OLD',
    +   ACCESS='DIRECT',RECORDTYPE='FIXED',RECL=4,
    +        form='FORMATTED',ORGANIZATION='SEQUENTIAL' )
        OPEN( unit=17, file=FILENAME//'WAV', status='OLD',
    +   ACCESS='DIRECT',RECORDTYPE='FIXED',RECL=2,
```

```
     +            form='FORMATTED',ORGANIZATION='SEQUENTIAL')
            OPEN( unit=26, file=FILENAME//'RR4', status='OLD',
     +      ACCESS='DIRECT',RECORDTYPE='FIXED',RECL=4,
     +            form='FORMATTED',ORGANIZATION='SEQUENTIAL')
            OPEN( unit=27, file=FILENAME//'RWAV', status='OLD',
     +      ACCESS='DIRECT',RECORDTYPE='FIXED',RECL=2,
     +            form='FORMATTED',ORGANIZATION='SEQUENTIAL')
            OPEN( unit=36, file=FILENAME//'SR4', status='OLD',
     +      ACCESS='DIRECT',RECORDTYPE='FIXED',RECL=4,
     +            form='FORMATTED',ORGANIZATION='SEQUENTIAL')
            OPEN( unit=37, file=FILENAME//'SWAV', status='OLD',
     +      ACCESS='DIRECT',RECORDTYPE='FIXED',RECL=2,
     +            form='FORMATTED',ORGANIZATION='SEQUENTIAL')
            OPEN( unit=46, file=FILENAME//'TR4', status='OLD',
     +      ACCESS='DIRECT',RECORDTYPE='FIXED',RECL=4,
     +            form='FORMATTED',ORGANIZATION='SEQUENTIAL')
            OPEN( unit=47, file=FILENAME//'TWAV', status='OLD',
     +      ACCESS='DIRECT',RECORDTYPE='FIXED',RECL=2,
     +            form='FORMATTED',ORGANIZATION='SEQUENTIAL')
C
51          FORMAT(A32)
52          FORMAT(A2)
53          FORMAT(A4)
153         FORMAT(1X,I4,1X,I4,1X,I4,1X,E12.5,1X,E12.5,1X,E12.5,1X,E12.5,1X,
     +      E12.5,1X,E12.5)
54          FORMAT(A2)
            K=0
120         K=K+1
            IF( FILEEXT(K:K).NE.' ')GOTO 120   !
            FILEEXT(K+1:K+3)='SPC'                      ! UNIT 6 = raw data
            FILENAME = '[ROTH.DATA]'//FILEEXT   !
C
C*************UNIT=7,.SPC FILE FOR SPECTRA, vel, FOR DIRECT ACCESS*******C
C
            OPEN( unit=7, file=DIR//FILENAME, status='NEW',ACCESS='DIRECT',
     +      RECORDTYPE='FIXED',RECL=4,FORM='FORMATTED',
     +            ORGANIZATION='SEQUENTIAL')

WRITE( 6,10200 )FILENAME                    ! UNIT 8 = calibration
10200       format(' Filename of analyzed data is ',A )
            FILEEXT(K+1:K+3)='CAL'
            CALNAME = '[ROTH.DATA]'//FILEEXT
            OPEN( unit=8, file=CALNAME, status='NEW', ACCESS='DIRECT',
     +      RECORDTYPE='FIXED',RECL=4,FORM='FORMATTED',
     +            ORGANIZATION='SEQUENTIAL')

89651       DO 76065 IOPI=1,1024
            PHASEB1(IOPI)=0.
            PHASEB2(IOPI)=0.
            PHASERS(IOPI)=0.
            PHASERNS(IOPI)=0.
            ASPECB1(IOPI)=0.
            ASPECB2(IOPI)=0.
            ASPECRS(IOPI)=0.
76065       ASPECRNS(IOPI)=0.
```

```
            KCOUNT=1

C  # # # #   R e a d  preliminary scan info  # # # #
C
79193   READ(66,REC=I6,FMT=51)CHEADER
        I6=I6+1
        READ(66,REC=I6,FMT=51)SHAPEANS
        I6=I6+1
        READ(66,REC=I6,FMT=51)ZIGANS
        I6=I6+1

IF (SHAPEANS.NE.'Y')GOTO 89714
        OPEN(UNIT=12,FILE='[ROTH.DATA]'//FILEEXT(1:K)/'DATHS'.
    1   STATUS='OLD',FORM='UNFORMATTED') !INFO ON WHETHER WE ARE ON HOLDER/SAMPLE

89714   READ(15,REC=I15,FMT=52)SCANDIST
        I15=I15+1
        READ(15,REC=I15,FMT=52)INDXDIST
        I15=I15+1
        READ(15,REC=I15,FMT=52)NSCAN
        I15=I15+1
        READ(15,REC=I15,FMT=52)NINDX
        I15=I15+1
        READ(15,REC=I15,FMT=52)islant1
        I15=I15+1
        READ(15,REC=I15,FMT=52)islant2
        I15=I15+1
        READ(15,REC=I15,FMT=52)islant3
        I15=I15+1
        READ(15,REC=I15,FMT=52)islant4
        I15=I15+1
        READ(15,REC=I15,FMT=52)DENS
        I15=I15+1
        READ(15,REC=I15,FMT=52)TRFREQ
        I15=I15+1
        READ(15,REC=I15,FMT=52)AVES
        I15=I15+1
        READ(15,REC=I15,FMT=52)JXXX
        I15=I15+1
        ARRAYSIZE=(NSCAN)*(JXXX) !IF SCAN FINISHED PROPERLY,JXXX=NINDX

READ(16,REC=I16,FMT=53)TIMESET
        I16=I16+1

ENDFREQ=TRFREQ*2.5
        CALL POINT_FROM_FREQ(ENDFREQ,TIMESET,ACTPOINT)

DELTAF  = 1./(TIMESET*20.)
        NPOINT=NSCAN*JXXX   !IF SCAN FINISHED PROPERLY, JXXX=NINDX
        NWAVES = 3*NPOINT

C       !!! Loop thru scan data

ITEM_COUNT=0
```

```
99651  DO 1890 NIP=1,NPOINT  !!NPOINT IS TOTAL OF ALL POINTS
       SCANKNT=NIP
       ITEM_COUNT=ITEM_COUNT+1
          IF (SHAPEANS.EQ.'N'.AND.NIP.GE.2)ITEM_COUNT=2
          TYPE *,' '
          TYPE *,' ITEM_COUNT= ',ITEM_COUNT
          TYPE *,' CRUNCH_CODE= ',CRUNCH_CODE
          TYPE *,' '
          CCVACCUM=0.
67519  CONTINUE

NIPJ=((NIP-1)/NSCAN)+1       !Y LOCATION
       NIPI=NIPI+1  !X LOCATION
       IF (NIPI.EQ.(NSCAN+1))NIPI=1 !RESET X LOCATION

C ***** MODIFICATION FOR ZIGZAG SCAN *****************************C
           IF (ZIGANS.EQ.'Y')THEN
             IF (NIPJ.EQ.2.OR.NIPJ.EQ.4.OR.NIPJ.EQ.6.OR.NIPJ.EQ.8.OR.NIPJ.EQ.10
     1 .OR.NIPJ.EQ.12.OR.NIPJ.EQ.14.OR.NIPJ.EQ.16.OR.NIPJ.EQ.18.OR.NIPJ.
     1 EQ.20.OR.NIPJ.EQ.22.OR.NIPJ.EQ.24.OR.NIPJ.EQ.26.OR.NIPJ.EQ.28.OR.
     1 NIPJ.EQ.30.OR.NIPJ.EQ.32.OR.NIPJ.EQ.34.OR.NIPJ.EQ.36.OR.NIPJ.EQ.38.
     1 OR.NIPJ.EQ.40.OR.NIPJ.EQ.42.OR.NIPJ.EQ.44.OR.NIPJ.EQ.46.OR.NIPJ.EQ.
     1 48.OR.NIPJ.EQ.50.OR.NIPJ.EQ.52.OR.NIPJ.EQ.54.OR.NIPJ.EQ.56.OR.
     1 NIPJ.EQ.58.OR.NIPJ.EQ.60.OR.NIPJ.EQ.62.OR.NIPJ.EQ.64.OR.NIPJ.EQ.66
     1 .OR.NIPJ.EQ.68.OR.NIPJ.EQ.70.OR.NIPJ.EQ.72.OR.NIPJ.EQ.74.OR.NIPJ.
     1 EQ.76.OR.NIPJ.EQ.78.OR.NIPJ.EQ.80.OR.NIPJ.EQ.82.OR.NIPJ.EQ.84.OR
     1 .NIPJ.EQ.86.OR.NIPJ.EQ.88.OR.NIPJ.EQ.90.OR.NIPJ.EQ.92.OR.NIPJ.
     1 EQ.94.OR.NIPJ.EQ.96.OR.NIPJ.EQ.98.OR.NIPJ.EQ.100)THEN
             NIPG=NSCAN-NIPI+1 !FOR ZIGZAG SCAN, REVERSE BACK FOR DISPLAY
             ELSE
             NIPG=NIPI
             ENDIF
           elseif(zigans.eq.'N')then !george wood addition
           nipg=nipi  !George Wood addition
           ENDIF

TYPE *,' '
           TYPE *,' '

IF (SHAPEANS.EQ.'N')GOTO 89715
           READ(12)JJ,II,FLAG,SCANKNT !READ WHETHER 'H' OR 'S'

TYPE *,'X=',NIPG,' Y=',NIPJ,' FLAG= ',FLAG

IF (FLAG.EQ.'S')THEN

89715   READ(16,REC=I16,FMT=53)DELAYB1
        I16=I16+1
        READ(16,REC=I16,FMT=53)VOLTSETB1
        I16=I16+1
        READ(26,REC=I26,FMT=53)DELAYB2
        I26=I26+1
        READ(26,REC=I26,FMT=53)VOLTSETB2
        I26=I26+1
```

```
              READ(36,REC=I36,FMT=53)DELAYRS
              I36=I36+1
              READ(36,REC=I36,FMT=53)VOLTSETRS
              I36=I36+1
              READ(46,REC=I46,FMT=53)DELAYRNS
              I46=I46+1
              READ(46,REC=I46,FMT=53)VOLTSETRNS
              I46=I46+1
              DO 54322 IJI=1,512
54322         READ(17,REC=((I17-1)*512)+IJI,FMT=54)RAWWAVEB1(IJI)
              I17=I17+1
              DO 54323 IJI=1,512
54323         READ(27,REC=((I27-1)*512)+IJI,FMT=54)RAWWAVEB2(IJI)
              I27=I27+1
              DO 54324 IJI=1,512
54324         READ(37,REC=((I37-1)*512)+IJI,FMT=54)RAWWAVERS(IJI)
              I37=I37+1

DO 54325 IJI=1,512
54325         READ(47,REC=((I47-1)*512)+IJI,FMT=54)RAWWAVERNS(IJI)
              I47=I47+1

ELSEIF (FLAG.EQ.'H')THEN
              GOTO 1890
              ENDIF

II=II+1
              A = 0.
              DO 1400 I=1,512
              RAWWAVEB1(I)=RAWWAVEB1(I)/AVES
1400          A=A + RAWWAVEB1(I)
              ZERO = A/512.
              DO 1560 I=1,512
1560          BB1(I) = ( REAL(RAWWAVEB1(I)) - ZERO )*( VOLTSETB1 )*10./512.

II=II+1
              A = 0.
              DO 1401 I=1,512
              RAWWAVEB2(I)=RAWWAVEB2(I)/AVES
1401          A=A + RAWWAVEB2(I)
              ZERO = A/512.
              DO 1570 I=1,512
1570          BB2(I) = ( REAL(RAWWAVEB2(I)) - ZERO )*( VOLTSETB2 )*10./512.

II=II+1
              A = 0.
              DO 1402 I=1,512
              RAWWAVERS(I)=RAWWAVERS(I)/AVES
1402          A=A + RAWWAVERS(I)
              ZERO = A/512.
              DO 1580 I=1,512
1580          RRS(I) = ( REAL(RAWWAVERS(I)) - ZERO )*( VOLTSETRS )*10./512.

II=II+1
```

```
          A = 0.
          DO 1403 I=1,512
          RAWWAVERNS(I)=RAWWAVERNS(I)/AVES
     1403 A=A + RAWWAVERNS(I)
          ZERO = A/512.
          DO 1590 I=1,512
     1590 RRNS(I) = ( REAL(RAWWAVERNS(I)) - ZERO )*( VOLTSETRNS )*10./512.

IF (PHASE.EQ.'N')THEN
          CALL CORR(BB1,BB2,TWOTAU_DELAY) !for time delay in sample
          ELSEIF (PHASE.EQ.'Y')THEN  !PHASE INVERSION FOR BETWEEN B1 & B2
          CALL MCORR(BB1,BB2,TWOTAU_DELAY) !for time delay in sample
          ENDIF IF (PHASE1.EQ.'N')THEN
          CALL CORR(RRS,RRNS,DELTAT_DELAY) !for delay between reflector peaks
C                                          (sample vs. no sample)
          ELSEIF (PHASE1.EQ.'Y')THEN  !PHASE INVERSION FOR BETWEEN RN & RNS
          CALL MCORR(RRS,RRNS,DELTAT_DELAY) !for delay between reflector peaks
          ENDIF CALL OBTAIN_MAGNITUDE_SPECTRA(BB1,ASPECB1)
          CALL OBTAIN_MAGNITUDE_SPECTRA(BB2,ASPECB2)
          CALL OBTAIN_MAGNITUDE_SPECTRA(RRS,ASPECRS)
          CALL OBTAIN_MAGNITUDE_SPECTRA(RRNS,ASPECRNS)

ADELAYS = DELAYB2 - DELAYB1
          ADELAYR = DELAYRNS - DELAYRS

TWOTAU=ADELAYS+(TIMESET/51.2)*TWOTAU_DELAY !for time delay in sample
          DELTAT=ADELAYR+(TIMESET/51.2)*DELTAT_DELAY !for delay between
C                     reflector peaKS (sample vs. no sample)

CALL NOTHICK_VEL_CALC(DELTAT,TWOTAU,VEL_NOTHICK)
          type *,'vel_nothick= ',vel_nothick CALL FILTER(VEL_NOTHICK,VELPREV,CFILTER,SHAPEANS,L_VEL,U_VEL,
     1                AV_VEL,NIPG,NIPJ,SCANKNT,I18)

VEL(SCANKNT)=VEL_NOTHICK

VELPREV=VEL_NOTHICK

CALL STORE_SPECTRA(ASPECB1,ACTPOINT,I7,I7SUB)  !STORE SPECTRAS AT EACH SCAN
POINT
          CALL STORE_SPECTRA(ASPECB2,ACTPOINT,I7,I7SUB)
          CALL STORE_SPECTRA(ASPECRS,ACTPOINT,I7,I7SUB)
          CALL STORE_SPECTRA(ASPECRNS,ACTPOINT,I7,I7SUB)
```

```
1890    CONTINUE

IF (SHAPEANS.EQ.'N')SCANKNT=NPOINT
        CALL STORE_VEL(I7SUB,I85,SCANKNT,ACTPOINT,VEL) !STORE VELOCITIES AT END OF
.SPC FILE

END

SUBROUTINE STORE_VEL(I7SUB,I85,NPOINT,ACTPOINT,VEL)

C       !! STORE VELOCITIES AND FIND MAX,MIN & STORE IN CAL FILE

INTEGER*2 NPOINT,I85,ACTPOINT
        INTEGER*4 I7SUB
        REAL*4 VEL(5000)

VUP=0.0
        VLO=10.**8.
        VACCUM=0.

I7SUB=I7SUB+1
        DO 94326 IJI=1,NPOINT

VMAX=AMAX1(VUP,VEL(IJI))
        VUP=VMAX
        VMIN=AMIN1(VLO,VEL(IJI))
        VLO=VMIN
        VACCUM=VACCUM+VEL(IJI)

WRITE(7,REC=I7SUB,FMT=53)VEL(IJI)
94326   I7SUB=I7SUB+1
53      FORMAT(A4)

VAVE=VACCUM/NPOINT

WRITE(8,REC=I85,FMT=53)VUP
        I85=I85+1
        WRITE(8,REC=I85,FMT=53)VLO
        I85=I85+1
        WRITE(8,REC=I85,FMT=53)VAVE

RETURN
        END

SUBROUTINE POINT_FROM_FREQ(FREQ,TIMEPERDIV,ACTPOINT)
C
C       DETERMINE SPECTRA POINT FROM FROM SPECIFIC FREQUENCY IN SPECTRA
C
C       SEE SUBROUTINE CENTERFREQ FOR SIMILAR PROCESSING EXPLANATION
C
        INTEGER*4 DUMMYFREQ
```

```
        INTEGER*2 FREQ,ACTPOINT
        REAL*4        TIMEPERDIV,DELFREQ,TEMPPOINT
C
C
        DUMMYFREQ=FREQ*1E+06
        DELFREQ=(1./(2.*(10.*TIMEPERDIV)))
        TEMPPOINT=DUMMYFREQ/DELFREQ
        ACTPOINT=JNINT(TEMPPOINT)
C
        RETURN
        END

SUBROUTINE OBTAIN_MAGNITUDE_SPECTRA(TWAVE,DUMMY_ASPEC)
        COMPLEX      C1(1024),CSPEC(1024)
        INTEGER*4    ISTAT
        real*4       DUMMY_ASPEC(1024),PHASE(1024),TWAVE(512)

DO 500 I=1,512
500     C1(I)=CMPLX(TWAVE(I))
1580    CALL LSP$FFT_COMPLEX( C1, CSPEC, 1024,0,ISTAT )
        CALL LSP$PHASE_ANGLE( CSPEC, PHASE, DUMMY_ASPEC, 1024 )

RETURN
        END

SUBROUTINE STORE_SPECTRA(DUMMY_ASPEC,ACTPOINT,I7,I7SUB)

INTEGER*2   ACTPOINT
        INTEGER*4   REC,I7,I7SUB
        REAL*4                 DUMMY_ASPEC(1024)

DO 94326 IJI=1,ACTPOINT
        I7SUB=((I7-1)*ACTPOINT)+IJI
94326   WRITE(7,REC=I7SUB,FMT=53)DUMMY_ASPEC(IJI)
        I7=I7+1
53      FORMAT(A4)

RETURN
        END

SUBROUTINE FILTER(VEL_NOTHICK,VELPREV,CFILTER,SHAPEANS,L_VEL,U_VEL,
     1                   AV_VEL,NIPG,NIPJ,SCANKNT,I18)

CHARACTER CFILTER*1,CRUNCH_CODE*2,SHAPEANS*1
        INTEGER*2 NIPG,NIPJ,I18,SCANKNT
        REAL*4 L_VEL,U_VEL,AV_VEL
C ******** TEST FOR VELOCITY OUTSIDE FILTER LIMITS ***** C

IF (SCANKNT.EQ.1)VELPREV=AV_VEL

IF (CFILTER.EQ.'Y'.AND.(VEL_nothick.LT.L_VEL.OR.VEL_nothick.GT.U_VEL))THEN
        VEL_NOTHICK=VELPREV
        CRUNCH_CODE='BC'
```

37

```
        ICRUNCH_CODE_COUNT=1
        TYPE *,'BAD POINT AT ',NIPG,NIPJ
        ENDIF

IF (ICRUNCH_CODE_COUNT.EQ.0)CRUNCH_CODE='G'
        WRITE(76,REC=I18,FMT=53)CRUNCH_CODE
        I18=I18+1
        WRITE(76,REC=I18,FMT=53)NIPG
        I18=I18+1
        WRITE(76,REC=I18,FMT=53)NIPJ
        I18=I18+1

53      FORMAT(A4)

RETURN
        END

SUBROUTINE NOTHICK_VEL_CALC(DELTAT,TWOTAU,VEL_NOTHICK)

VELWATER=0.149   !CM/USEC

VEL_NOTHICK=VELWATER*((DELTAT/TWOTAU)+1)
        RETURN
        END

SUBROUTINE CORR(B1,B2,CXX)
C       CORRRELATE TWO WAVEFORMS
        COMPLEX*8 NC11(512),NC12(512),NC13(512)
        COMPLEX*8 NC14(512),NC15(512),NC22(512)
        REAL*4 NC16(512),B1(512),B2(512),CXX
        INTEGER*4 STATUS

DO 333 I=1,512
        NC11(I)=CMPLX(B1(I))
        NC22(I)=CMPLX(B2(I))
333     CONTINUE

CALL LSP$FFT_COMPLEX(NC11,NC12,512,0,STATUS)
        CALL LSP$FFT_COMPLEX(NC22,NC13,512,0,STATUS)

DO 777 IO=1,512
        NC14(IO)=NC12(IO)*CONJG(NC13(IO))
777     CONTINUE
        CALL LSP$FFT_COMPLEX(NC14,NC15,512,0,STATUS)
        IF (.NOT. STATUS) CALL LIB$SIGNAL(%VAL(STATUS))

AMAX=0.0
        CXX=0.0

DO 765 I=1,256
        NC16(I+256)=REAL(NC15(I))
        NC16(I)=REAL(NC15(I+256))
765     CONTINUE
```

```
            DO 881 I=1,512
            IF(NC16(I).GT.AMAX)THEN
            AMAX=NC16(I)
            CXX=I
            ENDIF
   881      CONTINUE
            CXX=CXX-257.
            RETURN
            END

SUBROUTINE MCORR(B1,B2,CXX)
C           CORRRELATE TWO WAVEFORMS !!! modified by using absolute value
C                                of minimum of correlation function
C                                  to take into account phase inversion
C                                  of B2 w/ respect to B1 such as what
C                                       happens w/ PMCs
            COMPLEX*8 NC11(512),NC12(512),NC13(512)
            COMPLEX*8 NC14(512),NC15(512),NC22(512)
            REAL*4 NC16(512),B1(512),B2(512),CXX
            INTEGER*4 STATUS DO 333 I=1,512
            NC11(I)=CMPLX(B1(I))
            NC22(I)=CMPLX(B2(I))
   333      CONTINUE CALL LSP$FFT_COMPLEX(NC11,NC12,512,0,STATUS)
            CALL LSP$FFT_COMPLEX(NC22,NC13,512,0,STATUS)

DO 777 IO=1,512
            NC14(IO)=NC12(IO)*CONJG(NC13(IO))
   777      CONTINUE
            CALL LSP$FFT_COMPLEX(NC14,NC15,512,0,STATUS)
            IF (.NOT. STATUS) CALL LIB$SIGNAL(%VAL(STATUS))

AMAX=0.0
            AMIN=1.0E+6
            CXX=0.0
            DXX=0.0

DO 765 I=1,256
            NC16(I+256)=REAL(NC15(I))
            NC16(I)=REAL(NC15(I+256))
   765      CONTINUE
            DO 881 I=1,512

C           IF(NC16(I).GT.AMAX)THEN
C           AMAX=NC16(I)
C           CXX=I
C           ENDIF

C           CORRRELATE TWO WAVEFORMS !!! modified by using absolute value
C                                of minimum of correlation function
```

```
C                             to take into account phase inversion
C                             of B2 w/ respect to B1 such as what
C                             happens w/ PMCs

IF(NC16(I).LT.AMIN)THEN
        AMIN=NC16(I)
        DXX=I
        ENDIF

881     CONTINUE

CXX=DXX

CXX=CXX-257.
        RETURN
        END
```

```
CC      PROGRAM: NOTHICK_IMAGEMAKER.FOR
C
C    Read Data file written by CRUNCH and place data into
C    "Grinnell-ready" files
C
C    Header:  X3, Y3   Dimension of scan ( SCAN DIRECTION, INDEX DIRECTION )
C             N1, N2   Number of points ( SCAN, INDEX )
C INTEGER*2     ACTPOINT
        BYTE          BFILEEXT(23)
        CHARACTER     FILENAME*44,FILEEXT*23,DRIVE*1
        CHARACTER     CALNAME*44,SELFREQANS*1,SHAPEANS*1,DISKT*5
        CHARACTER     HEAD*23,DIR*16
        EQUIVALENCE         ( FILEEXT, BFILEEXT )

JMARK=0
        I85=1

OPEN (UNIT=10,FILE='NOTHICK_DADQ1.DAT',STATUS='OLD',
   1    FORM='FORMATTED')
        READ (10,34572) FILEEXT
        READ (10,34572) DRIVE
34572   FORMAT (A)

4321    CONTINUE

HEAD=FILEEXT

IF (DRIVE.EQ.'A')DIR='DUC2:[ROTH.IMAG]'
        IF (DRIVE.EQ.'A')DISKT='DUC2:'
        IF (DRIVE.EQ.'C')DIR='DUC0:[ROTH.IMAG]'
        IF (DRIVE.EQ.'C')DISKT='DUC0:'

ICHA=0
        DO I=1,LEN(FILEEXT)
        IF (ICHA.NE.0) GOTO 98564
        IF (BFILEEXT(I).EQ.32) THEN
        ICHA=I
        FILEEXT(ICHA:ICHA+4)='.SPC'
        ENDIF
98564   END DO

FILENAME = '[ROTH.DATA]'//FILEEXT

K=0
20      K=K+1
        IF (FILEEXT(K:K).NE.'.') GOTO 20
        FILEEXT(K+1:K+3) = 'CAL'

CALNAME = '[ROTH.DATA]'//FILEEXT

CALL DONDISP1S (ICHA,FILENAME,CALNAME,HEAD,DIR,DISKT,
   1    SHAPEANS,SELFREQANS,ACTPOINT)
```

```
        CLOSE(10)
        END

SUBROUTINE DONDISP1S (ICHA,FILENAME,CALNAME,HEAD,DIR,DISKT,
     1  SHAPEANS,SELFREQANS,ACTPOINT)
C
C
C  Read Data file written by CRUNCH and write values to Grinnell
C    -UNCORRECTED & CORRECTED DATA IS DISPLAYED---
C
C  Header:  X3, Y3   Dimension of scan ( SCAN, INDEX )
C           N1, N2   Number of points ( SCAN, INDEX )
C
C
        INTEGER*4 REC,SCANPOS,XXX
        INTEGER*2 IXLENGTH_A,IXLENGTH,ACTPOINT
        INTEGER*2 X3,Y3,Y87,N1,N2,NNNNN2,NNNNN1
        INTEGER*2 DENS,NFREQ,AVES,X4,Y4,I87
        INTEGER*2 COUNT,NCOUNT,NSCAN,NINDX
        INTEGER*2 C(1024),D(460)
        INTEGER*2 SCANDIST,INDXDIST,TRFREQ,ENDFREQ,I16
        INTEGER*2 D_SHAPE(460),I89,I6,I15
        INTEGER*2 ISLANT1,ISLANT2,ISLANT3,ISLANT4,JXXX,IABC,JABC,SCANKNT
        INTEGER*2 PSEUDOGRNL(460,1024),SELFREQ
        REAL    FREQ, MEAN
        REAL    RNUP(7),RNLO(7),CBUFFER(81)
        BYTE    BSCALEMARK(4),CHFREQ(3)
        BYTE    BSUFFREQ
        BYTE    BFILENAME(44),BNAMELAB(20),BDATA_STATUS(40)
        CHARACTER FILENAME*44,FILEEXT*23,SELFREQANS*1,FFLAG*1
        CHARACTER CALNAME*44, CHEADER*32,SHAPEANS*1,ZIGANS*1
        CHARACTER NAMELAB*20,DATA_STATUS*40,NEWHEADER*35,ACTUAL_SELFREQANS*1
        CHARACTER CORNAME*15,CHFREQ_C*3,PHASE*1,PHASE1*1
        CHARACTER SCALEMARK*4,SUFFREQ*4,HEAD*23,DIR*16,DISKT*5

EQUIVALENCE ( CHFREQ, CHFREQ_C )
        EQUIVALENCE ( BNAMELAB, NAMELAB )
        EQUIVALENCE ( BDATA_STATUS, DATA_STATUS )
        EQUIVALENCE ( BSCALEMARK, SCALEMARK )
        EQUIVALENCE ( BSUFFREQ, SUFFREQ )

SCALEMARK='1 MM'
        SUFFREQ=' MHZ'
C
C       TAKE CHARACTER "FILENAME" AND DECODE TO BYTE "BFILENAME"
C

DECODE (44,533,FILENAME) BFILENAME
533     FORMAT(44A1)

C
```

```
C       DETERMINE SHORTENED (-.SPC) FILENAME POSITION
C
        I6=1
        I15=1
        I16=1

KMARK=0
        DO 4321 IPR=12,44
        IF (KMARK.EQ.1) GOTO 4321
        IF (BFILENAME(IPR).EQ.46) THEN      !PERIOD/DOT IS ASCII 46
          IEND=IPR
          KMARK=1
        ENDIF
4321    CONTINUE

34572   FORMAT (A)
34573   FORMAT (I)
51      FORMAT(A32)
52      FORMAT(A2)
53      FORMAT(A4)

OPEN( unit=15, file=FILENAME(1:IEND-1)//'.datI2', status='OLD',
     +    ACCESS='DIRECT',RECORDTYPE='FIXED',RECL=2,
     +        form='FORMATTED',ORGANIZATION='SEQUENTIAL' )

OPEN( unit=16, file=FILENAME(1:IEND-1)//'.datR4', status='OLD',
     +    ACCESS='DIRECT',RECORDTYPE='FIXED',RECL=4,
     +        form='FORMATTED',ORGANIZATION='SEQUENTIAL' )

C       OPEN( unit=26, file=FILENAME(1:IEND-1)//'.datRR4', status='OLD',
C    +    ACCESS='DIRECT',RECORDTYPE='FIXED',RECL=4,
C    +        form='FORMATTED',ORGANIZATION='SEQUENTIAL' )

OPEN( unit=66, file=FILENAME(1:IEND-1)//'.datCH', status='OLD',
     +    ACCESS='DIRECT',RECORDTYPE='FIXED',RECL=32,
     +        form='FORMATTED',ORGANIZATION='SEQUENTIAL' )

C*************UNIT=7,.SPC FILE FOR SPECTRA, vel, FOR DIRECT ACCESS*******C
C
C       OPEN( unit=7, file=FILENAME, status='OLD',ACCESS='DIRECT',
C    -    RECORDTYPE='FIXED',RECL=4,FORM='FORMATTED',
C    +        ORGANIZATION='SEQUENTIAL')

OPEN (UNIT=14,FILE='NOTHICK_SELFREQ1.DAT',
     1    STATUS='OLD',FORM='FORMATTED')

79193   READ(66,REC=I6,FMT=51)CHEADER
        I6=I6+1
        READ(66,REC=I6,FMT=51)SHAPEANS
        I6=I6+1
```

```
        READ(66,REC=I6,FMT=51)ZIGANS
        I6=I6+1

READ (14,98652) FILEEXT
        READ (14,98652) DRIVE
        READ (14,98652) PHASE
        READ (14,98652) PHASE1
        READ (14,98652) DIFFANS
        READ (14,10030) BUFLENGTH
        READ (14,10030) BUFVEL
        READ (14,10030) TRDIAM
        CLOSE (14)
98652   FORMAT (A)
10020   FORMAT (I)
10030   FORMAT (F)

89714   READ(15,REC=I15,FMT=52)SCANDIST
        I15=I15+1
        READ(15,REC=I15,FMT=52)INDXDIST
        I15=I15+1
        READ(15,REC=I15,FMT=52)NSCAN
        I15=I15+1
        READ(15,REC=I15,FMT=52)NINDX
        I15=I15+1
        READ(15,REC=I15,FMT=52)islant1
        I15=I15+1
        READ(15,REC=I15,FMT=52)islant2
        I15=I15+1
        READ(15,REC=I15,FMT=52)islant3
        I15=I15+1
        READ(15,REC=I15,FMT=52)islant4
        I15=I15+1
        READ(15,REC=I15,FMT=52)DENS
        I15=I15+1
        READ(15,REC=I15,FMT=52)TRFREQ
        I15=I15+1
        READ(15,REC=I15,FMT=52)AVES
        I15=I15+1
        READ(15,REC=I15,FMT=52)JXXX
        I15=I15+1
C       ARRAYSIZE=(NSCAN)*(JXXX) !IF SCAN FINISHED PROPERLY,JXXX=NINDX

ENCODE (3,19878,CHFREQ) TRFREQ  !ANALYSIS FREQUENCY
19878   FORMAT (I3)

READ(16,REC=I16,FMT=53)TIMESET
        I16=I16+1

ENDFREQ=2.5*TRFREQ
        CALL POINT_FROM_FREQ(ENDFREQ,TIMESET,ACTPOINT)
```

```
        DO 9999 ICHOICE=1,1
        I87=1

ACCUM=0.
        NBAD=0
            IF (ICHOICE.EQ.1) THEN
                    NAMELAB='VELOCITY  CM/US'
                    CORNAME='_VEL_C_'//CHFREQ_C
                NEWHEADER='CORRECTED DATA FOR VELOCITY'
                    NEWU=25
                    NEWU1=45
                    NEWU2=69
            ENDIF

OPEN (UNIT=NEWU1,FILE=DISKT//FILENAME(1:IEND-1)//CORNAME//
     +   '.CORHEADER',STATUS='NEW',FORM='UNFORMATTED')

12345   IF (JMARK.EQ.1) GOTO 90 !FILES ARE ALREADY OPEN

30      CONTINUE

90      CONTINUE

IF (JMARK.EQ.1) GOTO 89306

10149   CONTINUE

IF (SHAPEANS.NE.'Y')GOTO 89317
        OPEN(UNIT=52,FILE=FILENAME(1:ICHA+10)//'.DATHS',
     1  STATUS='OLD',FORM='UNFORMATTED') !INFO ON WHETHER WE ARE ON HOLDER/SAMPLE

89317   SCANDIST=ABS(SCANDIST)
        AD=NSCAN
        XREAL = REAL(ABS(SCANDIST))
        YREAL = REAL(INDXDIST)
        NPTS = NSCAN*JXXX !!!!IF SCAN COMPLETED PROPERLY, JXXX=NINDX

IF (SHAPEANS.EQ.'Y')THEN
        DO 5697 I=1,NPTS
5697    READ(UNIT=52, END=89318)IABC,JABC,FFLAG,SCANKNT
        ENDIF

89318   PTS  = REAL(NSCAN)*REAL(JXXX)
        X3=ABS(SCANDIST)
        Y3=INDXDIST
        N1=NSCAN
        N2=JXXX
        IF (I.EQ.1) THEN
        NNNNN1=N1
        NNNNN2=N2
        ENDIF
```

```
            XREAL = REAL(ABS(X3))
            YREAL = REAL(Y3)
            FREQ  = REAL(NFREQ)
            PTS   = REAL(N1)*REAL(N2)

C
C  Proportion GRINNELL window similar to scan dimensions
C

200    Y87 = ININT( REAL(Y3)*8./7. )
        IF( Y87.GE.X3 )THEN
                R1 = FLOAT(X3)/FLOAT(Y3)
                X4 = 400
                Y4 = ININT(400./R1)
                IF (Y4.GE.480)THEN
                X4=300
                Y4 = ININT(300./R1)
                ENDIF
                IF (Y4.GE.480)THEN
                X4=200
                Y4 = ININT(200./R1)
                ENDIF
                IF (Y4.GE.480)THEN
                X4=100
                Y4 = ININT(100./R1)
                ENDIF
            IF (Y4.GE.480)THEN
                X4=50
                Y4 = ININT(50./R1)
                ENDIF
            IF (Y4.GE.480)THEN
                X4=25
                Y4 = ININT(25./R1)
                ENDIF
        IF (Y4.GE.480)THEN
                X4=10
                Y4 = ININT(10./R1)
                ENDIF
            ELSEIF( Y87.LT.X3 ) THEN
                R1 = FLOAT(Y3) / FLOAT(X3)
                Y4 = IFIX( 400.*R1 )
        X4 = 400
                IF (Y4.GE.480)THEN
                X4=300
                Y4 = ININT(300.*R1)
                ENDIF
                IF (Y4.GE.480)THEN
                X4=200
                Y4 = ININT(200.*R1)
                ENDIF
                IF (Y4.GE.480)THEN
                X4=100
                Y4 = ININT(100.*R1)
                ENDIF
                IF (Y4.GE.480)THEN
```

```
            X4=50
            Y4 = ININT(50.*R1)
            ENDIF
        IF (Y4.GE.480)THEN
            X4=25
            Y4 = ININT(25.*R1)
            ENDIF
        IF (Y4.GE.480)THEN
            X4=10
            Y4 = ININT(10.*R1)
            ENDIF
    ENDIF

CC

XD2G = REAL(N1)/REAL(X4)
        YD2G = REAL(N2)/REAL(Y4)

XD2X = REAL(X4)/REAL(N1)
        YD2Y = REAL(Y4)/REAL(N2)

I_INT=JINT(XD2X)-1
        J_INT=JINT(YD2Y)+1

89306   CONTINUE 10300   format( //'$Enter choice :')

54322   FORMAT (A)
4319    FORMAT ('+','VALUE=',F)

TYPE *,' '
        TYPE *,'Working...'
        TYPE *,' '

43191   FORMAT ('+','BAD PTS/TOT. PTS:',I5,'/',I4,
    +            ' CURRENT VALUE= ',F11.2)
7493    FORMAT (F11.2)
7494    FORMAT(I)

C
C       RETURN MAX/MIN OF DATA FOR GRINNELL DISPLAY & PRODUCE LINE
C       OF GRINNELL DATA (CBUFFER)

CALL RETMAXMIN_FILTER (FILENAME,CORNAME,CALNAME,NAMELAB,DISKT,IEND,JXXX,
    1
NSCAN,SCANKNT,SHAPEANS,ZIGANS,ICHOICE,TIMESET,I89,COUNT,ACTPOINT,NEWU,GRBOT,
    1   GRTOP,MEAN)

7487    COUNT=NCOUNT
        RMIN=GRBOT
        RMAX=GRTOP
        I87=1
```

```
              RNLO(ICHOICE)=RMIN
              RNUP(ICHOICE)=RMAX

DO 500 KI=1,JXXX
              DO 49721 JI=1,NSCAN
              NIPI=JI
              NIPJ=KI
              SCANPOS=((NIPJ-1)*NSCAN)+NIPI
              I87=SCANPOS
              READ (NEWU,REC=I87,FMT=53) CBUFFER(JI)
49721         I87=I87+1
462           FORMAT (F11.2)
              CALL SCGREAL (CBUFFER, C, N1,GRBOT,GRTOP,MEAN) !GREY SCALED
              DATA_STATUS='CORRECTED DATA FOR '//NAMELAB
C
C             INTERPOLATE DATA GRID (EX.81X81) FOR X4 x Y4 GRINNELL DISPLAY
C
              CALL INTR ( C,D,NSCAN,X4 )

C     IF (KI.EQ.20)TYPE *,'D=',D

C ********** MOD TO GET RID OF FALSE BORDER **************** C
              IF (SHAPEANS.EQ.'Y')THEN

IIXCOUNT=0
              DO 555 IOP=1,X4 !FORWARD X-DIRECTION
              IF (D(IOP).EQ.1)GOTO 555
              IIXCOUNT=IIXCOUNT+1
              IF (IIXCOUNT.EQ.1)THEN
              DO 655 IJQ=1,I_INT
655           D(IOP+IJQ-1)=1
              ENDIF
555           CONTINUE

IIXCOUNT=0
              DO 755 IOP=X4,1,-1 !BACKWARD X-DIRECTION
              IF (D(IOP).EQ.1)GOTO 755
              IIXCOUNT=IIXCOUNT+1
              IF (IIXCOUNT.EQ.1)THEN
              DO 855 IJQ=1,I_INT
855           D(IOP-IJQ+1)=1
              ENDIF
755           CONTINUE

C     IF (KI.EQ.20)TYPE *,'D=',D

ENDIF

C ********** MOD TO GET RID OF FALSE BORDER ********** C

DO 480 J= 1, X4
480           PSEUDOGRNL( J,NIPJ ) = D( J )
500           CONTINUE
```

```
CC
        OPEN (UNIT=NEWU2, FILE=DIR//HEAD//CORNAME//'.PDK',STATUS='NEW',
      +        FORM='UNFORMATTED')

WRITE(NEWU2) X4,Y4,N1,N2,ICHOICE
        WRITE(NEWU2) SCANDIST,TRFREQ
        WRITE(NEWU2) RMIN,RMAX,MEAN

TYPE *,X4,Y4,N1,N2,ICHOICE
        TYPE *,SCANDIST,TRFREQ
        TYPE *,RMIN,RMAX,MEAN

IXLENGTH=0
605     DO 800  IJ= 1, X4
        IX = IJ-1

DO 540  J= 1, N2
540     C( J ) = PSEUDOGRNL( IJ,J )

CALL INTR ( C,D,JXXX,Y4 )

C       IF (IJ.EQ.200)TYPE *,'D=',D

C ********** MOD TO GET RID OF FALSE BORDER **************** C
        IF (SHAPEANS.EQ.'Y')THEN

IIXCOUNT=0
        DO 1555 IOP=1,Y4  !FORWARD Y-DIRECTION
        IF (D(IOP).EQ.1)GOTO 1555
        IIXCOUNT=IIXCOUNT+1
        IF (IIXCOUNT.EQ.1)THEN
        DO 1655 IJQ=1,J_INT
1655    D(IOP+IJQ-1)=1
        ENDIF
1555    CONTINUE

IIXCOUNT=0
        DO 1755 IOP=Y4,1,-1  !BACKWARD Y-DIRECTION
        IF (D(IOP).EQ.1)GOTO 1755
        IIXCOUNT=IIXCOUNT+1
        IF (IIXCOUNT.EQ.1)THEN
        DO 1855 IJQ=1,J_INT
1855    D(IOP-IJQ+1)=1
        ENDIF
1755    CONTINUE

C       IF (IJ.EQ.200)TYPE *,'D=',D

ENDIF

C ********** MOD TO GET RID OF FALSE BORDER ********* C
```

```
C************MODIFICATION FOR COMPLEX SHAPE **********C

IF (SHAPEANS.NE.'Y')GOTO 675  !NOT A COMPLEX SHAPE
        IF (SHAPEANS.EQ.'Y')THEN

XXX=1
        IXSTART=IJ
        IYLENGTH=0
        NKEEP=0
        DO 8970 J=1,Y4
        IF (D(J).LT.2)GOTO 8970  !1 IS CODED FOR LUCITE (IN SCGREAL)
        IF (D(J).GE.2)THEN  !SAMPLE DATA
        IF (NKEEP.EQ.0)IYSTART=J
        NKEEP=1
C**** FURTHER MOD FOR GEORGE'S DISCONTINUITY ON YBCO HEX SAMPLE ******
        IF (IYLENGTH.GT.1.AND.D(J).GE.2.AND.D(J-1).LT.2)THEN
8875    XXX=XXX+1
        IYLENGTH=IYLENGTH+1
        D_SHAPE(IYLENGTH)=1
        IF (D(J-XXX).LT.2)GOTO 8875
        ENDIF
C**** FURTHER MOD FOR GEORGE'S DISCONTINUITY ON YBCO HEX SAMPLE ******
        IYLENGTH=IYLENGTH+1
        D_SHAPE(IYLENGTH)=D(J)
        ENDIF
8970    CONTINUE
C       TYPE *,'IXSTART=',IXSTART,'IYSTART=',IYSTART,'IYLENGTH=',
C    1   IYLENGTH
        IF (IYLENGTH.EQ.0)GOTO 800   !ALL LUCITE IN THIS COLUMN
        IXLENGTH=IXLENGTH+1
        WRITE(NEWU2)IXSTART,IYSTART,IYLENGTH
        DO 8979 IJK=1,IYLENGTH
8979    WRITE(NEWU2)D_SHAPE(IJK)
        GOTO 800
        ENDIF
C ************************************************************ C

675     WRITE(NEWU2) D

800     CONTINUE

TYPE *,' '
        TYPE *,' HIGHEST ',NAMELAB,' IS ',RMAX
        TYPE *,' LOWEST ',NAMELAB,' IS ',RMIN
        TYPE *,' '

WRITE (NEWU1)NEWHEADER
        WRITE (NEWU1)RMIN,RMAX
        WRITE (NEWU1)MEAN
        WRITE (NEWU1) ISCALEF
```

```
97364   FORMAT (A)
        CLOSE (NEWU)
        CLOSE (NEWU1)
        CLOSE (NEWU2)
        TYPE *,'DONE CLOSING ', HEAD//CORNAME//'.PDK'

JMARK=1

IF (SHAPEANS.NE.'Y')GOTO 9999
5001    REWIND(52)
9999    CONTINUE
        IXLENGTH_A=IXLENGTH
        WRITE(15,REC=I15,FMT=52)IXLENGTH_A
        CLOSE(15)

CLOSE(52)
87124   CONTINUE

CLOSE (6)

RETURN
        end

C
C   GRNLBASE.FOR
C        - A set of subroutines useful for applications
C        with the GRINNELL image processor.
C        GRINIT must be called in main program before calling these
C        subroutines.
C
C
C        David B. Stang      latest update  19-APR-88

SUBROUTINE SCGREAL( CC,DD, N, BOT,TOP,MEAN )
C
C   Convert values in CC to 1 thru 255 ( same as SCGR, with CC REAL )
C
C          CC( N )      Input Data
C          DD( N )         Output Data
C       BOT       Desired Min for Gray Scale ( units of CC )
C       TOP       Desired Max for Gray Scale        "

INTEGER*2    N
        INTEGER*2    DD(N)
        REAL         CC(N),MEAN

RAN = TOP - BOT
        IF (RAN.EQ.0.)RAN=1.
        DO 2000 J = 1,N
        C0 = CC(J)
        Q = ( C0 - BOT ) / RAN
        IF ( Q.LE.0.) Q = 0.
        IF ( Q.GT.1.) Q = 1.
```

```
      Q = Q*251.
C     DD(J) =NINT( Q )+1
C***** FOR MY MODIFICATION **************C
      IF (C0.EQ.0.)THEN
      DD(J)=1
      GOTO 2000
      ELSEIF (C0.NE.0.)THEN
      DD(J)=NINT(Q)+2
      ENDIF
C*****************************************C
2000  CONTINUE

RETURN
      END

CC    SUBROUTINE INTR
CC
CC    Interpolate values in C(N2) to "fit" into D(NN)
C
C     SUBROUTINE INTR ( CC,DD,N2,NN )
C
C     INTEGER*2    N2,NN
C     INTEGER*2    CC(N2), DD(NN)
C
C     RN = FLOAT(N2) / FLOAT(NN)
C
C     DO 3000  K = 1,NN
C     R = FLOAT( K )* RN
C     IR = IFIX( R )
C     IR = IINT( R )
C     IRP1 = IR+1
C     RR = R - FLOAT( IR )
C       IF( IR.LT.1 ) IR=1
C     IF( NN.GT.N2 .AND. IRP1.GT.NN ) THEN
C                   IR=NN-1
C                   IRP1=NN
C       ENDIF
C     C0 = FLOAT( CC(IR) )
C     C1 = FLOAT( CC(IRP1) )
C     D0 = ( 1.-RR )*C0  +  RR * C1
C 3000 DD(K) = IFIX(D0)
C 3000 DD(K) = IINT(D0)
C
C     RETURN
C     END SUBROUTINE RETMAXMIN_FILTER(FILENAME,CORNAME,CALNAME,NAMELAB,DISKT,
    1  IEND,JXXX,NSCAN,SCANKNT,SHAPEANS,ZIGANS,ICHOICE,TIMESET,I89,
    1  COUNT,ACTPOINT,NEWU,GRBOT,GRTOP,MEAN)

INTEGER*4  REC,SCANPOS,I7
      INTEGER*2  NSCAN,ACTPOINT
```

```
      INTEGER*2 I85,I87,SCANKNT
      INTEGER*2 IABC,JABC,JXXX,I89
      INTEGER*2 NCOUNT
      INTEGER*2 ZIGCOUNT
      INTEGER*2 NBAD,COUNT,LCOUNTER
      REAL    DATATHING(1024,9)
      REAL    MEAN,VEL(5000)
      REAL    CBUFFER(81)
      CHARACTER FILENAME*44,CORNAME*15,NAMELAB*20,FFLAG*1
      CHARACTER SHAPEANS*1,ZIGANS*1,DISKT*5,CALNAME*44
      INTEGER*4 SCANPOS1

TYPE *,NAMELAB
      LCOUNTER=1
      ZIGCOUNT=1
      ACCUM=0.
      SCANPOS=0
      SCANPOS1=0
      NBAD=COUNT
      I87=1
 11   XMAX=0.
      XMIN=10000000.
      PTS = REAL(NSCAN)*REAL(JXXX)
      NPTS=NSCAN*JXXX

C     CAL FILE WITH MAX/MIN/MEAN
C
      OPEN( unit=8, file=CALNAME, status='OLD', ACCESS='DIRECT',
     +  RECORDTYPE='FIXED',RECL=4,FORM='FORMATTED',
     +    ORGANIZATION='SEQUENTIAL' )
      I85=1 read(8,REC=I85,FMT=53)VUP
      I85=I85+1
      read(8,REC=I85,FMT=53)VLO
      I85=I85+1
      read(8,REC=I85,FMT=53)VAVE

IF (SHAPEANS.EQ.'Y')THEN
      NPTS=SCANKNT
      REWIND(52)
      ENDIF

I7=NPTS*4*ACTPOINT+1  !START OF VELOCITY READS IN .SPC FILE
C
C     SPC FILE (UNIT=7) CONTAINS ALL VELOCITY & SPECTRA DATA

OPEN (UNIT=7,FILE=DISKT//FILENAME,STATUS='OLD',ACCESS='DIRECT',
     +      RECORDTYPE='FIXED',RECL=4,FORM='FORMATTED',
     +      ORGANIZATION='SEQUENTIAL')

OPEN (UNIT=NEWU,FILE=DISKT//FILENAME(1:IEND-1)//CORNAME//'.COR',
```

```
     +       STATUS='NEW',ACCESS='DIRECT',
     +             RECORDTYPE='FIXED',RECL=4,FORM='FORMATTED',
     +             ORGANIZATION='SEQUENTIAL')

DO 500 NIPJ=1,JXXX
      410    DO 450 NIPI=1,NSCAN

C***** GET INFO FROM HOLDER.DAT (FFLAG='S' -> SAMPLE) (FFLAG='H' -> HOLDER)
             KCON=KCON+1
             J=NIPI
             SCANPOS1=((NIPJ-1)*NSCAN)+NIPI  !TRUE SCAN POSITION
             IF (SHAPEANS.NE.'Y')GOTO 87123
             READ(52)IABC,JABC,FFLAG,SCANKNT
C            TYPE *,'XH=',IABC,' YH=',JABC,' FFLAG=',FFLAG
             IF (FFLAG.NE.'S')GOTO 8702 !TRANSDUCER IS ON HOLDER/GOTO NEXT PT.
     87123   SCANPOS=SCANPOS+1
CC    !! 'SCANPOS' FOR FILE RETRIEVAL FOR CIRCLE DISK SCANS
             READ(7,REC=I7,FMT=53)VEL(SCANPOS)
             I7=I7+1

DATATHING(J,5)=VEL(SCANPOS)

NPTS=(NIPJ-1)*NSCAN+NIPI
                   IF (NPTS.EQ.NSCAN*JXXX)NPTS=NSCAN*JXXX

C            IF (ICHOICE.EQ.1)THEN
                   IF (SCANPOS.EQ.1)DATATHINGPREVIOUS=VAVE
C                  IF (DATATHING(J,5).LT.(VLO+VLO*0.001).OR.
C       1    DATATHING(J,5).GT.(VUP-VUP*0.001))DATATHING(J,5)=DATATHINGPREVIOUS
C            ENDIF

IF (SHAPEANS.NE.'Y')GOTO 87651
     8702    IF (FFLAG.NE.'S')THEN !SET TO 0 // TRANSDUCER IS ON HOLDER/GOTO NEXT PT.

CBUFFER(J)=0.0

GOTO 450
             ENDIF

87651   CBUFFER(J)=DATATHING(J,5)

390     CONTINUE

C******KEEP TRACK OF MAX & MIN LIMITS OF CORRECTED DATA********C
C **** FOR FFLAG.NE.'S' --- WE SKIP THIS STEP SO THAT '0' IS NOT CONSIDERED
             RMAX=AMAX1(CBUFFER(J),XMAX)
             RMIN=AMIN1(CBUFFER(J),XMIN)
             XMAX=RMAX
             XMIN=RMIN
```

```
         DATATHINGPREVIOUS=CBUFFER(J)

450      CONTINUE

IF (ZIGANS.EQ.'N')THEN   !NOT A ZIGZAG SCAN - A NORMAL SCAN
         DO 49720 JI=1,NSCAN
         WRITE (NEWU,REC=I87,FMT=53) CBUFFER(JI)
         ACCUM=ACCUM + CBUFFER(JI)
49720    I87=I87+1

ELSEIF (ZIGANS.EQ.'Y'.AND.ZIGCOUNT.EQ.1)THEN !ZIGZAG/LEFT->RIGHT
         DO 49721 JI=1,NSCAN
         WRITE (NEWU,REC=I87,FMT=53) CBUFFER(JI)
         ACCUM=ACCUM + CBUFFER(JI)
C        TYPE *,'CBUFFER(JI)=',CBUFFER(JI)
49721    I87=I87+1

ELSEIF (ZIGANS.EQ.'Y'.AND.ZIGCOUNT.EQ.0)THEN !ZIGZAG/RIGHT->LEFT
         DO 49722 JI=NSCAN,1,-1
         WRITE (NEWU,REC=I87,FMT=53) CBUFFER(JI)
         ACCUM=ACCUM + CBUFFER(JI)
C        TYPE *,'CBUFFER(JI)=',CBUFFER(JI)
49722    I87=I87+1
         ENDIF

C***** FOR ZIGZAG SCANS - TO ALTER ROW STORAGE **********C
         IF (ZIGANS.EQ.'Y'.AND.ZIGCOUNT.EQ.1)THEN
         ZIGCOUNT=0
         GOTO 500
         ELSEIF (ZIGANS.EQ.'Y'.AND.ZIGCOUNT.EQ.0)THEN
         ZIGCOUNT=1
         ENDIF

C500     TYPE *,'Y=',JABC,'CBUFFER=',CBUFFER
500      CONTINUE
5001     GRBOT = RMIN
         GRTOP = RMAX

TYPE *,' '
         TYPE *,'RMIN=',GRBOT
         TYPE *,'RMAX=',GRTOP
         MEAN = ACCUM/SCANPOS
         TYPE *,'MEAN=',MEAN
         IF (SHAPEANS.NE.'Y')GOTO 88888
         REWIND(52)

88888    CONTINUE
53       FORMAT (A4)
43191    FORMAT ('+','BAD PTS =',I5,' AT LOCATION (SCANPOS) =',I5)
         RETURN
         END

SUBROUTINE POINT_FROM_FREQ(SELFREQ,TIMEPERDIV,ACTPOINT)
C
```

```
C       DETERMINE SPECTRA POINT FROM FROM SPECIFIC FREQUENCY IN SPECTRA
C
C       SEE SUBROUTINE CENTERFREQ FOR SIMILAR PROCESSING EXPLANATION
C
        INTEGER*4 DUMMYFREQ
        INTEGER*2 SELFREQ,ACTPOINT
        REAL*4       TIMEPERDIV,DELFREQ,TEMPPOINT
C
C
        DUMMYFREQ=SELFREQ*1E+06
        DELFREQ=(1./(2.*(10.*TIMEPERDIV)))
        TEMPPOINT=DUMMYFREQ/DELFREQ
        ACTPOINT=JNINT(TEMPPOINT)
C
        RETURN
        END

SUBROUTINE CENTERFREQ(DUMMYP,TIMEPERDIV,ACTFREQ)
C
C       DETERMINE FREQUENCY FROM POINT IN B1(F) SPECTRA
C
        INTEGER*2 DUMMYP,ACTFREQ
        REAL*4       TIMEPERDIV,DELFREQ,TEMPFREQ
C
C       WE KNOW THAT DELFREQ=(1/(2N*DELTIME))
C                    =(1/(2N*(10*TIMEPERDIV/N)))
C                    =(1/(2*(10*TIMPERDIV)))
C
C       WHERE N = 512 POINTS/ACQUISITION (SCREEN)
C          TIMEPERDIV = TIME SETTING PER DIVISION (EX. 50 NSEC)
C          2 = WE EXTENDED 512 ARRAY TO 1024 ARRAY FOR PROCESSING
C          10 = THE NUMBER OF DIVISIONS/SCREEN
C
C       FOR EXAMPLE:
C        WE CAN DETERMINE THE FREQUENCY FOR WHICH THE POINT "MAXB1P"
C       CORRESPONDS TO BY JUST MULTIPLYING (DELFREQ) * (MAXB1P)
C
        DELFREQ=(1./(2.*(10.*TIMEPERDIV)))
        TEMPFREQ=DELFREQ*DUMMYP
        TEMPFREQ=TEMPFREQ/1E+06
        ACTFREQ=JNINT(TEMPFREQ)
C       TYPE *,' '
C       TYPE *,'POINT=',DUMMYP,' FREQ=',ACTFREQ,' MHZ'
C       TYPE *,' '
C
        RETURN
        END
C
C
C
C
C
        SUBROUTINE INTR (F1, F2, N, M)
C
C
```

```
        IMPLICIT NONE
C
        INTEGER*2 I, M, N
        INTEGER*2 F1(N), F2(M)
        REAL*4 X, XA(512), Y, YA(512)
C
C
        DO I = 1, N
          XA(I) = FLOATI(I)
        END DO
C
        DO I = 1, N
          YA(I) = FLOATI(F1(I))
        END DO
C
        DO I = 1, M
          X = FLOATI(I-1) * FLOATI(N-1) / FLOATI(M-1) + 1.0
          CALL LINEAR_INTERPOLATION (XA, YA, N, X, Y)
          F2(I) = ININT(Y)
        END DO
C
C
        RETURN
        END
C
C       LINEAR_INTERPOLATION computes the value of the piecewise linear spline
C                interpolant of the points in the arrays XA and YA at the point
C                X. This routine is a modified version of the FORTRAN routine
C                SPLINT found in the book "Numerical Recipes: The Art of
C                Scientific Computing" by Press, Flannery, Teukolsky, and
C                Vetterling published by the Cambridge University Press, 1986.
C
C       Variables:
C
C                NMAX : A constant which determines the array sizes
C                       for U, X, and Y.
C                K : The midpoint between KHI and KLO... used to find the two
C                       indices into the XA table such that
C                       XA(KLO) < X < XA(KHI).
C                KHI : The greater of the two indices into the XA array such
C                       that XA(KLO) < X < XA(KHI).
C                KLO : The lesser of the two indices into the XA array such
C                       that XA(KLO) < X < XA(KHI).
C                N : The index of the arrays and Y that contain interpolation
C                       points.
C                A : Weight given to YA(KLO).
C                B : Weight given to YA(KHI).
C                H : The difference of XA(KHI) and XA(KLO).
C                X : The value of X at which to compute the value of the
C                       interpolation function.
C                XA : The table of X coordinates of the interpolation points.
C                Y : The value of the interpolation function evaluated at X.
C                YA : The table of Y coordinates of the interpolation points.
C
        SUBROUTINE LINEAR_INTERPOLATION (XA, YA, N, X, Y)
```

```
C
C
        IMPLICIT NONE
C
        INTEGER NMAX
        PARAMETER (NMAX=512)
C
        INTEGER*2 K, KHI, KLO, N
        REAL*4 A, B, H
        REAL*4 X, XA(NMAX), Y, YA(NMAX)
C
C
        KLO = 1
        KHI = N
        DO WHILE (KHI-KLO.GT.1)
        K = (KHI + KLO) / 2
        IF (XA(K).GT.X) THEN
           KHI = K
        ELSE
           KLO = K
        END IF
        END DO
C
        H = XA(KHI) - XA(KLO)
        IF (H.NE.0.0) THEN
           A = (XA(KHI) - X) / H
           B = (X - XA(KLO)) / H
           Y = A * YA(KLO) + B * YA(KHI)
        END IF
C
C
        RETURN
        END
```

```
C ***** NOTHICK_DRAW.FOR ******************C

INTEGER*2   TRFREQ,JXXX,IXLENGTH
      INTEGER*2   SCANDIST,INDXDIST,NSCAN,NINDX,DENS
      INTEGER*2   SELFREQ,AVES,I6,I15,ISLANT1,ISLANT2,ISLANT3,ISLANT4
      CHARACTER   RESP1*1,SELFREQANS*1,RESP2*2
      CHARACTER   NEWOLD*3,SHAPEANS*1,ZIGANS*1,CHFREQ_C*3,CHDRI*1
      BYTE        B, CHFREQ(3), BSUFFREQ(4)
      BYTE        BSCALEMARK(4)
      BYTE        BDATA_STATUS(40), BLABEL(30), BFILEEXT(23)
      CHARACTER   LABEL*30, FILEEXT*23,CHEADER*32,TEBAR*1
      CHARACTER   L*48, DIR*16,DRIVE*1,NOISANS*1,DIFFANS*1
      CHARACTER   SUFFREQ*4,FILENAME*34,SCALEMARK*4,DATA_STATUS*40
      CHARACTER   ACTUAL_SELFREQANS*1,SASANS*1,PHASE*1,PHASE1*1

EQUIVALENCE ( BFILEEXT,FILEEXT )
      EQUIVALENCE ( CHFREQ,CHFREQ_C )
      EQUIVALENCE ( L,B )
      EQUIVALENCE ( BSCALEMARK, SCALEMARK )
      EQUIVALENCE ( BSUFFREQ, SUFFREQ )
      EQUIVALENCE ( BDATA_STATUS, DATA_STATUS )
      EQUIVALENCE ( BLABEL, LABEL )

NEWOLD='OLD'

OPEN (UNIT=10,FILE='NOTHICK_DADQ1.DAT',STATUS=NEWOLD,
     1FORM='FORMATTED')

READ (10,511) FILEEXT
      READ (10,511) DRIVE
511   FORMAT (A)
51    FORMAT (A32)
52    FORMAT (A2)
53    FORMAT (A4)
677   FORMAT (I)

OPEN( unit=66, file='[ROTH.DATA]'//FILEEXT//'.datCH', status='OLD',
     +     ACCESS='DIRECT',RECORDTYPE='FIXED',RECL=32,
     +          form='FORMATTED',ORGANIZATION='SEQUENTIAL' )

OPEN (UNIT=14,FILE='NOTHICK_SELFREQ1.DAT',
     1 STATUS='OLD',FORM='FORMATTED')

OPEN( unit=15, file='[ROTH.DATA]'//FILEEXT//'.datI2', status='OLD',
     1    ACCESS='DIRECT',RECORDTYPE='FIXED',RECL=2,
     +          form='FORMATTED',ORGANIZATION='SEQUENTIAL' )

I6=1
79193 READ(66,REC=I6,FMT=51)CHEADER
      I6=I6+1
      READ(66,REC=I6,FMT=51)SHAPEANS
      I6=I6+1
      READ(66,REC=I6,FMT=51)ZIGANS
```

```
        I6=I6+1

READ (14,98652) FILEEXT
        READ (14,98652) DRIVE
        READ (14,98652) PHASE
        READ (14,98652) PHASE1
        READ (14,98652) DIFFANS
        READ (14,10030) BUFLENGTH
        READ (14,10030) BUFVEL
        READ (14,10030) TRDIAM
        CLOSE (14)
98652   FORMAT (A)
10020   FORMAT (I)
10030   FORMAT (F)

I15=1
89714   READ(15,REC=I15,FMT=52)SCANDIST
        I15=I15+1
        READ(15,REC=I15,FMT=52)INDXDIST
        I15=I15+1
        READ(15,REC=I15,FMT=52)NSCAN
        I15=I15+1
        READ(15,REC=I15,FMT=52)NINDX
        I15=I15+1
        READ(15,REC=I15,FMT=52)islant1
        I15=I15+1
        READ(15,REC=I15,FMT=52)islant2
        I15=I15+1
        READ(15,REC=I15,FMT=52)islant3
        I15=I15+1
        READ(15,REC=I15,FMT=52)islant4
        I15=I15+1
        READ(15,REC=I15,FMT=52)DENS
        I15=I15+1
        READ(15,REC=I15,FMT=52)TRFREQ
        I15=I15+1
        READ(15,REC=I15,FMT=52)AVES
        I15=I15+1
        READ(15,REC=I15,FMT=52)JXXX
        I15=I15+1
        READ(15,REC=I15,FMT=52)IXLENGTH
C       ARRAYSIZE=(NSCAN)*(JXXX) !IF SCAN FINISHED PROPERLY,JXXX=NINDX

ENCODE (3,19878,CIIFREQ) TRFREQ  !ANALYSIS FREQUENCY
19878   FORMAT (I3)

C       DETERMINE SHORTENED (-.DAT) FILEEXT POSITION
C
C       KMARK=0
C       DO 4321 IPR=1,34
C       IF (KMARK.EQ.1) GOTO 4321
```

```
C       IF (BFILEEXT(IPR).EQ.46) THEN        !PERIOD/DOT IS ASCII 46
C       IEND=IPR
C       KMARK=1
C       ENDIF
C4321   CONTINUE
C       FILEEXT=FILEEXT(1:IEND-1)

TYPE *,' CURRENT IMAGE FILE IS ',FILEEXT
        TYPE *,' '
        TYPE *,' IF YOU WANT A DIFFERENT IMAGE FILE, YOU MUST'
        TYPE *,' RECALL AN OLDER "NOTHICK_DADQ1.DAT" FILE'
        TYPE *,' '

IF (DRIVE.EQ.'A')DIR='DUC2:[ROTH.IMAG]'
        IF (DRIVE.EQ.'C')DIR='DUC0:[ROTH.IMAG]'

5321    TYPE *,'CURRENT DRIVE TO READ IMAGES IS ',DIR(1:5)

IF (DIR(1:5).EQ.'DUC0:')THEN
        TYPE *,'DO YOU WANT TO CHANGE TO DUC2: (Y/N
     1  )?'
        READ (5,51)CHDRI
        IF (CHDRI.NE.'Y'.AND.CHDRI.NE.'N')GOTO 5321
        IF (CHDRI.EQ.'Y')DIR='DUC2:[ROTH.IMAG]'
        ELSEIF (DIR(1:5).EQ.'DUC2:')THEN
        TYPE *,'DO YOU WANT TO CHANGE TO DUC0: (Y/N
     1  )?'
        READ (5,51)CHDRI
        IF (CHDRI.NE.'Y'.AND.CHDRI.NE.'N')GOTO 5321
        IF (CHDRI.EQ.'Y')DIR='DUC0:[ROTH.IMAG]'
        ENDIF

211     TYPE *,' '
        TYPE *,' DO YOU WANT TO SEE TEXT AND COLORBAR (Y/N)?'
        READ (5,51)TEBAR
        IF (TEBAR.NE.'Y'.AND.TEBAR.NE.'N')GOTO 211
        CONTINUE

FILENAME='[ROTH.DATA]'//FILEEXT

CALL GRINIT
        CALL GRSRST

TYPE *,' '
        TYPE *,'IMAGE FREQUENCY (MHz) = ',TRFREQ
        ENCODE (3,9878,CHFREQ) TRFREQ
9878    FORMAT (I3)

234     TYPE *,' ****** NOTHICKNESS VELOCITY IMAGE ****** '
        TYPE *,' '
        WRITE (5,394)
394     FORMAT ('$','    COLOR (C) OR B&W (B) IMAGE? ')
        READ (5,2222) RESP1
```

```
2222    FORMAT(A)
        IF (RESP1.NE.'C'.AND.RESP1.NE.'B')GOTO 234

IF (RESP1.EQ.'C')THEN
        TYPE *,' '
        WRITE (5,499)
499     FORMAT ('$,'    "COLORRED" (R) OR NORMAL COLOR (C) SCHEME? ')
        READ (5,2222) RESP2
        ENDIF

500     CALL IMAGE(NEWOLD,FILEEXT,CHFREQ_C,RESP1,RESP2,SHAPEANS,IXLENGTH,
    1   FILENAME,DIR,TEBAR)

444     CONTINUE
        STOP
        END

SUBROUTINE IMAGE(NEWOLD,FILEEXT,CHFREQ_C,RESP1,RESP2,SHAPEANS,IXLENGTH,
    1   FILENAME,DIR,TEBAR)

INTEGER*2  D(460),CHANNEL,INPUT,IXLENGTH
        INTEGER*2  X4,Y4,N1,N2,TRFREQ,SCANDIST
        CHARACTER*1 RESP1*1,SHAPEANS*1,RESP2*1,TEBAR
        CHARACTER  CHFREQ_C*3
        REAL       RMIN, RMAX, MEAN
        BYTE       B, CHFREQ(3), BSUFFREQ(4),BZERO(2)
        BYTE       BFILENAME(34), BSCALEMARK(4)
        BYTE       BDATA_STATUS(40), BLABEL(30)
        BYTE       CHMEAN(5),CHRMAX(5),CHRMIN(5)
        CHARACTER  FILNAM*48, LABEL*30, FILEEXT*23
        CHARACTER  L*48, DIR*16,CZERO*2
        CHARACTER  SUFFREQ*4, FILENAME*34, SCALEMARK*4, DATA_STATUS*40

EQUIVALENCE ( L,B )
        EQUIVALENCE ( BSCALEMARK, SCALEMARK )
        EQUIVALENCE ( BSUFFREQ, SUFFREQ )
        EQUIVALENCE ( BDATA_STATUS, DATA_STATUS )
        EQUIVALENCE ( BLABEL, LABEL )
        EQUIVALENCE ( CZERO, BZERO )

CZERO='0 '
        LLLL=0
        IIIMAGE=1

212     CONTINUE

IF (IIIMAGE.EQ.1)FILNAM='_VEL_C_'//CHFREQ_C//'.PDK'

501     CONTINUE
        CHANNEL=0
        IF (CHANNEL.NE.0.AND.CHANNEL.NE.2.AND.CHANNEL.NE.3) GOTO 501
        IF (CHANNEL.EQ.0) THEN
          INPUT=0
```

```
            MASK=1
            ELSEIF (CHANNEL.EQ.2) THEN
            INPUT=1
            MASK=4
            ELSEIF(CHANNEL.EQ.3) THEN
            INPUT=2
            MASK=8
            ENDIF

CALL ERASE

19          OPEN (UNIT=6,FILE=DIR//FILEEXT//FILNAM,STATUS='OLD',
            1FORM='UNFORMATTED')

READ(6) X4,Y4,N1,N2,IVALUE
            READ(6) SCANDIST,TRFREQ
            READ(6) RMIN,RMAX,MEAN

IF ( IVALUE.EQ.1 ) LABEL='VELOCITY CM/US'

ICOLORBAR=0
            SUFFREQ=' MHZ'
            SCALEMARK='1 MM'
            DATA_STATUS=LABEL

CALL GRNIN(1,INPUT,INPUT,INPUT)
            CALL GRNBY(1,1,1,1)
            CALL GRSBFD

C *********************MODIFICATION FOR COMPLEX SHAPES ******C
            IF (SHAPEANS.NE.'Y')IX49=X4

IF (SHAPEANS.EQ.'Y')THEN
            IX49=IXLENGTH
            ENDIF

DO 100 I=1,IX49
            IF (SHAPEANS.NE.'Y')THEN
            IXSTART=I-1
            IYSTART=1
            IYLENGTH=Y4
       READ(6)D
            GOTO 789
            ELSEIF (SHAPEANS.EQ.'Y')THEN
              IF (I.NE.1.AND.IYLENGTH.EQ.1)GOTO 100
            READ(6,END=100)IXSTART,IYSTART,IYLENGTH
            DO 7897 IJK=1,IYLENGTH
7897        READ(6)D(IJK)
789         CONTINUE
            ENDIF
            CALL GRWAW(D,IXSTART,IYSTART,1,IYLENGTH,0,0,0,1,1)
C ************************************************************ C
            CALL GRSBFD
100         CONTINUE
```

```
       IF (RESP1.EQ.'B')THEN
       IF (TEBAR.EQ.'N')GOTO 213
       CALL PLACEBAR(0)
       GOTO 8999
       ELSEIF (RESP1.NE.'B')THEN

IF (RESP2.EQ.'C')THEN
       CALL COLORS (IVALUE,ICOLORBAR)
       ELSEIF (RESP2.EQ.'R')THEN
       CALL COLORRED (IVALUE,ICOLORBAR)
       ENDIF

ENDIF

IF (TEBAR.EQ.'N')GOTO 213

8999   DECODE (34,8989,FILENAME) BFILENAME
8989   FORMAT (34A1)

ENCODE (3,909,CHFREQ) TRFREQ
909    FORMAT (I3)

CALL GRFCD (1,255,0,0,BFILENAME,1,441,6,0,34,0,0,0)
       CALL GRFCD (1,255,0,0,CHFREQ,200,441,6,0,3,0,0,0)
       CALL GRFCD (1,255,0,0,BSUFFREQ,215,441,6,0,4,0,0,0)

CC
CC PRINT LABEL TO GRINNELL
CC
       NCHAR=LEN(DATA_STATUS)
       DO 765 IKY=1,NCHAR
        IKX=400-(IKY-1)*13
        CALL GRFCD (1,255,0,0,BDATA_STATUS(IKY),505,IKX,0,0,1,0,0,0)
        CALL GRSBFD
765    CONTINUE

CC
CC CALCULATE MAX, MIN, AND MEAN
CC
       IF (IVALUE.EQ.1.OR.IVALUE.EQ.2.OR.IVALUE.EQ.6.OR.IVALUE.EQ.7) THEN
       IF (IVALUE.EQ.1) THEN
           IF (RMAX.EQ.1.0) RMAX=.9999
           ENDIF
           RRMAX=RMAX*10.**4.
           RRMIN=RMIN*10.**4.
           RMEAN=MEAN*10.**4.

ELSEIF (IVALUE.EQ.3.OR.IVALUE.EQ.4) THEN
         RRMAX=RMAX/100.
```

```
              RRMIN=RMIN/100.
              RMEAN=MEAN/100.

ELSEIF (IVALUE.EQ.5) THEN
              IF (RMAX.GE.100.)RMAX=99.9
              IF (RMIN.GE.100.)RMIN=99.9
              IF (MEAN.GE.100.)MEAN=99.9
              IF (RMAX.LT.10.)THEN
                 RRMAX=RMAX*10.**4.
                 RRMIN=RMIN*10.**4.
                 RMEAN=MEAN*10.**4.
              ELSE
                 RRMAX=RMAX*10.**3.
                 RRMIN=RMIN*10.**3.
                 RMEAN=MEAN*10.**3.
              ENDIF
           ENDIF
           IF (IVALUE.EQ.2.OR.IVALUE.EQ.6.OR.IVALUE.EQ.7) THEN
              JKMN=465
           ELSEIF (IVALUE.EQ.1.OR.IVALUE.EQ.3.OR.IVALUE.EQ.4)THEN
              JKMN=463
           ELSEIF (IVALUE.EQ.5)THEN
              JKMN=470
           ENDIF

CC DRAW DECIMAL POINT FOR MIN AND MAX TO GRINNELL

DO 9879 IUY=0,350,350
                 CALL GRFAR (1,255,0,0,JKMN,IUY,1,1)
                 CALL GRSBFD
        9879     CONTINUE

IMEAN=JNINT(RMEAN)
              IRMAX=JNINT(RRMAX)
              IRMIN=JNINT(RRMIN)

TYPE *,' '
              TYPE *,'CORRECTED:'
              TYPE *,'IRMAX=',IRMAX
              TYPE *,'IRMIN=',IRMIN
              TYPE *,'IMEAN=',IMEAN
              TYPE *,' '

IF (IMEAN.GE.1.0*10.**5.) GOTO 73920
              ENCODE (5,9878,CHMEAN) IMEAN
        73920 IF (IRMAX.GE.1.0*10.**5.) GOTO 73921
              ENCODE (5,9878,CHRMAX) IRMAX
        73921 IF (IRMIN.GE.1.0*10.**5.) GOTO 73922
              ENCODE (5,9878,CHRMIN) IRMIN
        73922 CONTINUE
        9878  FORMAT (I5)
```

```
            IF (IMEAN.GE.1.0*10.**6.)GOTO 93920
            ZZZZZZ=RRMAX-RRMIN
            IF (ZZZZZZ.EQ.0.)ZZZZZZ=1.
            SCALEF=((RMEAN-RRMIN)/(ZZZZZZ))*350.  !SC. MEAN TO CLR BAR
            ISCALEF=ININT(SCALEF)
93920       CONTINUE

IF (IMEAN.GE.1.0*10.**6.)GOTO 83920
            CALL GRFCDS (1,255,CHMEAN,458,ISCALEF,6,0,4)
83920       IF (IRMAX.GE.1.0*10.**6.)GOTO 83921
            CALL GRFCDS (1,255,CHRMAX,458,350,6,0,4)
83921       IF (IRMIN.GE.1.0*10.**6.)GOTO 83922
            CALL GRFCDS (1,255,CHRMIN,458,0,6,0,4)
            CALL GRSBFD
83922       CONTINUE
9877        CONTINUE

IF (IVALUE.EQ.2) THEN
          JKMN=465
             ELSEIF (IVALUE.EQ.1.OR.IVALUE.EQ.3.OR.IVALUE.EQ.4.OR.IVALUE.EQ.6
     1           .OR.IVALUE.EQ.7)THEN
            JKMN=463
             ELSEIF (IVALUE.EQ.5)THEN
              JKMN=470
              ENDIF
            CALL GRFAR (1,255,0,0,JKMN,ISCALEF,1,1)
            CALL GRSBFD
95631       CONTINUE

CC
CC DRAW SCALE ONTO IMAGE
CC

RSCANDIST=FLOATI(SCANDIST)
            PIXELS=(X4*1.)/(RSCANDIST)
            IPIXELS=ININT(PIXELS)
            CALL GRFVCS (1,255,340,420,340+IPIXELS,420)
            CALL GRFCDS (1,255,BSCALEMARK,345,410,6,0,4)
            CALL GRSBFD

C! FOR DRAWING INITIAL ZEROES FOR ATTENUATION COEFF. <0.1
            IF (IVALUE.EQ.2.AND.RRMIN.LT.1000.)THEN
            CALL GRFCDS (1,255,BZERO,JKMN,0,6,0,2)
            CALL GRSBFD
            ENDIF

213         CONTINUE

201         CLOSE(6)

1           FORMAT($',' WHICH IMAGE TO VIEW [*.PDK IN ROTH.IMAG]?')
2           FORMAT(A)
3           FORMAT($','Channel  (0,2,3) ?')
```

```
      4     FORMAT( '$Description ?? ' )
      5     FORMAT('0')
      6     FORMAT(' ',A )
      7     FORMAT(' Range = ',A,' ',A )
      8     FORMAT(' Mean =   ',A15,' ',A )
      9  FORMAT(I)

TYPE *,''

999     CALL GRSEND

444     CONTINUE
            RETURN
            END

SUBROUTINE COLORSUB (IVALUE,ICOLORBAR)

INTEGER*2 NR(256),NB(256),NG(256),IARRAY(18)
            DATA IARRAY/0,2,1,0,1,2,1,0,2,1,2,0,2,0,1,2,1,0/

IF (IVALUE.GT.10) GOTO 9876
            CALL GRINIT_OLD
            CALL GRSRST
            CALL GRZFC(0,0)
            CALL GRZCL(0,255,255)
            CALL GRZON(0,1)
            CALL GRSBFD

B=4
            A=2

L=256
            IL=L/B
            JL=A*IL

DO 100 I=1,IL
            NB(I)=255
            NR(I)=0
            NG(I)=B*I
            IF(NG(I).GT.255)THEN
            NG(I)=255
            ENDIF
    100 CONTINUE

DO 200 I=IL+1,JL
            BB=((B/(1-A))*I)+((A/(A-1))*L)
            NG(I)=255
            NR(I)=0
            NB(I)=BB
            IF (NB(I).GT.255)THEN
            NB(I)=255
            ENDIF
    200 CONTINUE
```

```
      DO 300 I=JL+1,JL+IL
      RR=(B*I)-(A*L)
      NG(I)=255
      NB(I)=0
      NR(I)=RR
      IF (NR(I).GT.255)THEN
      NR(I)=255
      ENDIF
300   CONTINUE

DO 400 I=JL+IL+1,L
      GG=((-B)*I)+(B*L)
      NR(I)=255
      NB(I)=0
      NG(I)=GG
      IF(NG(I).GT.255)THEN
      NG(I)=255
      ENDIF
400   CONTINUE

800   KC=0

NR(1)=0
      NG(1)=0
      NB(1)=0
      NR(256)=255
      NG(256)=255
      NB(256)=255

889   CALL GRNWR(1,NB,IARRAY(1+KC),0,256,0)
      CALL GRNWR(1,NG,IARRAY(2+KC),0,256,0)
      CALL GRNWR(1,NR,IARRAY(3+KC),0,256,0)
      CALL GRSBFD
      CALL GRNIN(0,0,0,0)
      IF (ICOLORBAR.EQ.1) THEN
      CALL GRNBY (0,0,0,0)
      ENDIF
      CALL GRSBFD
C     IF (IVALUE.EQ.1.OR.IVALUE.EQ.3.OR.IVALUE.EQ.5.OR.IVALUE.EQ.7) THEN
      DO 1111 I=1,300
      DO 1111 J=1,900
1111  CONTINUE
      GOTO 950
950   KC=0
9876  RETURN
      END

SUBROUTINE PLACEBAR (ICOLORBAR)

CC ------Draw colorbar at right side of screen-------

INTEGER*2 NA(45)
```

```
        IF (ICOLORBAR.EQ.1) GOTO 1010
        CONTINUE
        DO 1000 I=0,350
        DO 2000 J=1,19
        G=I*(254.0/350.0)
        NA(J)=G
2000    CONTINUE
        CALL GRWLW(NA,410,I,19,0,0,1,1)
        CALL GRSBFD
1000    CONTINUE
1010    CONTINUE
        RETURN
        END

SUBROUTINE SAVEBAR

INTEGER*2 BAR(6)

TYPE *,' '
        TYPE *,'Creating and saving the color bar...'
        TYPE *,' '

OPEN(UNIT=34,NAME='BARFILE',STATUS='NEW',
        1FORM='UNFORMATTED',BLOCKSIZE=1024)

CALL GRNIN(1,0,0,0)
        CALL GRNBY(1,1,1,1)
        CALL GRSBFD

DO 2060 IBBEL=0,459,3
        CALL GRRLW (410,IBBEL,6,1,BAR)
            WRITE(34) BAR
2060  CONTINUE

CALL GRSBFD
        CLOSE(34)
        RETURN
        END

SUBROUTINE ERASE

M=4095
        N=4095
      CALL GRFER (M,N,0)
        CALL GRSBFD
        END

SUBROUTINE COLORS (IVALUE,ICOLORBAR)
```

```
      INTEGER*2 NR(256),NB(256),NG(256),IARRAY(18)
      DATA IARRAY/0,2,1,0,1,2,1,0,2,1,2,0,2,1,2,0,1,2,1,0/
      INTEGER*2 NA(45)

IF (IVALUE.GT.10) GOTO 9876
      CALL GRINIT_OLD
      CALL GRSRST
      CALL GRZFC(0,0)
      CALL GRZCL(0,255,255)
      CALL GRZON(0,1)
      CALL GRSBFD

B=4
      A=2

L=256
      IL=L/B
      JL=A*IL

DO 100 I=1,IL
      NB(I)=255
      NR(I)=0
      NG(I)=B*I
      IF(NG(I).GT.255)THEN
      NG(I)=255
      ENDIF
  100 CONTINUE

DO 200 I=IL+1,JL
      BB=((B/(1-A))*I)+((A/(A-1))*L)
      NG(I)=255
      NR(I)=0
      NB(I)=BB
      IF (NB(I).GT.255)THEN
      NB(I)=255
      ENDIF

200 CONTINUE

DO 300 I=JL+1,JL+IL
      RR=(B*I)-(A*L)
      NG(I)=255
      NB(I)=0
      NR(I)=RR
      IF (NR(I).GT.255)THEN
      NR(I)=255
      ENDIF
  300 CONTINUE

DO 400 I=JL+IL+1,L
      GG=((-B)*I)+(B*L)
      NR(I)=255
```

```
          NB(I)=0
          NG(I)=GG
          IF(NG(I).GT.255)THEN
          NG(I)=255
          ENDIF
400    CONTINUE

800    KC=0

NR(1)=0
          NG(1)=0
          NB(1)=0
          NR(256)=255
          NG(256)=255
          NB(256)=255

889       CALL GRNWR(1,NB,IARRAY(1+KC),0,256,0)
          CALL GRNWR(1,NG,IARRAY(2+KC),0,256,0)
          CALL GRNWR(1,NR,IARRAY(3+KC),0,256,0)
          CALL GRSBFD
          CALL GRNIN(0,0,0,0)
          IF (ICOLORBAR.EQ.1) THEN
          CALL GRNBY (0,0,0,0)
          ENDIF
          CALL GRSBFD
          DO 1111 I=1,300
          DO 1111 J=1,900
1111   CONTINUE
          GOTO 950
950    KC=0

CC -------Draw colorbar at right side of screen-------

9876   IF (ICOLORBAR.EQ.1) GOTO 1010
          CONTINUE
          DO 1000 I=0,350
          DO 2000 J=1,19
          G=I*(254.0/350.0)
          NA(J)=G
2000   CONTINUE
          CALL GRWLW(NA,410,I,19,0,0,1,1)
          CALL GRSBFD
1000   CONTINUE
1010   CONTINUE
          RETURN
          END

Subroutine colorred(IVALUE,ICOLORBAR)

INTEGER*2 NR(256),NB(256),NG(256),IARRAY(18)
          DATA IARRAY/0,1,2,0,2,1,1,0,2,1,2,0,2,0,1,2,1,0/
          INTEGER*2 NA(45)
```

```
10010   format(A)
10020   format(I)
        NM256 = 0

IF (IVALUE.GT.10) GOTO 9876

CALL GRINIT_OLD
C       CALL GRSRST
        CALL GRSBFD
        L=256
        IL=L/3
        JL=2*IL
        NM256=255

DO 100 I=1,IL
        NB(I)=0
        NR(I)=I*3
        NG(I)=0
        IF( NR(I).GT.253 )NR(I)=253
100     CONTINUE

DO 200 I=IL+1,JL
        NG(I)=3*(I-IL)
        NR(I)=253
        NB(I)=0
        IF( NG(I).GT.253 )NG(I)=253
200     CONTINUE

DO 300 I=JL+1,255
        NG(I)=253
        NR(I)=253
        NB(I)=3*(I-JL)
        IF( NR(I).GT.253 )NR(I)=253
300     CONTINUE

800     KC=6
        NR(1)=0
        NG(1)=0
        NB(1)=0
        NR(256)=NM256
        NG(256)=NM256
        NB(256)=NM256

840     CALL GRNWR(1,NB,IARRAY(1+KC),0,256,0)
        CALL GRNWR(1,NG,IARRAY(2+KC),0,256,0)
        CALL GRNWR(1,NR,IARRAY(3+KC),0,256,0)
        CALL GRSBFD
        CALL GRNIN(0,0,0,0)
        CALL GRSBFD
        CALL GRNBY(0,0,0,0)
        CALL GRSBFD
C       WRITE( 5,10860 )
C10860   format( '$ <CR> for next color scheme, Q to quit :' )
C       READ( 5,10010 )ANS
```

```
C       IF( ANS.EQ.'Q' .OR. ANS.EQ.'q' )GOTO 9876
        GOTO 9876
        KC = KC+3
        IF (KC.GE.18) KC=0
        GOTO 840

CC ------Draw colorbar at right side of screen------

9876    IF (ICOLORBAR.EQ.1) GOTO 1010
        CONTINUE
        DO 1000 I=0,350
        DO 2000 J=1,19
        G=I*(254.0/350.0)
        NA(J)=G
2000    CONTINUE
        CALL GRWLW(NA,410,I,19,0,0,1,1)
        CALL GRSBFD
1000    CONTINUE
1010    CONTINUE

C 900   CALL GRSEND
        return
        END
```

What is claimed is:

1. A pulse-echo, immersion method for ultrasonic evaluation of a material, employing automatic scanning and digital imaging to obtain an image of a property of said material, wherein said material is held in a holding apparatus which is positioned in an immersion liquid over an acoustic reflector, said reflector having an acoustic impedance which is greater than that of said liquid, and wherein nonlevelness in said holding apparatus and material thickness are accounted for and eliminated, said method comprising:

(i) ultrasonically scanning said material at a plurality of scan points and receiving the first and second echoes, each of which is a complete waveform, reflected off the back surface of said material and the first echo reflected off the front surface of said reflector both with and without the presence of said material;

(ii) adjusting the time delay for each said received echo from each said scan point during said scanning in (i) above, gating each said received echo so that it is centered within its respective time window;

(iii) automatically scanning said material at said scan points to receive said first and second back surface echoes and said two front surface echoes using the information obtained in (ii) above, so that each echo received from each scan point during said automatic scanning is centered within its time window;

(iv) digitizing each echo received during said automatic scanning and determining the time delay between said first two successive sample back surface echoes, $2\tau$, and the time delay, $\Delta t$, between the two different reflector front surface echoes received at each scan point during said automatic scanning and calculating the wave velocity, using a cross correlation function, at each said scan point from $$v = c\left(\frac{\Delta t}{2\tau} + 1\right)$$

where c is the speed of the ultrasonic wave transmitted in said liquid, and (v) scaling the velocity values obtained in (iv) to corresponding proportional color or grey scale values and displaying the resulting image.

2. A method according to claim 1 wherein a single transducer is used.

3. A method according to claim 2 wherein said transducer is a high frequency transducer which emits a frequency between 1–100 MHz.

4. A pulse-echo, immersion method for ultrasonic evaluation of a material employing a single transducer, automatic scanning and digital imaging to obtain an image of a property of said material, wherein said material has a uniform thickness variation and is positioned in an immersion liquid between said transducer and an accoustic reflector, said method comprising:

(I) accounting for and eliminating nonlevelness in the set-up and said material thickness variation by;

(a) performing a preliminary scan along both the x-and y-directions of the material to provide slant correction factors which are input into a computer to account for said nonlevelness and thickness variation during the subsequent automatic scanning for said material evaluation in (ii) below;

(b) adjusting the time delay during said preliminary scan for any received echoes which are not centered in the scan time window, so that each received echo is centered in its time window;

(ii) automatically scanning said material at a plurality of scan points in both the x- and y-directions to receive the first and second back surface echoes and front surface echoes with and without the presence of said material between said transducer and reflector using the information obtained in (i) above, so that each echo received from each scan point during said automatic scanning is centered within its time window;

(iii) digitizing each echo received during said automatic scanning and determining the time delay between said first two successive sample back surface echoes, $2\tau$, and the time delay, $\Delta t$, between the two different reflector front surface echoes received at each scan point during said automatic scanning and calculating the wave velocity at each said scan point from $$v = c\left(\frac{\Delta t}{2\tau} + 1\right)$$

where c is the speed of the ultrasonic wave transmitted in said liquid, and (iv) scaling the velocity values obtained in (iii) to corresponding proportional color or grey scale values and displaying the resulting image.

5. A method according to claim 4 wherein said back and front surface echoes received from the first and last scan points in both the x- and y-directions during said preliminary scan determine said time base adjustments needed for each echo to be centered within the time frame for it.

6. A method according to claim 5 wherein the location of the time window during said automatic scanning for said material evaluation is automatically adjusted via computer control by using the formula:

$$W_{DT} = T_I + [(X_{SC})(X_{SN})(X_{SI}) + (Y_{SC})(Y_{SN})(YSI)]$$

wherein $W_{DT}$ is the correct delay time window at a particular scan location, $T_I$ is the time delay at the the initial scan location, $X_{SC}$ and $Y_{SC}$ are the x- and y-direction slant correction factors, $X_{SN}$ and $Y_{SN}$ are the scan point numbers in the x- and y-directions, and $X_{SI}$ and $Y_{SI}$ are the x- and y-direction scan increments.

7. A method according to claim 6 wherein two scans are automatically made to obtain said first two back surface echoes and said two different reflector front surface echoes.

8. A method according to claim 7 wherein said first two back surface echoes and said reflector echo with said material present are made in said first scan.

9. A method according to claim 6 wherein three scans are automatically made to obtain said first two back surface echoes and said two different reflector front surface echoes.

10. A method according to claim 9 wherein said first two back surface echoes are received in one scan, wherein said reflector echo with said material present is made in another scan, and wherein and said reflector echo without said material present is received in yet another scan.

11. A method according to claim 9 wherein said first back surface echo is received in said first scan, wherein said second back surface echo is received in said second scan, wherein said reflector echo with said material present is made in said third scan, and wherein said reflector echo without said material present is received in said fourth scan.

12. A method according to claim 6 wherein four scans are automatically made to obtain said first two back surface echoes and said two different reflector front surface echoes.

13. An ultrasonic, pulse-echo, immersion method employing automatic scanning and digital imaging to obtain an image of a microstructural property of a material positioned in an immersion liquid between a transducer and an acoustic reflector, said method comprising:

(i) automatically scanning said material at least three times at a plurality of scan points in both the x- and y-directions to receive the first and second back surface echoes and front surface echoes with and without the presence of said material between said transducer and reflector, each of said echoes received being a complete waveform and gated within a time window;

(ii) digitizing each echo received during said automatic scanning and determining the time delay between said first two successive sample back surface echoes, $2\tau$ and the time delay, $\Delta t$, between the two different reflector front surface echoes received at each scan point during said automatic scanning and calculating the wave velocity at each said scan point from $$v = c\left(\frac{\Delta t}{2\tau} + 1\right)$$

where c is the speed of the ultrasonic wave transmitted in said liquid, and (iii) scaling the velocity values obtained in (ii) to corresponding proportional color or grey scale values and displaying the resulting image.

14. A method according to claim 13 wherein four scans are automatically made to obtain said first two back surface echoes and said two different reflector front surface echoes.

15. A method according to claim 14 wherein said first back surface echo is received in said first scan, wherein said second back surface echo is received in said second scan, wherein said reflector echo with said material present is made in said third scan, and wherein and said reflector echo without said material present is received in said fourth scan.

* * * * *